United States Patent
Lee et al.

(10) Patent No.: US 9,385,327 B2
(45) Date of Patent: Jul. 5, 2016

(54) HETEROCYCLIC COMPOUND AND ORGANIC LIGHT-EMITTING DEVICE INCLUDING THE SAME

(71) Applicant: Samsung Display Co. Ltd., Yongin-si, Gyeonggi-do (KR)

(72) Inventors: Sun-Young Lee, Yongin-si (KR); Yoon-Hyun Kwak, Yongin-si (KR); Bum-Woo Park, Yongin-si (KR); Jong-Won Choi, Yongin-si (KR); Wha-Il Choi, Yongin-si (KR); So-Yeon Kim, Yongin-si (KR); Ji-Youn Lee, Yongin-si (KR)

(73) Assignee: Samsung Display Co., Ltd., Yongin-si (KR)

( * ) Notice: Subject to any disclaimer, the term of this patent is extended or adjusted under 35 U.S.C. 154(b) by 86 days.

(21) Appl. No.: 13/750,955

(22) Filed: Jan. 25, 2013

(65) Prior Publication Data

US 2014/0034915 A1    Feb. 6, 2014

(30) Foreign Application Priority Data

Aug. 1, 2012    (KR) .................. 10-2012-0084583

(51) Int. Cl.
*H01L 51/50*    (2006.01)
*H01L 51/00*    (2006.01)
(Continued)

(52) U.S. Cl.
CPC .......... *H01L 51/0074* (2013.01); *C07D 307/77* (2013.01); *C07D 405/14* (2013.01);
(Continued)

(58) Field of Classification Search
None
See application file for complete search history.

(56) References Cited

U.S. PATENT DOCUMENTS 5,635,308 A    6/1997    Inoue et al.
5,645,948 A    7/1997    Shi et al.
(Continued)

FOREIGN PATENT DOCUMENTS

CN    101587939 A    11/2009
JP    8-12600    1/1996
(Continued)

OTHER PUBLICATIONS

Cameron et al., Synthesis of a Natural Polychloro Dinaphthofuran Quinone, 1980, Tetrahedron Letters, vol. 21, pp. 1385-1386.*

(Continued)

*Primary Examiner* — Gregory Clark
(74) *Attorney, Agent, or Firm* — Lewis Roca Rothgerber Christie LLP

(57) ABSTRACT

A heterocyclic compound is represented by Formula 1.

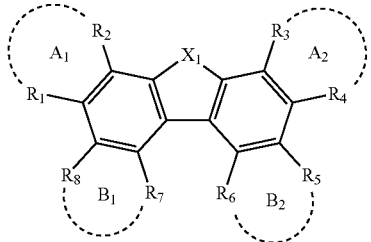

An organic light emitting device includes a first electrode, a second electrode and an organic layer between the first and second electrodes. The organic layer includes the heterocyclic compound. An organic light-emitting display apparatus includes the organic light-emitting device and a transistor including a source, a drain, a gate and an active layer. The source or the drain is electrically connected to the first electrode of the organic light-emitting device.

19 Claims, 1 Drawing Sheet

(51) Int. Cl.

| | | |
|---|---|---|
| *H01L 27/32* | (2006.01) | |
| *C07D 405/14* | (2006.01) | |
| *C07D 407/14* | (2006.01) | |
| *C07D 409/14* | (2006.01) | |
| *C07D 491/147* | (2006.01) | |
| *C07D 493/14* | (2006.01) | |
| *C07D 495/14* | (2006.01) | |
| *C07D 307/77* | (2006.01) | |
| *C09K 11/06* | (2006.01) | |
| *H05B 33/14* | (2006.01) | |

(52) U.S. Cl.
CPC ............ *C07D407/14* (2013.01); *C07D 409/14* (2013.01); *C07D 491/147* (2013.01); *C07D 493/14* (2013.01); *C07D 495/14* (2013.01); *C09K 11/06* (2013.01); *H01L 27/3225* (2013.01); *H01L 51/0061* (2013.01); *H01L 51/0062* (2013.01); *H01L 51/0065* (2013.01); *H01L 51/0071* (2013.01); *H01L 51/0073* (2013.01); *H01L 51/50* (2013.01); *H05B 33/14* (2013.01); *C09K 2211/1007* (2013.01); *C09K 2211/1014* (2013.01); *C09K 2211/1088* (2013.01); *C09K 2211/1092* (2013.01); *H01L 51/0072* (2013.01); *H01L 51/0081* (2013.01); *H01L 51/0085* (2013.01); *H01L 51/506* (2013.01); *H01L 51/5012* (2013.01); *H01L 51/5016* (2013.01); *H01L 51/5056* (2013.01); *H01L 51/5072* (2013.01); *H01L 51/5088* (2013.01); *H01L 51/5092* (2013.01); *H01L 2251/308* (2013.01)

(56) References Cited

U.S. PATENT DOCUMENTS

| | | | | |
|---|---|---|---|---|
| 5,972,247 | A | 10/1999 | Shi et al. | |
| 6,465,115 | B2 | 10/2002 | Shi et al. | |
| 6,596,415 | B2 | 7/2003 | Shi et al. | |
| 2006/0124924 | A1* | 6/2006 | Suh et al. | 257/40 |
| 2007/0018569 | A1* | 1/2007 | Kawamura et al. | 313/504 |
| 2007/0224446 | A1* | 9/2007 | Nakano et al. | 428/690 |
| 2009/0131673 | A1 | 5/2009 | Tanabe et al. | |
| 2011/0253944 | A1 | 10/2011 | Han et al. | |
| 2011/0266526 | A1* | 11/2011 | Ma et al. | 257/40 |
| 2012/0007063 | A1 | 1/2012 | Langer et al. | |

FOREIGN PATENT DOCUMENTS

| | | |
|---|---|---|
| JP | 2000-003782 | 1/2000 |
| KR | 10-2010-0003624 | 1/2010 |
| KR | 10-2010-0074081 | 7/2010 |
| KR | 10-2010-0108924 | 10/2010 |
| KR | 10-2011-0013220 | 2/2011 |
| WO | WO 2006/128800 A1 | 12/2006 |
| WO | WO 2010/114264 A2 | 7/2010 |
| WO | WO 2011/014039 A1 | 2/2011 |

OTHER PUBLICATIONS

Musgrove et al., Condensations of thiophene with ketones, 2002, J. Chem., Perkins Trans, 1, pp. 1944-1947.*
Adachi et al., Confinement of charge carriers and molecular excitons within 5-nm-thick emitter layer in organic electroluminescent devices with a double heterostructure, Appl. Phys. Lett. 57, 1990, pp. 531-553, 3 pages.
Shigehiro et al., Diphenylamino-Substituted 2,5-Diarylsiloles for Single-Layer organic Electroluminescent Devices, Chemistry Letters 2001; pp. 98-99, 2 pages.
Tang et al., Organic electroluminescent diodes, Appl. Phys. Letter 51, Sep. 21, 1987, pp. 913-915, 3 pages.
Youichi et al., Synthesis, Characterization, and Electron-Transport Property of Perfluorinated Phenylene Dendrimers, J. Am. Chem. Soc. 2000, 122, 1832-1833, 2 pages.
KIPO Office action dated Nov. 5, 2015 in priority Application No. KR 10-2012-0084583, 8 pages.
SIPO Office Action dated May 12, 2016 for corresponding Chinese Patent application 201310074713.8 (14 pages).
Imamura, Koichi, et al., "Application of Flash Vacuum Pyrolysis to the Synthesis of Sulfur-containing Heteroaromatic Systems," Tetrahedron Letters, 1990, 40, pp. 2789-2792.
Wang, Jing, et al., "Synthesis and characterization of new planar butterfly-shaped fused oligothiophenes," Tetrahedron, 2012, 68, pp. 1192-1197.
Zhang, Jing-lei, et al., "Improved Performances of Organic Light-emitting Diodes by Insertion of $Nb_2O_5$ as Hole Injection Layer," Chinese Journal of Liquid Crystals and . Displays, Feb. 2008, 23, 1, pp. 11-15 (Abstract).

* cited by examiner

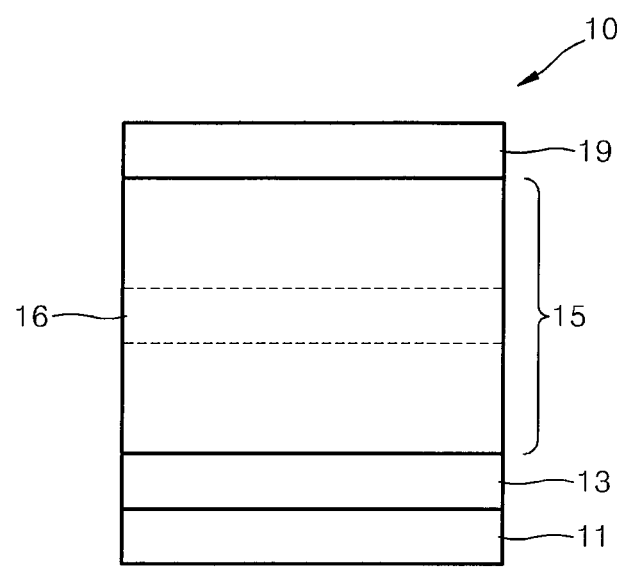

HETEROCYCLIC COMPOUND AND ORGANIC LIGHT-EMITTING DEVICE INCLUDING THE SAME

CROSS-REFERENCE TO RELATED PATENT APPLICATION

This application claims priority to and the benefit of Korean Patent Application No. 10-2012-0084583, filed on Aug. 1, 2012 in the Korean Intellectual Property Office, the entire content of which is incorporated herein by reference.

BACKGROUND

1. Technical Field

The present invention relates to a heterocyclic compound and an organic light-emitting device including the same. More particularly, the invention relates to a fused ring compound, and to an organic light-emitting device that includes the compound.

2. Description of the Related Art

Organic light-emitting devices (OLEDs) are self-emitting devices having advantages such as wide viewing angles, good contrast, quick response speeds, high brightness, and good driving voltage characteristics. OLEDs can also provide multicolored images. Due to these characteristics, OLEDs have been receiving growing attention.

An existing organic light-emitting device has a structure that includes an anode disposed on a substrate, on which is sequentially stacked a hole transport layer (HTL), an emission layer, an electron transport layer (ETL) and a cathode. The HTL, the EML, and the ETL are normally formed of organic compounds. When a voltage is applied between the anode and the cathode, holes injected from the anode move to the EML via the HTL, and electrons injected from the cathode move to the EML via the ETL. The holes and electrons (carriers) recombine in the EML to generate excitons. When the excitons drop from an excited state to a ground state, light is emitted.

A major factor affecting luminescent efficiency of organic light-emitting devices is the organic luminescent material. Fluorescent materials have been widely used as organic light-emitting materials, but may have limited emission efficiency due to having a mere 25% probability of being in an excited singlet state. Meanwhile, phosphorescent materials have a 25% probability of being in an excited singlet state and a 97% probability of being in an excited triplet state, and thus may improve emission efficiency up to four times as compared with fluorescent materials (based on theoretical electroluminescence mechanisms), and may achieve a 100% internal quantum efficiency. Thus, use of phosphorescent materials is gradually increasing.

Anthracene derivatives are typical organic light-emitting materials. However, an organic light-emitting device using an anthracene derivative in which two or three oligomeric species of anthracene are linked by conjugation may have a narrow energy gap, low blue-light color purity, and low emission efficiency, and thus is not satisfactory.

4,4'-Bis(carbazole-9-yl)biphenyl (CBP) have also been used as a phosphorescent host material, but is not suitable for green-light emission due to its wide bandgap and reduced emission efficiency. It is also not easy to control hole or electron mobility and adjust the charge balance with this material.

These existing organic light-emitting materials do not yield satisfactory emission characteristics, such as emission efficiency.

SUMMARY

Embodiments of the present invention provide a heterocyclic compound with improved emission characteristic as an organic light-emitting material.

Embodiments of the present invention also provide an organic light-emitting device with improved emission efficiency and lifetime characteristics that includes the heterocyclic compound.

Embodiments of the present invention also provide a high-efficiency, long lifetime organic light-emitting display apparatus including the organic light-emitting device.

According to an aspect of the present invention, a heterocyclic compound is represented by Formula 1 below.

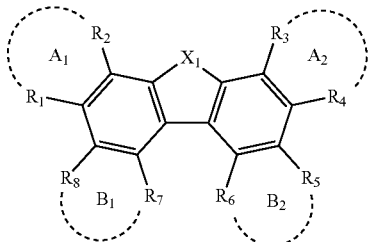

Formula 1

In Formula 1, $X_1$ is an oxygen atom (—O—) or a sulfur atom (—S—).

$R_1$ to $R_8$ are each independently one of a hydrogen atom, a deuterium atom, a halogen atom, a hydroxyl group, a cyano group, an amino group, a nitro group, a carboxyl group, a substituted or unsubstituted $C_1$-$C_{30}$ alkyl group, a substituted or unsubstituted $C_2$-$C_{30}$ alkenyl group, a substituted or unsubstituted $C_2$-$C_{30}$ alkynyl group, a substituted or unsubstituted $C_1$-$C_{30}$ alkoxy group, a substituted or unsubstituted $C_3$-$C_{30}$ cycloalkyl group, a substituted or unsubstituted $C_3$-$C_{30}$ cycloalkenyl group, a substituted or unsubstituted $C_6$-$C_{30}$ aryl group, a substituted or unsubstituted $C_6$-$C_{30}$ aryloxy group, a substituted or unsubstituted $C_6$-$C_{30}$ arylthio group, a substituted or unsubstituted $C_2$-$C_{30}$ heteroaryl group, or a —N($Q_1$)($Q_2$) group. $Q_1$ and $Q_2$ are each independently one of a hydrogen atom, a deuterium atom, a halogen atom, a hydroxyl group, a cyano group, an amino group, a nitro group, a carboxyl group, a substituted or unsubstituted $C_1$-$C_{30}$ alkyl group, a substituted or unsubstituted $C_2$-$C_{30}$ alkenyl group, a substituted or unsubstituted $C_2$-$C_{30}$ alkynyl group, a substituted or unsubstituted $C_1$-$C_{30}$ alkoxy group, a substituted or unsubstituted $C_3$-$C_{30}$ cycloalkyl group, a substituted or unsubstituted $C_3$-$C_{30}$ cycloalkenyl group, a substituted or unsubstituted $C_6$-$C_{30}$ aryl group, a substituted or unsubstituted $C_6$-$C_{30}$ aryloxy group, a substituted or unsubstituted $C_6$-$C_{30}$ arylthio group, or a substituted or unsubstituted $C_2$-$C_{30}$ heteroaryl group. Adjacent $R_1$ to $R_4$ groups optionally bind together to form a ring $A_1$ and/or a ring $A_2$. Similarly, adjacent $R_5$ to $R_8$ groups optionally bind together to form a ring $B_1$ and/or a ring $B_2$. The ring $A_1$, the ring $A_2$, the ring $B_1$, and the ring $B_2$ are each independently one of a substituted or unsubstituted $C_6$-$C_{30}$ aromatic ring or a substituted or unsubstituted $C_2$-$C_{30}$ heteroaromatic ring.

The heterocyclic compound may be a compound represented by Formula 2a or 2b below

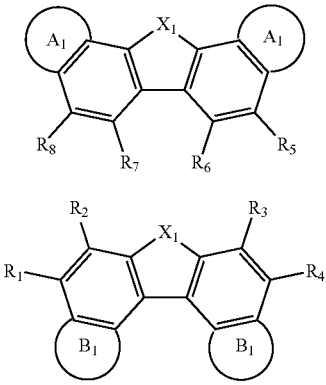

Formula 2a

Formula 2b

In Formulae 2a and 2b, $X_1$, $R_1$ to $R_8$, the ring $A_1$, and the ring $B_1$ are as defined above with respect to Formula 1.

According to another aspect of the present invention, an organic light-emitting device includes a first electrode, a second electrode facing the first electrode, and an organic layer between the first electrode and the second electrode. The organic layer includes the above-described heterocyclic compound.

The organic layer may include at least one of a hole injection layer, a hole transport layer, a functional layer having both hole injection and hole transport capabilities, a buffer layer, an emission layer, a hole blocking layer, an electron transport layer, an electron injection layer, and/or a functional layer having both electron injection and electron transport capabilities.

The organic layer may include at least one of a hole injection layer, a hole transport layer, and a functional layer having both hole injection and hole transport capabilities, and at least one of the hole injection layer, the hole transport layer, and the functional layer having both hole injection and hole transport capabilities includes the heterocyclic compound.

At least one of the hole injection layer, the hole transport layer, and the functional layer having both hole injection and hole transport capabilities may further include a charge-generating material, and the charge-generating material is at least one of a quinone derivative, a metal oxide, and/or a cyano group-containing compound.

The organic layer may include at least one of an electron injection layer, an electron transport layer, and/or a functional layer having both electron injection and electron transport capabilities, and at least one of the electron injection layer, the electron transport layer, and/or the functional layer having both electron injection and electron transport capabilities may include the heterocyclic compound.

The organic layer may include an emission layer, and the emission layer may include the heterocyclic compound.

The heterocyclic compound may be used as a fluorescent or phosphorescent host.

The heterocyclic compound may be used as a fluorescent dopant.

The organic layer may include at least one of an emission layer, an electron injection layer, an electron transport layer, and/or a functional layer having both electron injection and electron transport capabilities, wherein at least one of the electron injection layer and at least one of the electron transport layer, and/or the functional layer having both electron injection and electron transport capabilities may include the heterocyclic compound. The emission layer may include an arylamine compound.

According to another aspect of the present invention, an organic light-emitting display apparatus includes the above-described organic light-emitting device, and a transistor. The transistor includes a source, a drain, a gate, and an active layer. One of the source and the drain of the transistor is electrically connected to the first electrode of the organic light-emitting device.

BRIEF DESCRIPTION OF THE DRAWING

The above and other features and advantages of the present invention will become more apparent by reference to the following detailed description when considered with reference to the attached drawing in which:

FIG. 1 is a schematic cross-sectional view of an organic light-emitting device according to an embodiment of the present invention.

DETAILED DESCRIPTION

As used herein, the term "and/or" includes any and all combinations of one or more of the associated listed items. Expressions such as "at least one of," when preceding a list of elements, modify the entire list of elements and do not modify the individual elements of the list.

According to an aspect of the present invention, a fused ring compound is represented by Formula 1 below.

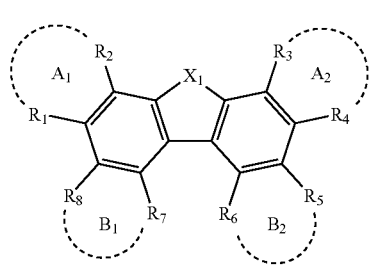

Formula 1

In Formula 1 above, $X_1$ is an oxygen atom (—O—) or a sulfur atom (—S—). The heterocyclic compound of Formula 1 may have a backbone structure including dibenzofuran or dibenzothiophene.

$R_1$ to $R_8$ of Formula 1 are each independently one of a hydrogen atom, a deuterium atom, a halogen atom, a hydroxyl group, a cyano group, an amino group, a nitro group, a carboxyl group, a substituted or unsubstituted $C_1$-$C_{30}$ alkyl group, a substituted or unsubstituted $C_2$-$C_{30}$ alkenyl group, a substituted or unsubstituted $C_2$-$C_{30}$ alkynyl group, a substituted or unsubstituted $C_1$-$C_{30}$ alkoxy group, a substituted or unsubstituted $C_3$-$C_{30}$ cycloalkyl group, a substituted or unsubstituted $C_3$-$C_{30}$ cycloalkenyl group, a substituted or unsubstituted $C_6$-$C_{30}$ aryl group, a substituted or unsubstituted $C_6$-$C_{30}$ aryloxy group, a substituted or unsubstituted $C_6$-$C_{30}$ arylthio group, a substituted or unsubstituted $C_2$-$C_{30}$ heteroaryl group, or a —$N(Q_1)(Q_2)$ group.

The group represented by —$N(Q_1)(Q_2)$ is a monovalent amine derivative group in which $Q_1$ and $Q_2$ are each independently one of a hydrogen atom, a deuterium atom, a halogen atom, a hydroxyl group, a cyano group, an amino group, a nitro group, a carboxyl group, a substituted or unsubstituted $C_1$-$C_{30}$ alkyl group, a substituted or unsubstituted $C_2$-$C_{30}$ alkenyl group, a substituted or unsubstituted $C_2$-$C_{30}$ alkynyl group, a substituted or unsubstituted $C_1$-$C_{30}$ alkoxy group, a substituted or unsubstituted $C_3$-$C_{30}$ cycloalkyl group, a substituted or unsubstituted $C_3$-$C_{30}$ cycloalkenyl group, a substituted or unsubstituted $C_6$-$C_{30}$ aryl group, a substituted or unsubstituted $C_6$-$C_{30}$ aryloxy group, a substituted or unsubstituted $C_6$-$C_{30}$ arylthio group, or a substituted or unsubstituted $C_2$-$C_{30}$ heteroaryl group.

Adjacent $R_1$ to $R_8$ groups in Formula 1 may optionally bind together to form an aromatic or heteroaromatic ring. These combinations may fall into either one of the following two cases.

One of two cases is when adjacent $R_1$ to $R_4$ groups optionally bind together to form a ring $A_1$ and/or a ring $A_2$, while $R_5$ to $R_8$ do not form any rings. That is, $R_1$ and $R_2$ may bind together to form the ring $A_1$, and $R_3$ and $R_4$ may bind together to form the ring $A_2$. As a result, the heterocyclic compound of Formula 1 above may have two aromatic or heteroaromatic rings. The ring $A_1$ and the ring $A_2$ may be identical to or different from each other, and may be each independently one of a substituted or unsubstituted $C_6$-$C_{30}$ aromatic ring or a substituted or unsubstituted $C_2$-$C_{30}$ heteroaromatic ring.

The other case is when $R_1$ to $R_4$ do not form any rings, while adjacent $R_5$ to $R_8$ groups bind together to form a ring $B_1$ and/or a ring $B_2$. For example, $R_7$ and $R_8$ may bind together to form the ring $B_1$, and $R_5$ and $R_6$ may bind together to form the ring $B_2$. As a result, the heterocyclic compound of Formula 1 above may also have two aromatic or heteroaromatic rings. The ring $B_1$ and the ring $B_2$ may be identical to or different from each other, and may be each independently one of a substituted or unsubstituted $C_6$-$C_{30}$ aromatic ring or a substituted or unsubstituted $C_2$-$C_{30}$ heteroaromatic ring.

In some embodiments, the heterocyclic compound of Formula 1 may be a compound represented by Formula 2a or 2b below.

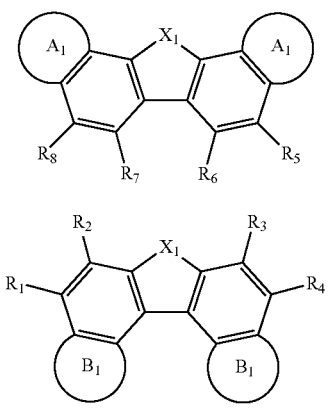

Formula 2a

Formula 2b

In Formula 2a above, $X_1$ is an oxygen atom (—O—) or a sulfur atom (—S—). The ring $A_1$ is one of a substituted or unsubstituted $C_6$-$C_{30}$ aromatic ring or a substituted or unsubstituted $C_2$-$C_{30}$ heteroaromatic ring.

$R_5$ to $R_8$ are each independently one of a hydrogen atom, a deuterium atom, a halogen atom, a hydroxyl group, a cyano group, an amino group, a nitro group, a carboxyl group, a substituted or unsubstituted $C_1$-$C_{30}$ alkyl group, a substituted or unsubstituted $C_2$-$C_{30}$ alkenyl group, a substituted or unsubstituted $C_2$-$C_{30}$ alkynyl group, a substituted or unsubstituted $C_1$-$C_{30}$ alkoxy group, a substituted or unsubstituted $C_3$-$C_{30}$ cycloalkyl group, a substituted or unsubstituted $C_3$-$C_{30}$ cycloalkenyl group, a substituted or unsubstituted $C_6$-$C_{30}$ aryl group, a substituted or unsubstituted $C_6$-$C_{30}$ aryloxy group, a substituted or unsubstituted $C_6$-$C_{30}$ arylthio group, a substituted or unsubstituted $C_2$-$C_{30}$ heteroaryl group, or a —N($Q_1$)($Q_2$) group in which $Q_1$ and $Q_2$ are as defined above with respect to Formula 1.

In Formula 2b above, $X_1$ is an oxygen atom (—O—) or a sulfur atom (—S—). The ring $B_1$ is one of a substituted or unsubstituted $C_6$-$C_{30}$ aromatic ring or a substituted or unsubstituted $C_2$-$C_{30}$ heteroaromatic ring.

$R_1$ to $R_4$ are each independently one of a hydrogen atom, a deuterium atom, a halogen atom, a hydroxyl group, a cyano group, an amino group, a nitro group, a carboxyl group, a substituted or unsubstituted $C_1$-$C_{30}$ alkyl group, a substituted or unsubstituted $C_2$-$C_{30}$ alkenyl group, a substituted or unsubstituted $C_2$-$C_{30}$ alkynyl group, a substituted or unsubstituted $C_1$-$C_{30}$ alkoxy group, a substituted or unsubstituted $C_3$-$C_{30}$ cycloalkyl group, a substituted or unsubstituted $C_3$-$C_{30}$ cycloalkenyl group, a substituted or unsubstituted $C_6$-$C_{30}$ aryl group, a substituted or unsubstituted $C_6$-$C_{30}$ aryloxy group, a substituted or unsubstituted $C_6$-$C_{30}$ arylthio group, a substituted or unsubstituted $C_2$-$C_{30}$ heteroaryl group, or a —N($Q_1$)($Q_2$) group.

The heterocyclic compound of Formula 2a has a left-right symmetric backbone structure in which the ring $A_1$ is fused to dibenzofuran or dibenzothiophene. The heterocyclic compound of Formula 2b also has a left-right symmetric backbone structure in which the ring $B_1$ is fused to dibenzofuran or dibenzothiophene.

For example, the heterocyclic compound of Formula 2a may have a left-right symmetric structure as a whole because $R_5$ to $R_8$ are symmetrical to one another. The heterocyclic compound of Formula 2b may have a left-right symmetric structure as a whole because $R_1$ to $R_4$ are symmetrical to one another.

In Formula 2a of the heterocyclic compound, the ring $A_1$ may be one of a substituted or unsubstituted benzene ring, a substituted or unsubstituted anthracene ring, a substituted or unsubstituted phenanthrene ring, a substituted or unsubstituted fluorene ring, a substituted or unsubstituted pyridine ring, a substituted or unsubstituted carbazole ring, a substituted or unsubstituted thiophene ring, a substituted or unsubstituted dibenzothiophene ring, or a substituted or unsubstituted dibenzofuran ring. In Formula 2b of the heterocyclic compound, the ring $B_1$ may also be selected from the groups listed above in connection with the ring $A_1$.

In some embodiments, in the heterocyclic compound Formula 2a or 2b, the ring $A_1$ and the ring $B_1$ may each independently be one of the groups represented by one of Formulae 3a to 3f below.

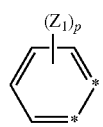

Formula 3a

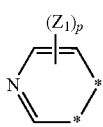

Formula 3b

Formula 3c

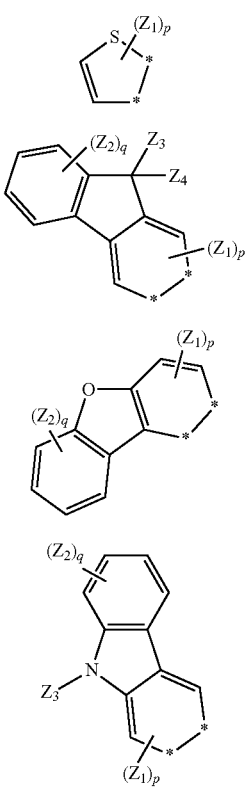

Formula 3d

Formula 3e

Formula 3f

Formula 4a

Formula 4b

Formula 4c

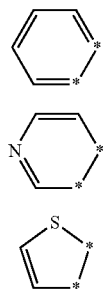

Formula 4d

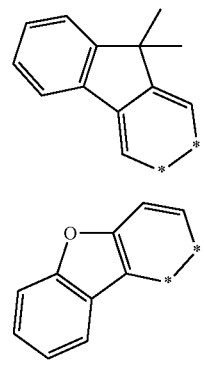

Formula 4e

Formula 4f

In Formulae 3a to 3f, $Z_1$ to $Z_4$ may be each independently one of a hydrogen atom, a deuterium atom, a halogen atom, a cyano group, a substituted or unsubstituted methyl group, a substituted or unsubstituted ethyl group, a substituted or unsubstituted propyl group, a substituted or unsubstituted butyl group, a substituted or unsubstituted phenyl group, or a substituted or unsubstituted biphenyl group. Each of p and q may be independently an integer from 2 to 4. In some embodiments, $Z_1$ to $Z_4$ may be each independently a hydrogen atom or a phenyl group.

* indicates a binding site of the ring $A_1$ or ring $B_1$ with the rest of the heterocyclic compound, i.e., a moiety excluding the ring $A_1$ or ring $B_1$. That is, the ring $A_1$ or ring $B_1$ is fused at the sites with two *s.

In some other embodiments, in the heterocyclic compound Formula 2a or 2b, the ring $A_1$ and the ring $B_1$ may each independently be one of the groups represented by one of Formulae 4a to 4f below.

As in Formulae 3a-3f, in Formulae 4a-4f, * indicates a binding site of the ring $A_1$ or ring $B_1$ with the rest of the heterocyclic compound, i.e., a moiety excluding the ring $A_1$ or ring $B_1$.

In Formula 2a or 2b of the heterocyclic compound, $R_1$ to $R_8$ may be each independently one of a hydrogen atom, a deuterium atom, a halogen atom, a cyano group, a substituted or unsubstituted methyl group, a substituted or unsubstituted ethyl group, a substituted or unsubstituted propyl group, a substituted or unsubstituted butyl group, a substituted or unsubstituted phenyl group, a substituted or unsubstituted biphenyl group, a substituted or unsubstituted naphthyl group, a substituted or unsubstituted anthryl group, a substituted or unsubstituted phenanthrenyl group, a substituted or unsubstituted pyrenyl group, a substituted or unsubstituted chrysenyl group, a substituted or unsubstituted naphthacenyl group, a substituted or unsubstituted fluorenyl group, a substituted or unsubstituted pyridinyl group, a substituted or unsubstituted bipyridinyl group, a substituted or unsubstituted pyrazinyl group, a substituted or unsubstituted pyrimidinyl group, a substituted or unsubstituted pyridazinyl group, a substituted or unsubstituted carbazolyl group, a substituted or unsubstituted benzothiophenyl group, a substituted or unsubstituted dibenzothiophenyl group, a substituted or unsubstituted dibenzofuranyl group, or a group represented by -ph-N($Q_3$)($Q_4$).

The group represented by -ph-N($Q_3$)($Q_4$) may be a monovalent group of -(phenylene)-(amine derivative), where $Q_3$ and $Q_4$ may be each independently one of a hydrogen atom, a deuterium atom, a halogen atom, a hydroxyl group, a cyano group, an amino group, a nitro group, a carboxyl group, a substituted or unsubstituted $C_1$-$C_{30}$ alkyl group, a substituted or unsubstituted $C_2$-$C_{30}$ alkenyl group, a substituted or unsubstituted $C_2$-$C_{30}$ alkynyl group, a substituted or unsubstituted $C_1$-$C_{30}$ alkoxy group, a substituted or unsubstituted $C_3$-$C_{30}$ cycloalkyl group, a substituted or unsubstituted $C_3$-$C_{30}$ cycloalkenyl group, a substituted or unsubstituted $C_6$-$C_{30}$ aryl group, a substituted or unsubstituted $C_6$-$C_{30}$ aryloxy group, a substituted or unsubstituted $C_6$-$C_{30}$ arylthio group, or a substituted or unsubstituted $C_2$-$C_{30}$ heteroaryl group.

In Formula 2a of the heterocyclic compound, $R_5$ and $R_8$ may be each independently one of a substituted or unsubstituted phenyl group, a substituted or unsubstituted biphenyl group, a substituted or unsubstituted fluorenyl group, a substituted or unsubstituted pyridinyl group, a substituted or unsubstituted carbazolyl group, a substituted or unsubstituted benzothiophenyl group, a substituted or unsubstituted dibenzothiophenyl group, a substituted or unsubstituted dibenzofuranyl group, or a group represented by -ph-N(ph)(ph). $R_6$ and $R_7$ may be each independently a hydrogen atom or a deuterium atom.

In Formula 2b of the heterocyclic compound, $R_1$ and $R_4$ may be each independently one of a substituted or unsubstituted phenyl group, a substituted or unsubstituted biphenyl group, a substituted or unsubstituted fluorenyl group, a substituted or unsubstituted pyridinyl group, a substituted or unsubstituted carbazolyl group, a substituted or unsubstituted benzothiophenyl group, a substituted or unsubstituted dibenzothiophenyl group, a substituted or unsubstituted dibenzofuranyl group, or a group represented by -ph-N(ph)(ph). $R_2$ and $R_3$ may be each independently a hydrogen atom or a deuterium atom.

In some embodiments, in Formula 2a or 2b of the heterocyclic compound, $R_2$, $R_3$, $R_6$ and $R_7$ may be each independently a hydrogen atom or a deuterium atom; and $R_1$, $R_4$, $R_5$ and $R_8$ may be each independently one of the groups represented by one of Formulae 5a to 5g below.

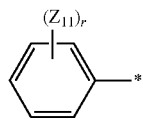

Formula 5a

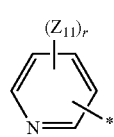

Formula 5b

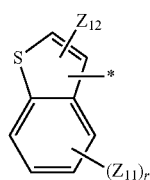

Formula 5c

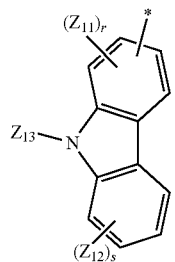

Formula 5d

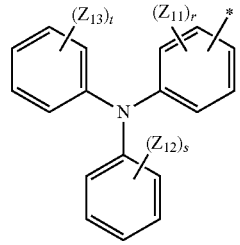

Formula 5e

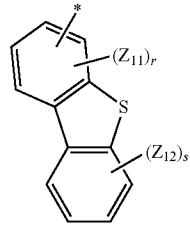

Formula 5f

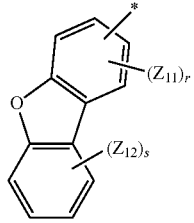

Formula 5g

In Formulae 5a to 5g above, $Z_{11}$ and $Z_{13}$ may be each independently one of a hydrogen atom, a deuterium atom, a halogen atom, a cyano group, a substituted or unsubstituted methyl group, a substituted or unsubstituted ethyl group, a substituted or unsubstituted propyl group, a substituted or unsubstituted butyl group, a substituted or unsubstituted methoxy group, a substituted or unsubstituted ethoxy group, a substituted or unsubstituted propoxy group, a substituted or unsubstituted butoxy group, a substituted or unsubstituted phenyl group, or a substituted or unsubstituted biphenyl group. Each of r, s and t may be independently an integer from 1 to 5. In some embodiments, $Z_{11}$ to $Z_{13}$ may be each independently a methoxy group or a phenyl group.

* indicates a binding site of $R_1$, $R_4$, $R_5$ or $R_8$ with the rest of the heterocyclic compound, i.e., a moiety excluding $R_1$, $R_4$, $R_5$ or $R_8$.

In some embodiments, in Formula 2a or 2b of the heterocyclic compound, $R_2$, $R_3$, $R_6$ and $R_7$ may be each independently a hydrogen atom or a deuterium atom; and $R_1$, $R_4$, $R_5$ and $R_8$ may be each independently one of the groups represented by one of Formulae 6a to 6g below.

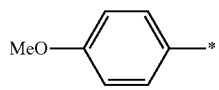

Formula 6a

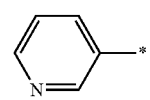

Formula 6b

-continued
Formula 6c
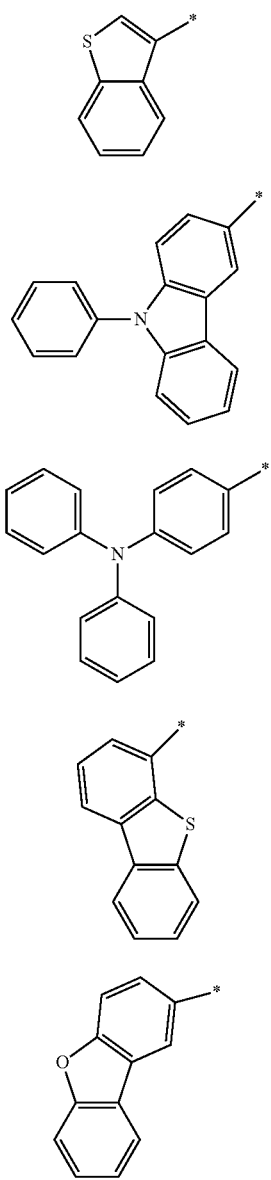
Formula 6d
Formula 6e
Formula 6f
Formula 6g
As in Formulae 5a-5g, in Formulae 6a-6g, * indicates a binding site of $R_1$, $R_4$, $R_5$ or $R_8$ with the rest of the heterocyclic compound, i.e., a moiety excluding $R_1$, $R_4$, $R_5$ or $R_8$.
The heterocyclic compound of Formula 1 may be one of Compounds 1 to 168 below, but is not limited thereto.
1
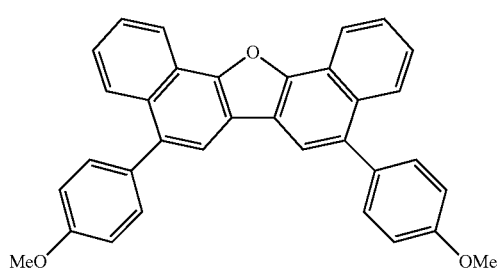
-continued
2
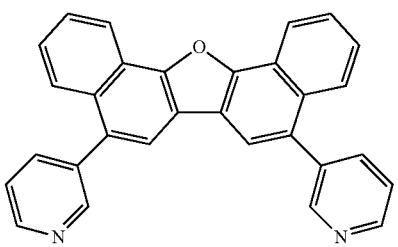
3
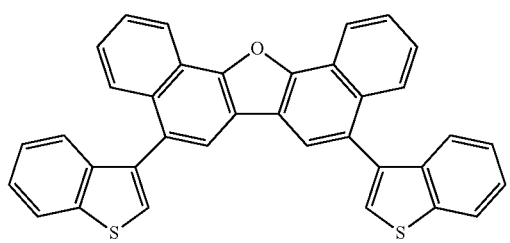
4
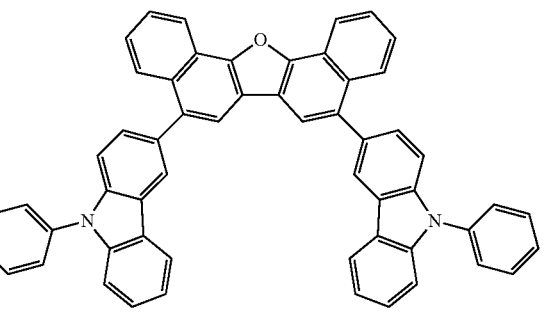
5
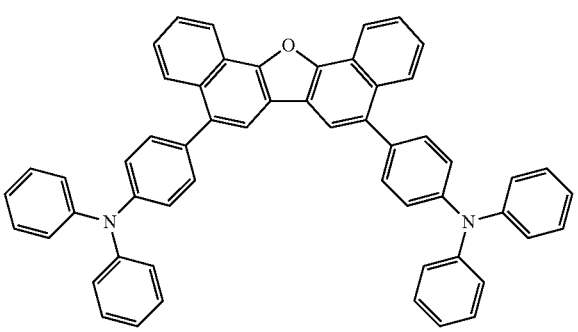
6
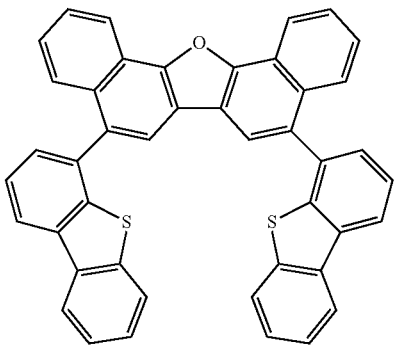

7
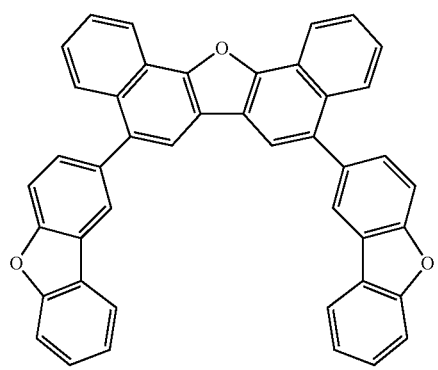
12
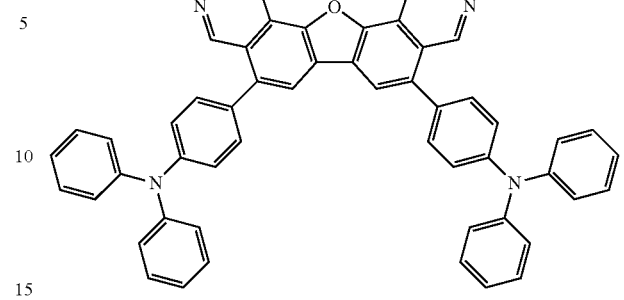
8
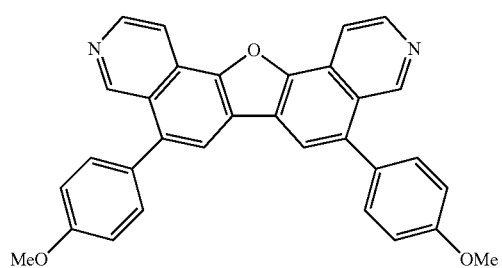
13
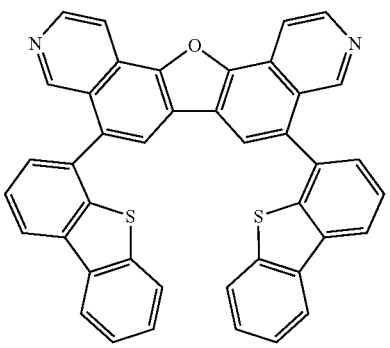
9
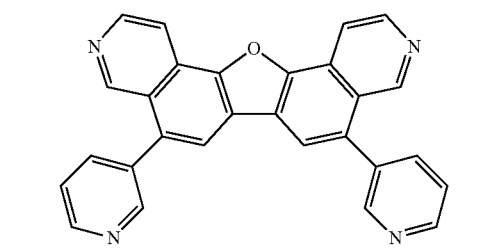
14
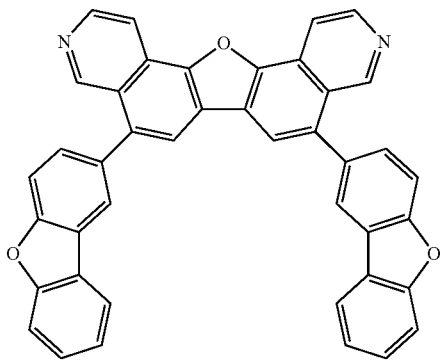
10
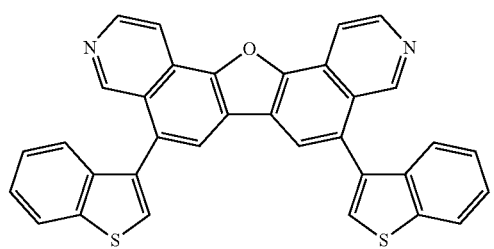
15
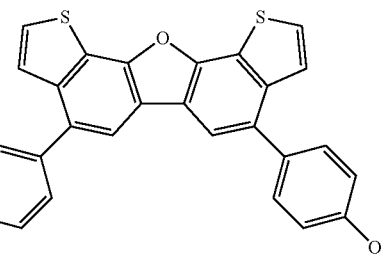
11
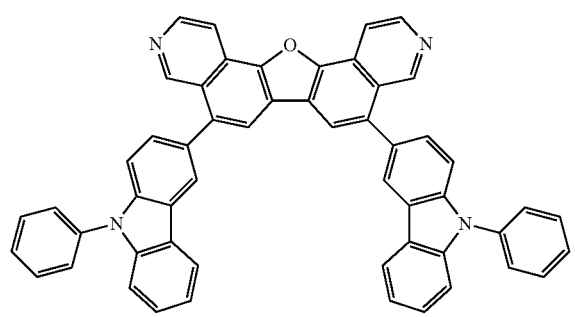
16
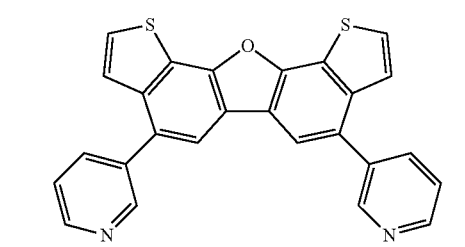

-continued
17
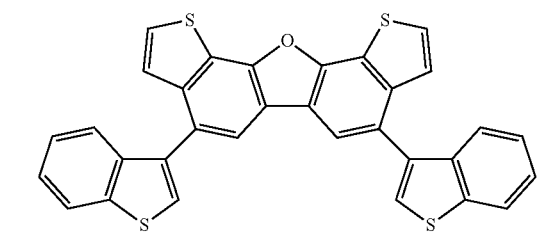
18
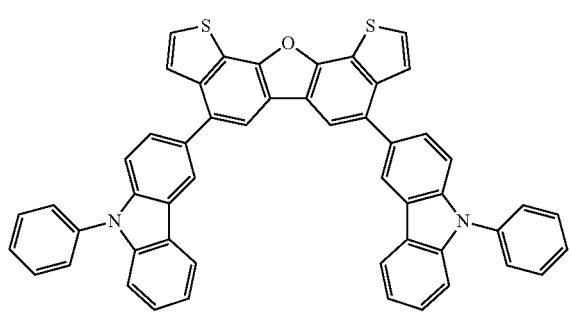
19
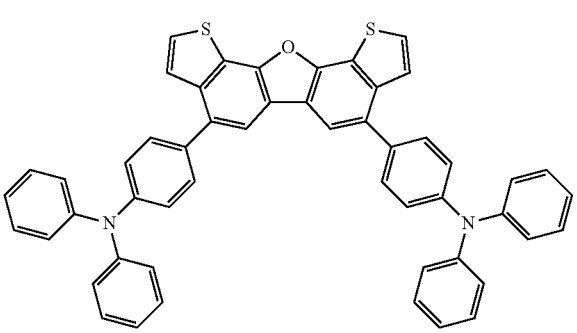
20
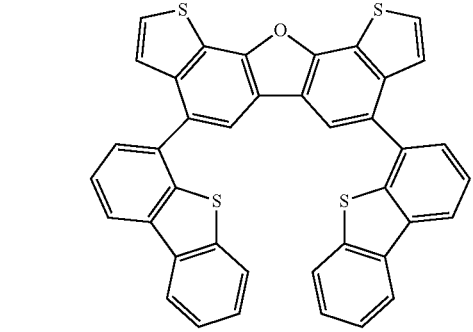
21
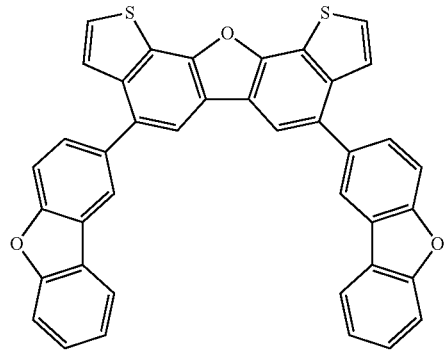
-continued
22
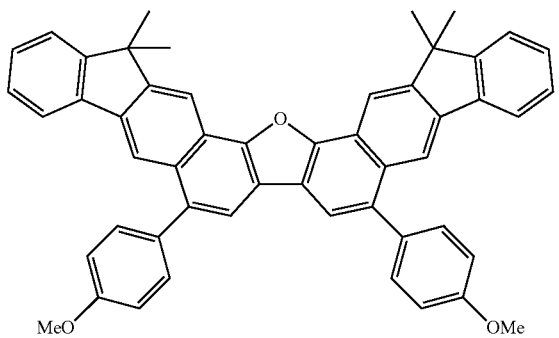
23
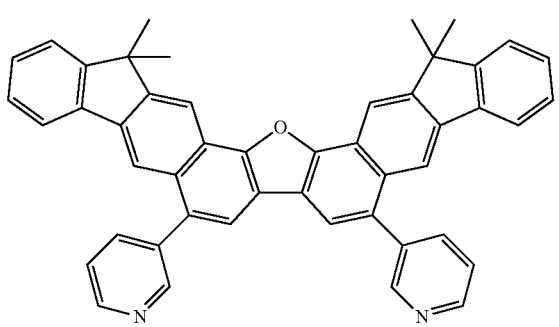
24
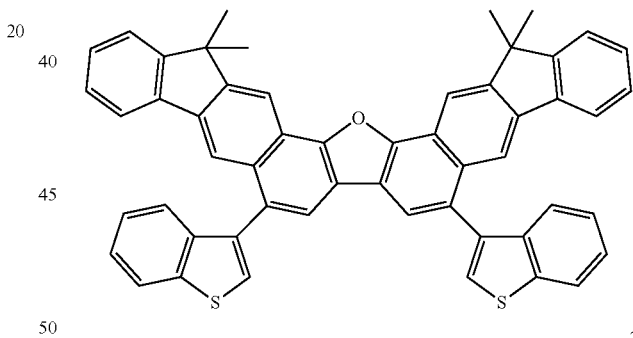
25
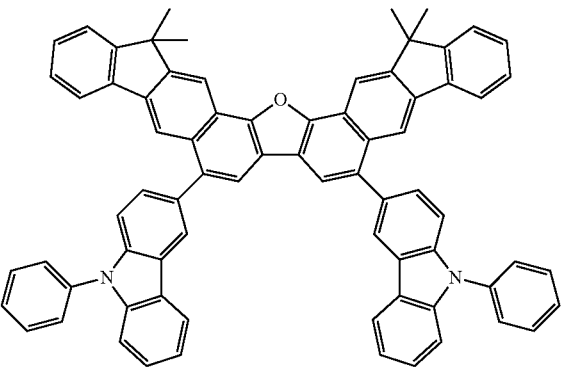

26
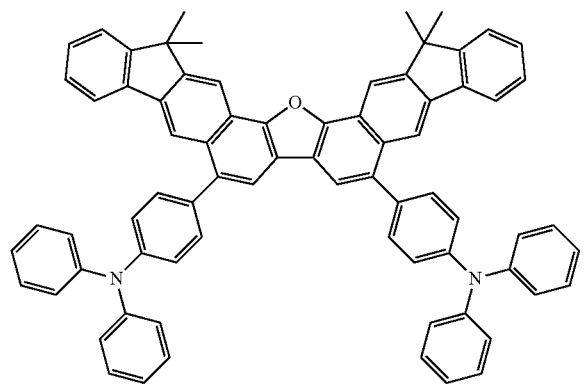
27
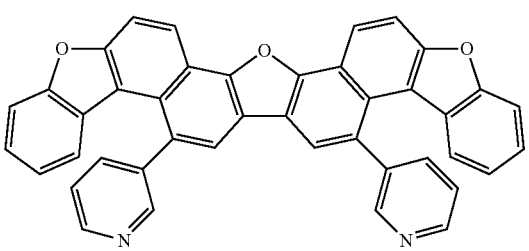
28
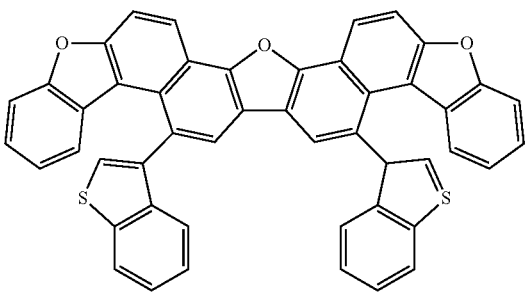
29
30
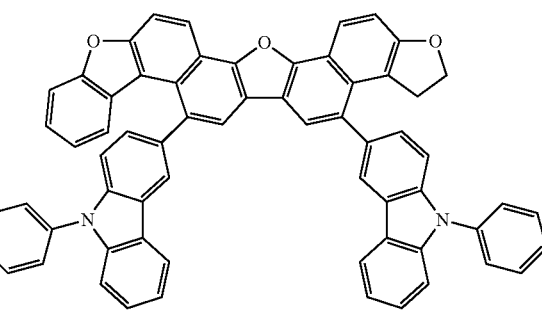
31
32
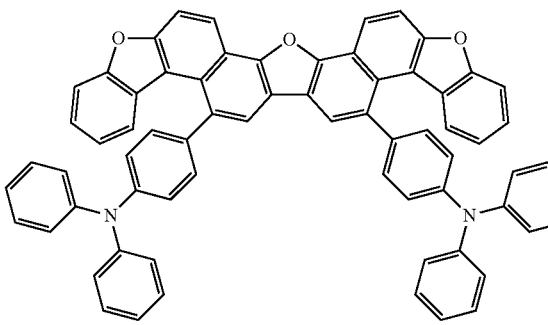
33
34
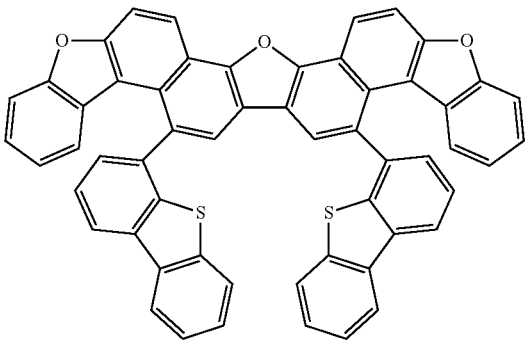

35
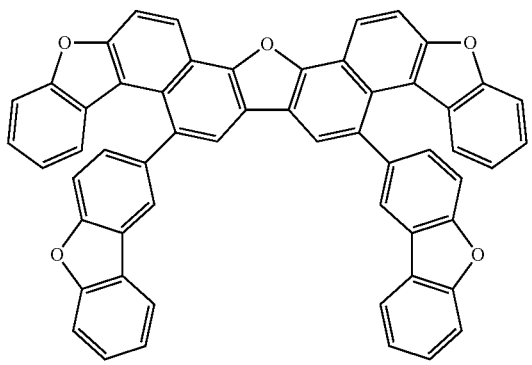
36
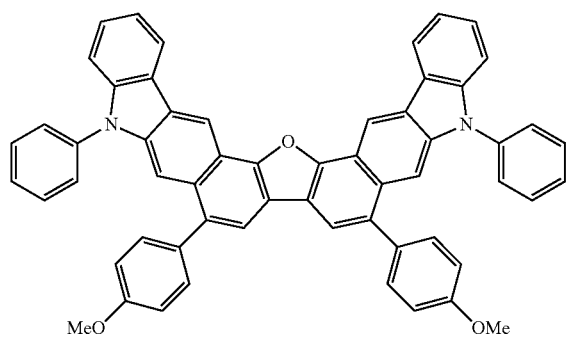
37
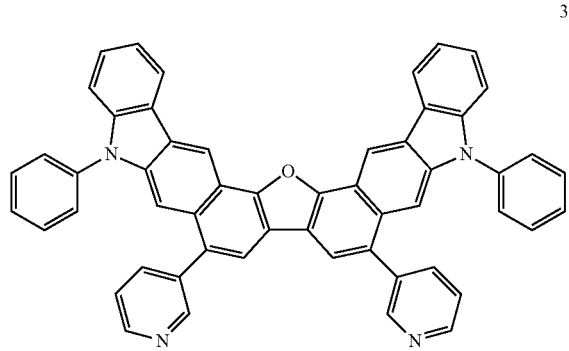
38
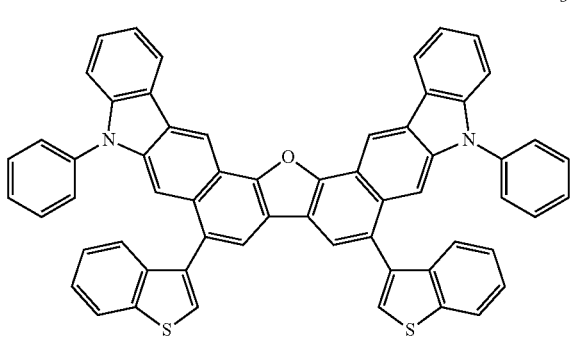
39
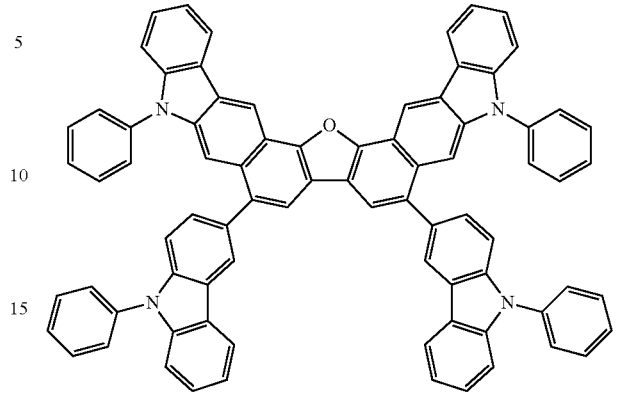
40
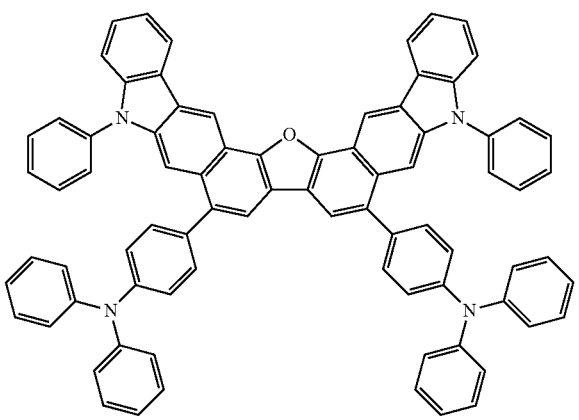
41
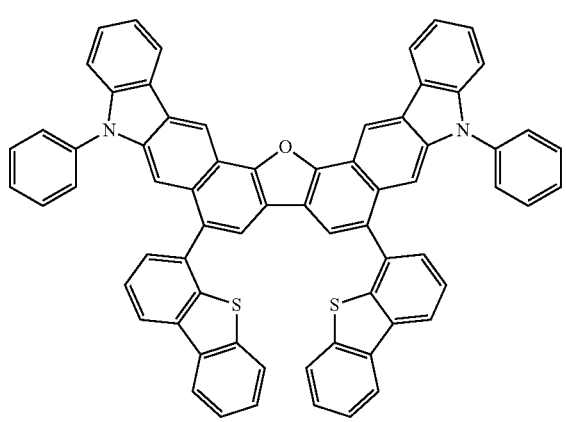

42
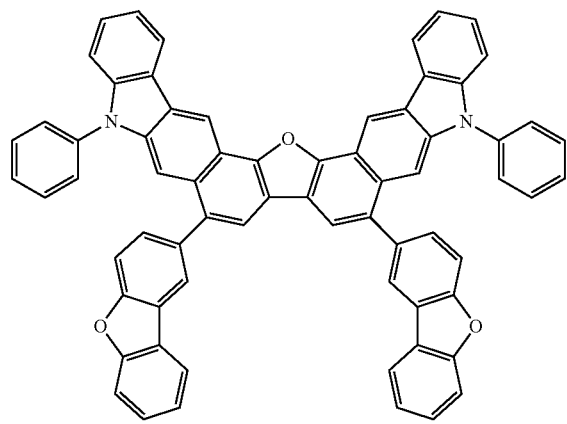
43
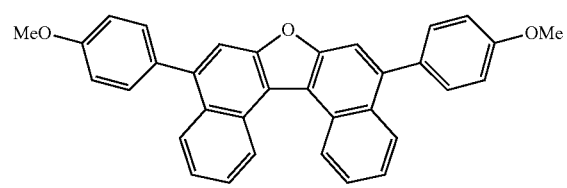
44
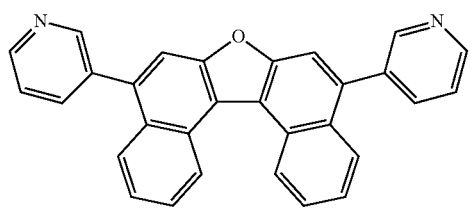
45
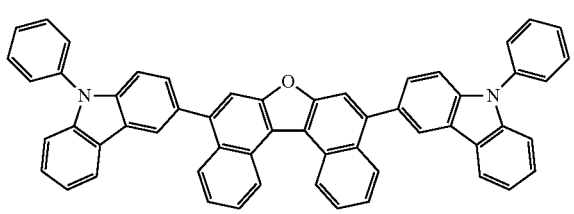
46
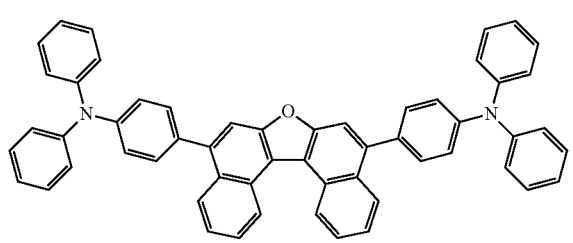
47
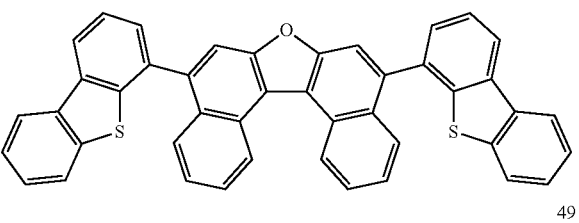
48
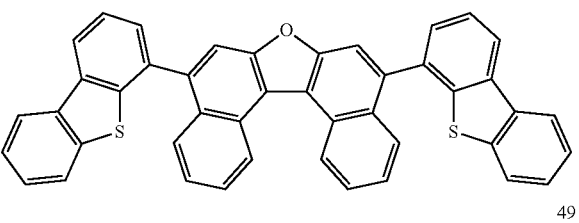
49
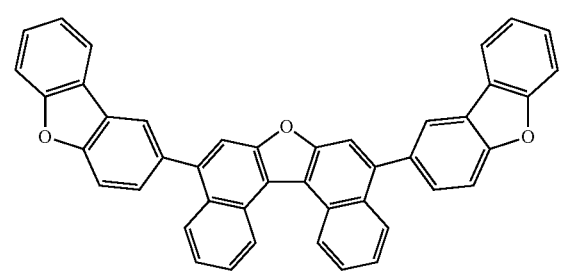
50
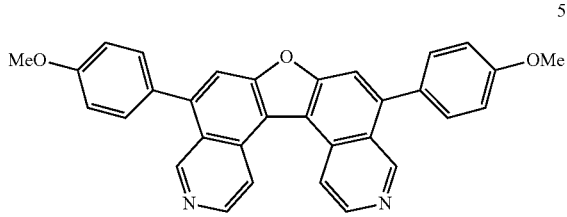
51
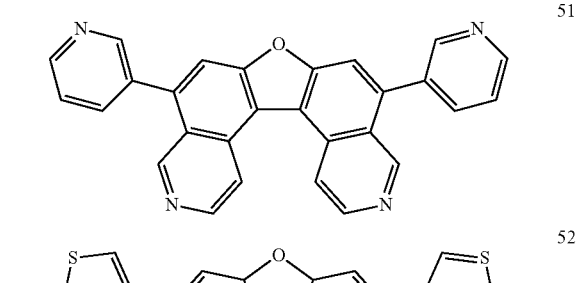
52
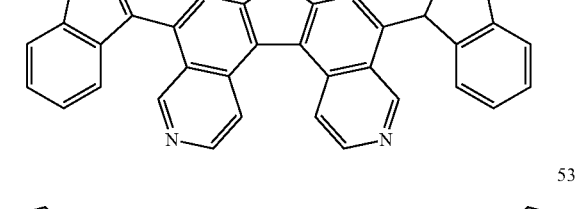
53
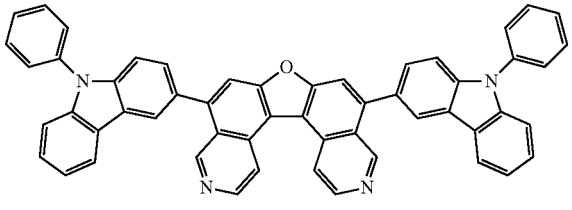
54
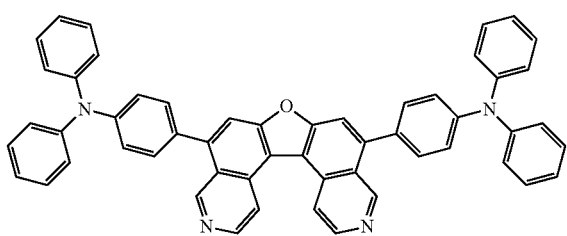

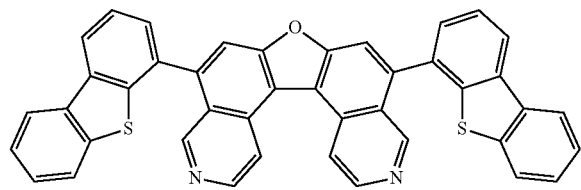
55
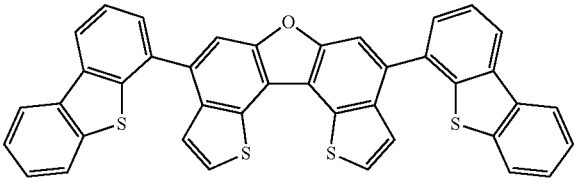
62
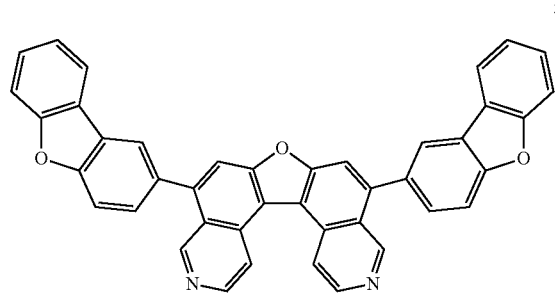
56
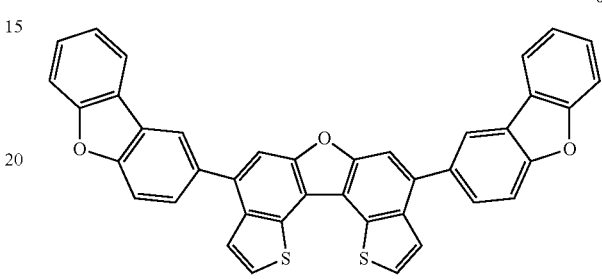
63
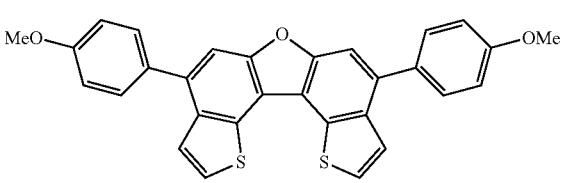
57
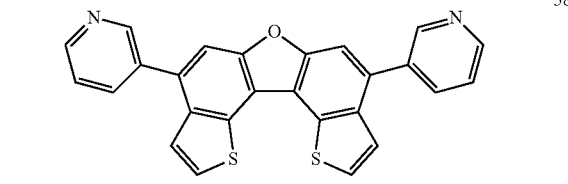
58
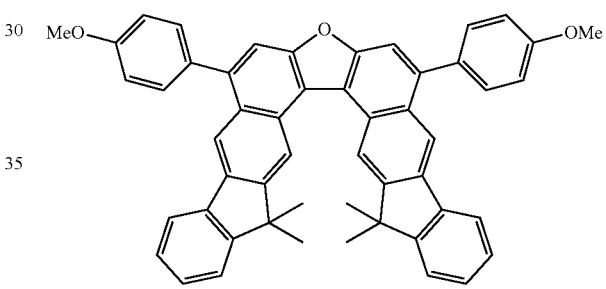
64
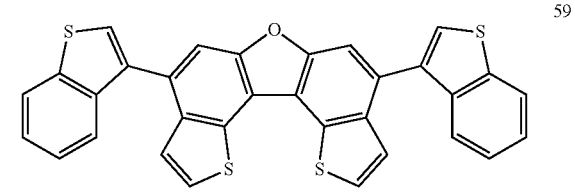
59
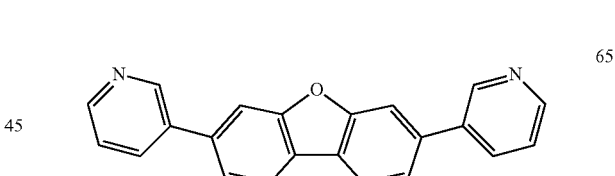
65
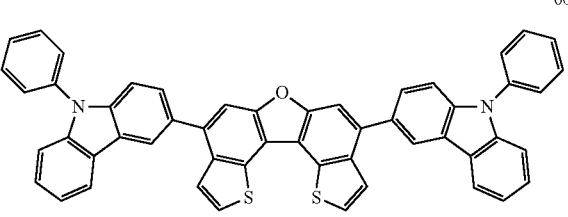
60
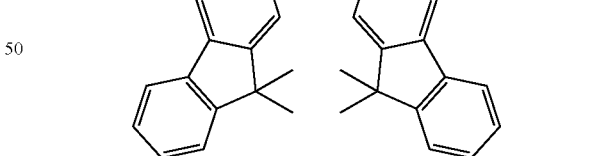
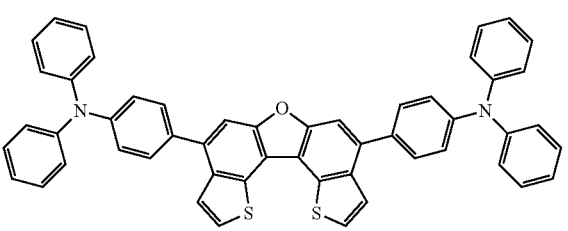
61
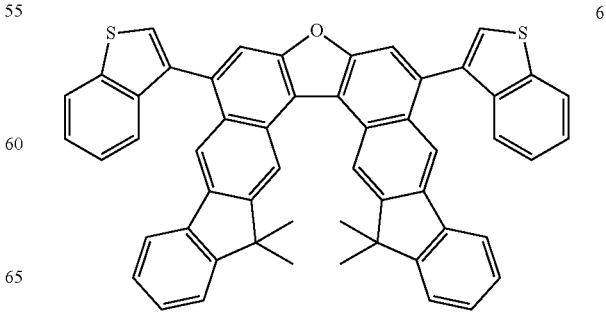
66

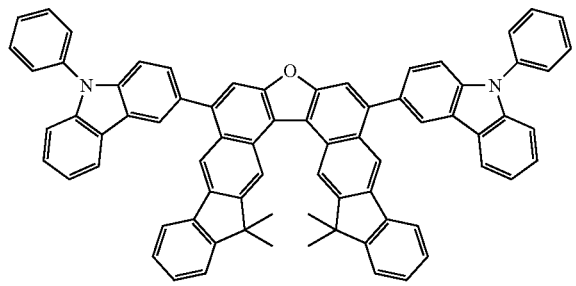
67
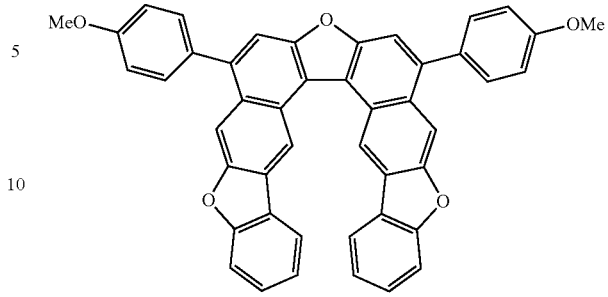
71
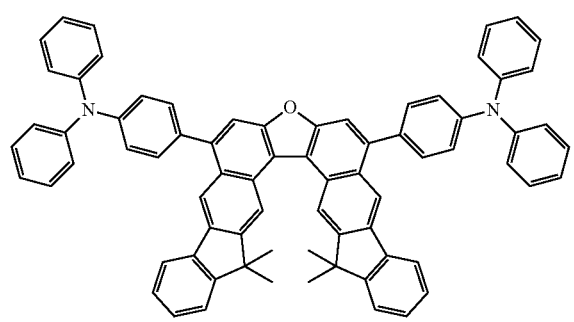
68
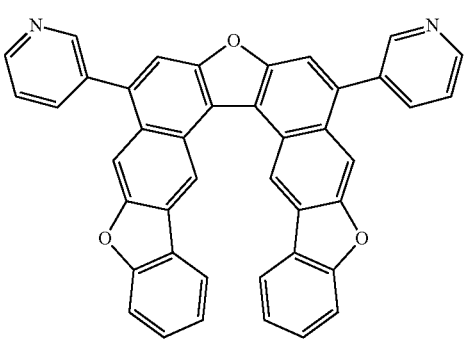
72
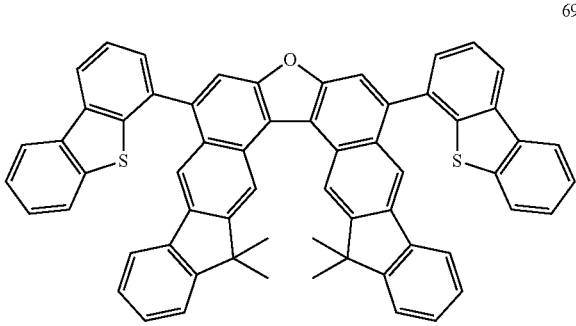
69
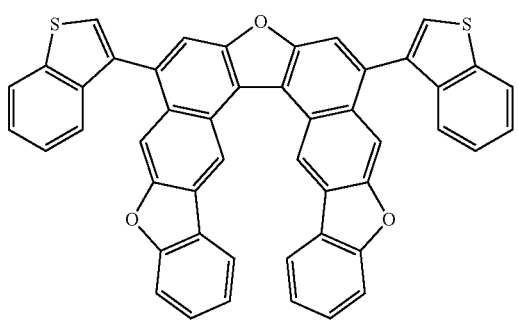
73
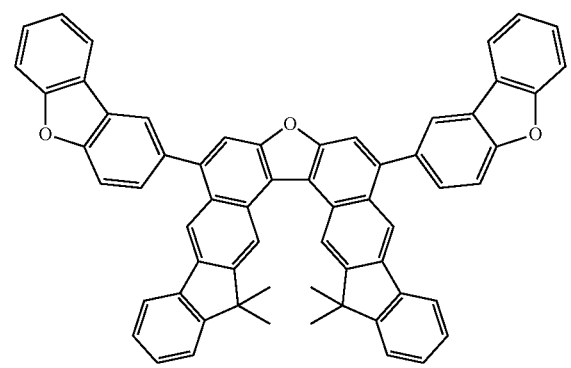
70
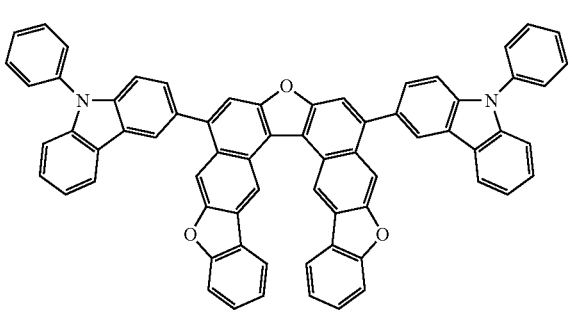
74

75
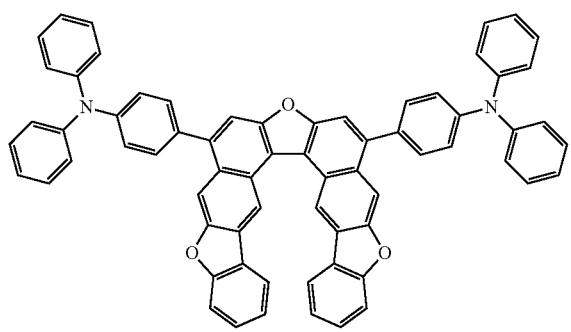
76
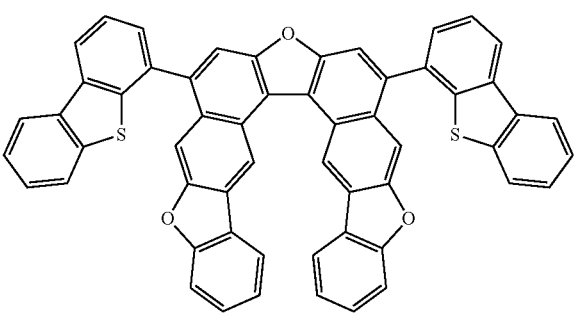
77
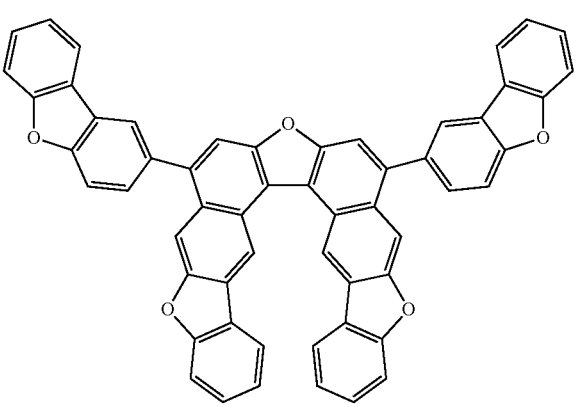
78
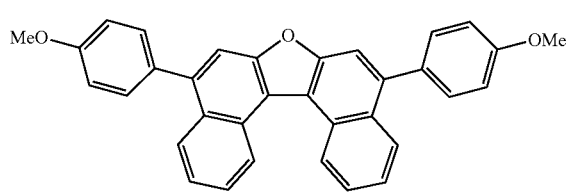
79
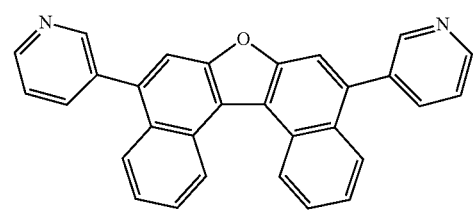
80
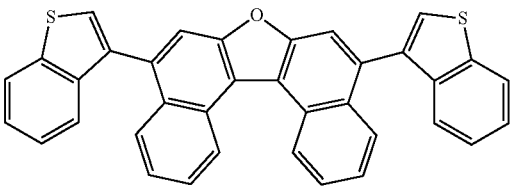
81
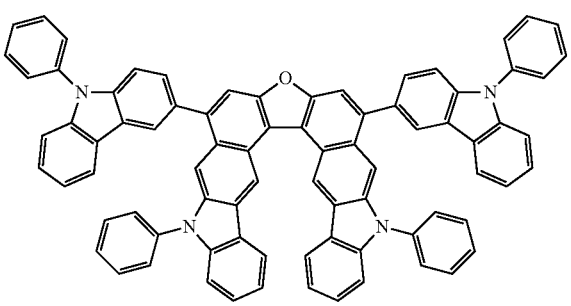
82
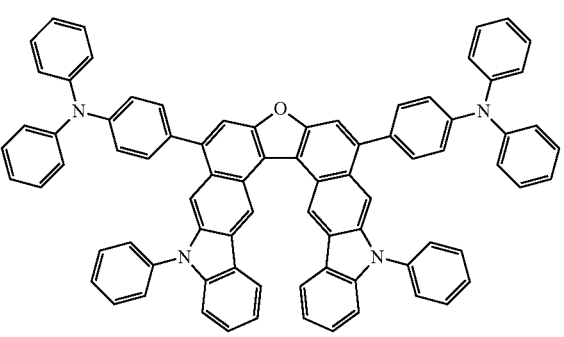
83
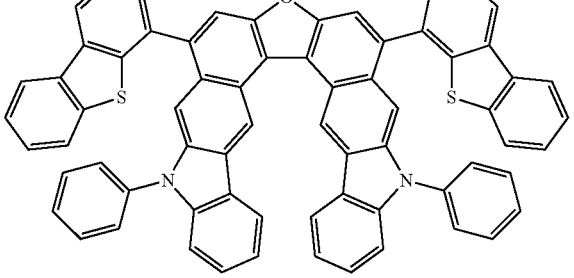
84
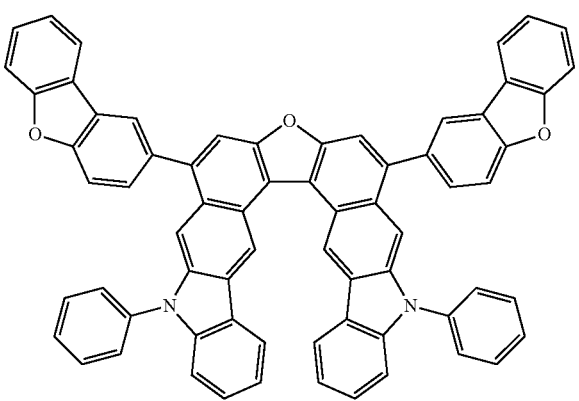

85
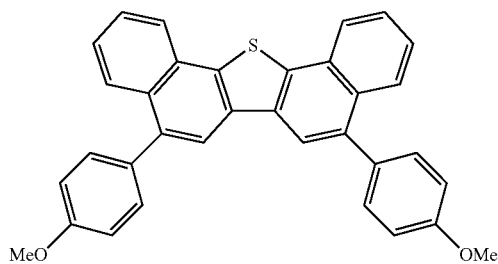
86
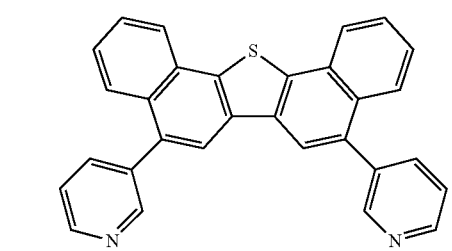
87
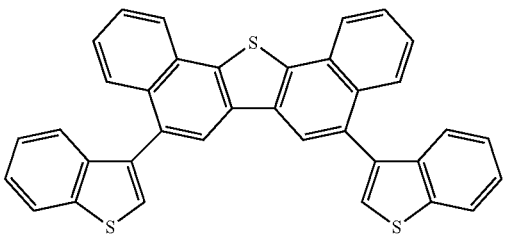
88
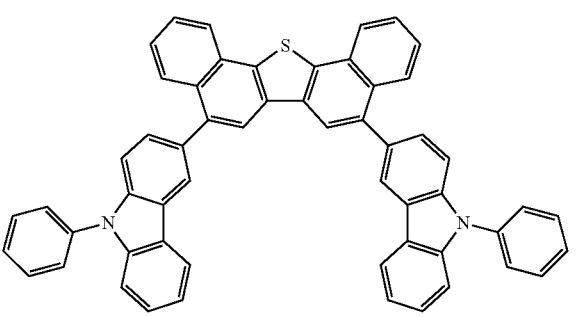
89
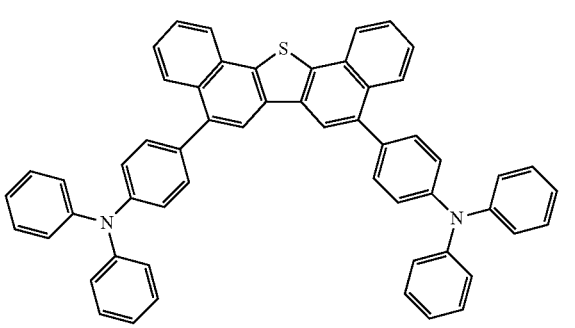
90
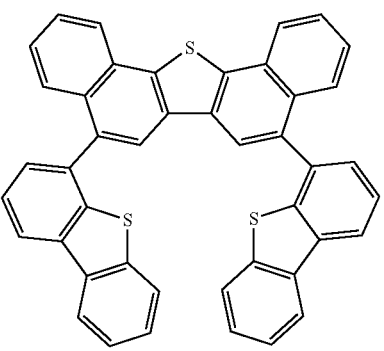
91
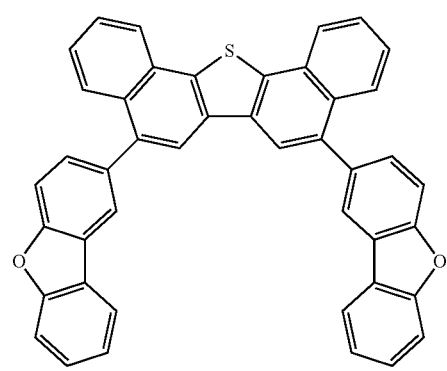
92
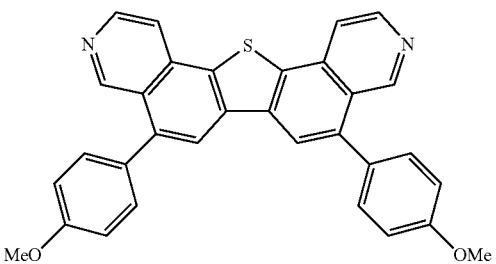
93
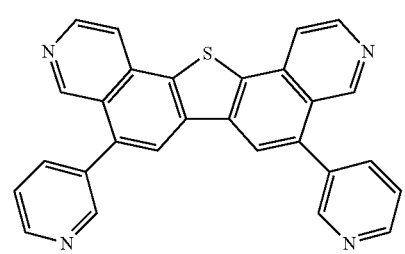
94
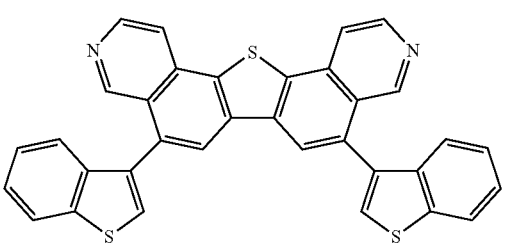

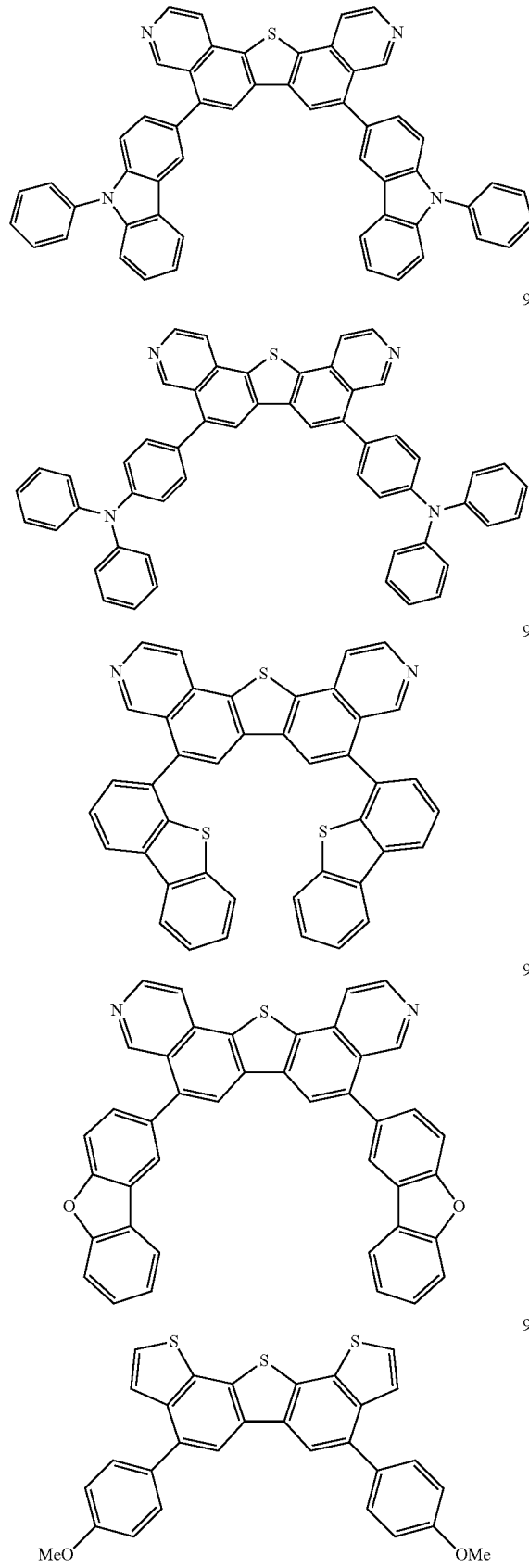
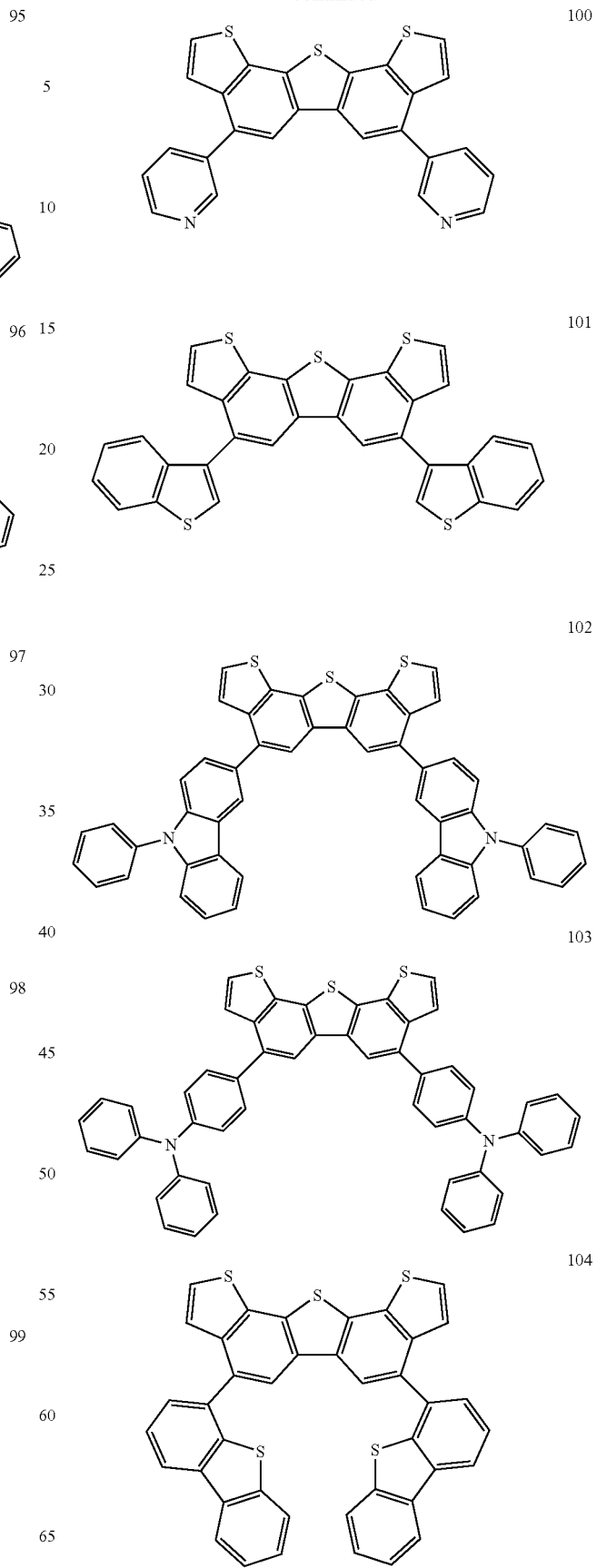

-continued
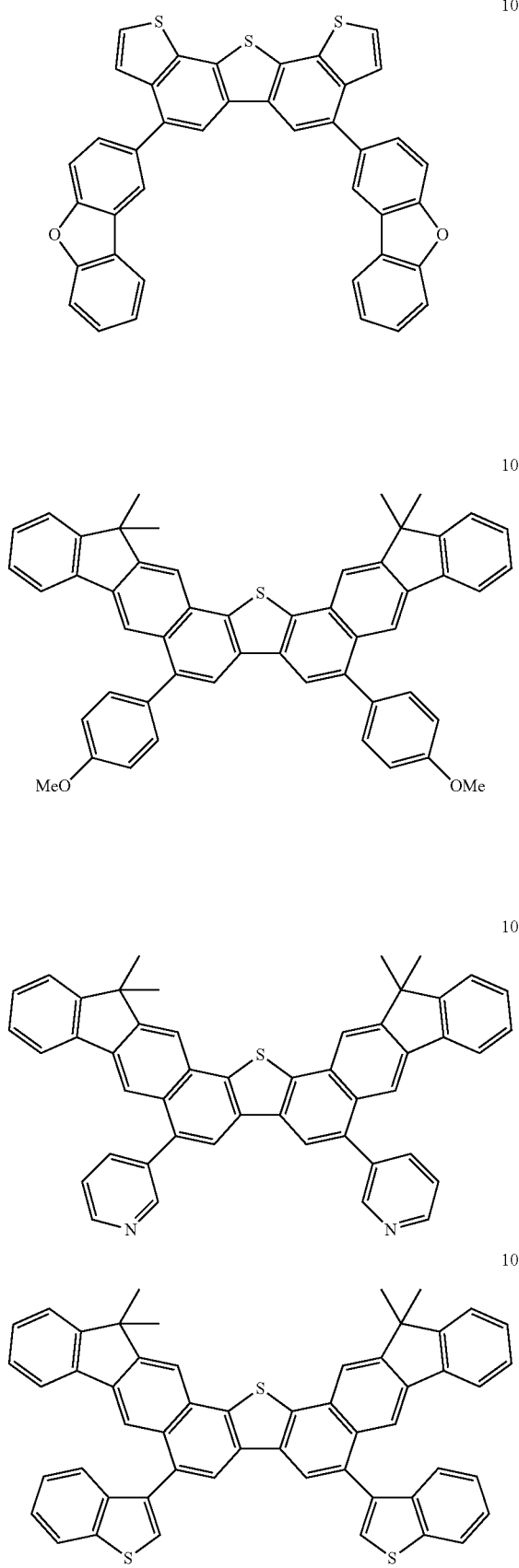
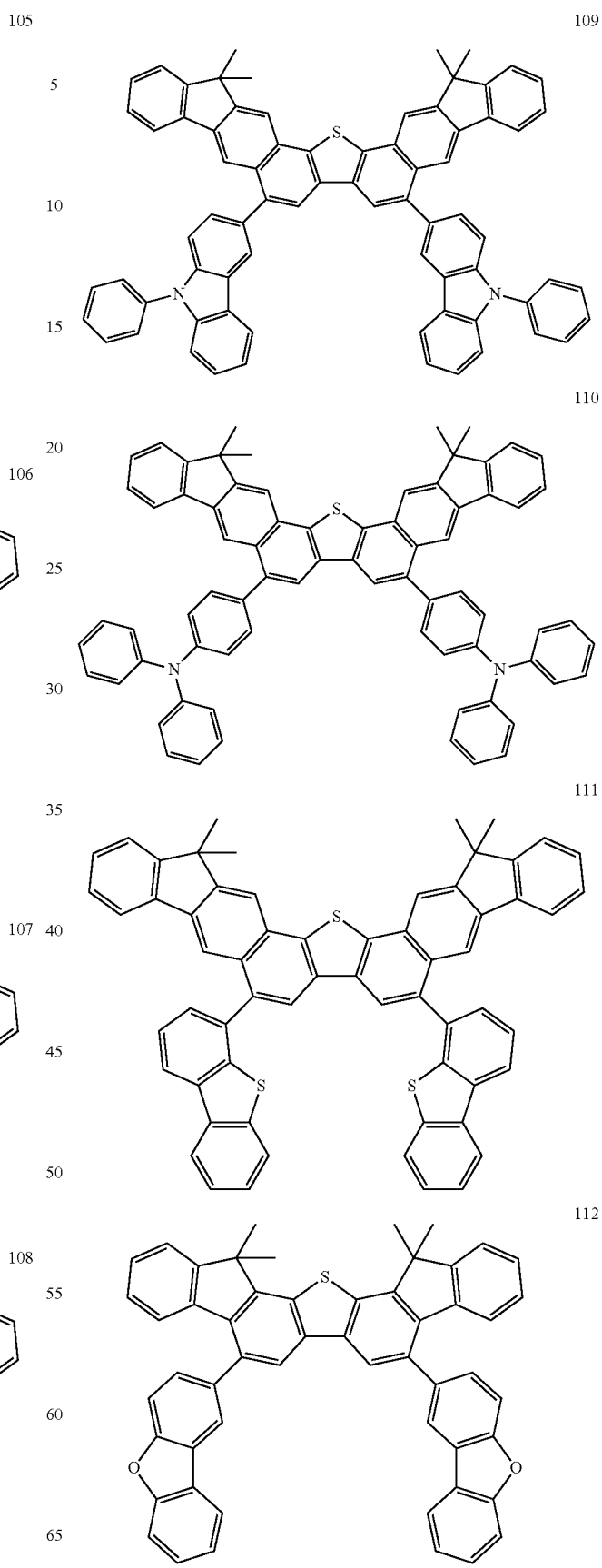

35
-continued
113
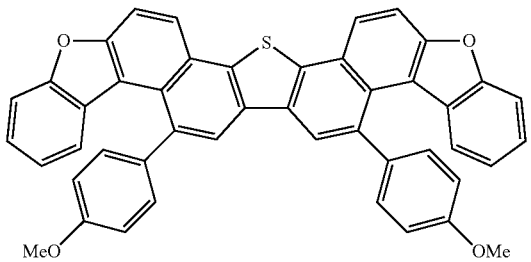
114
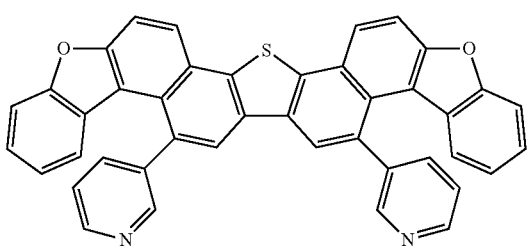
115
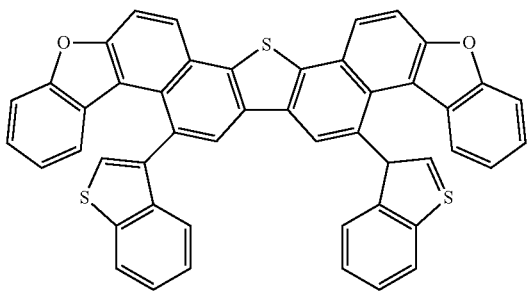
116
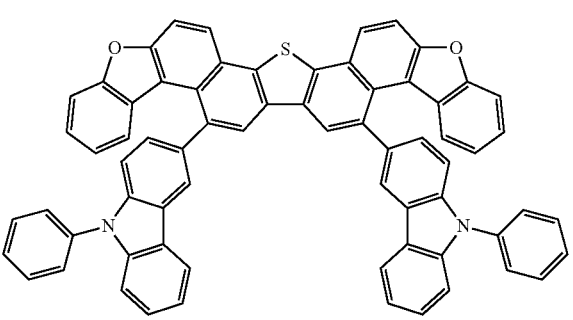
117
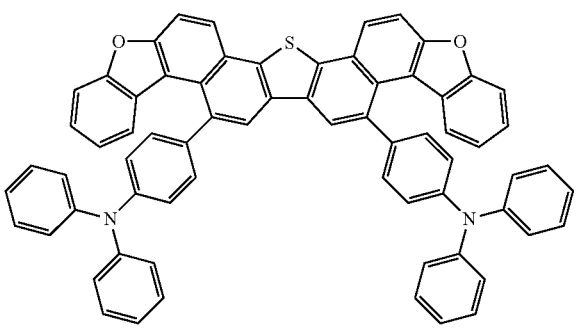
36
-continued
118
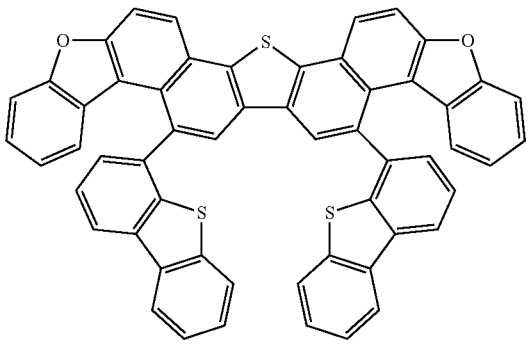
119
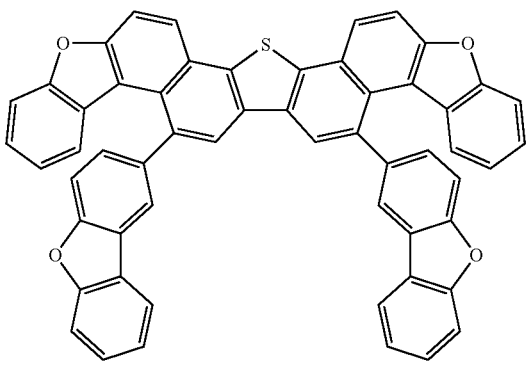
120
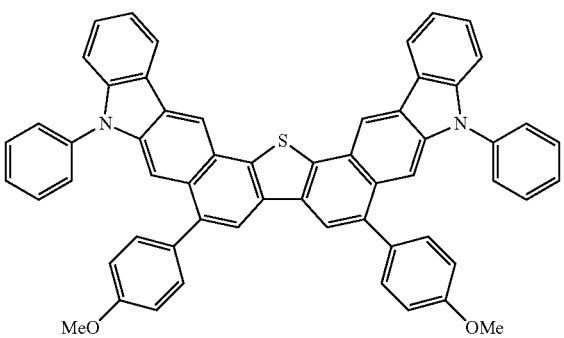
121
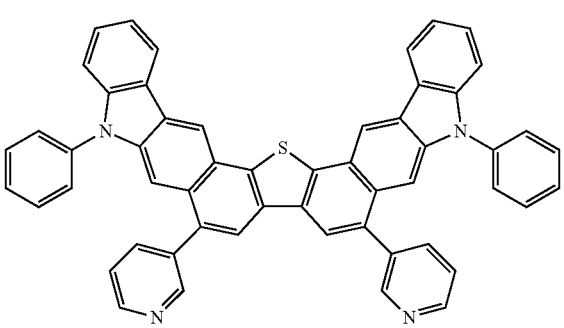

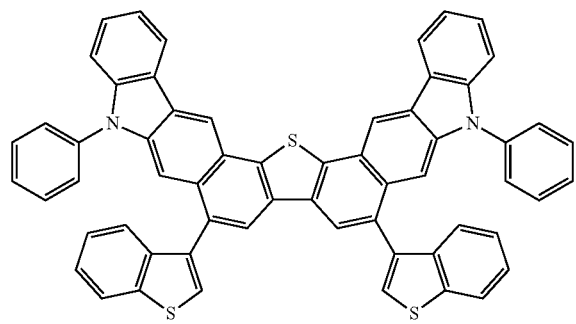
122
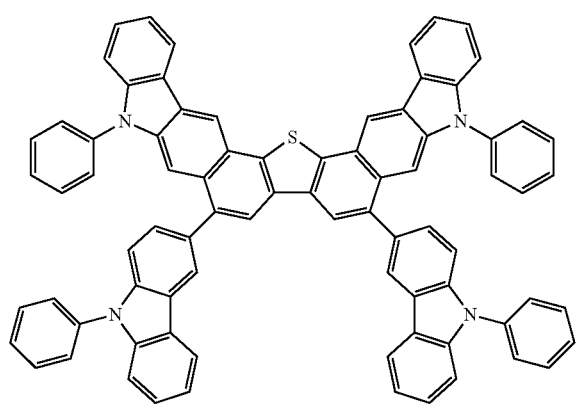
123
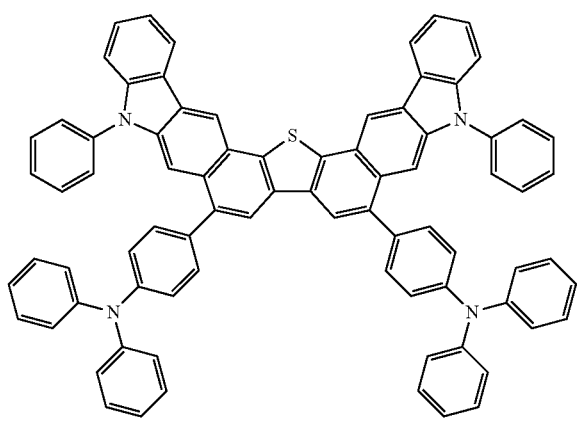
124
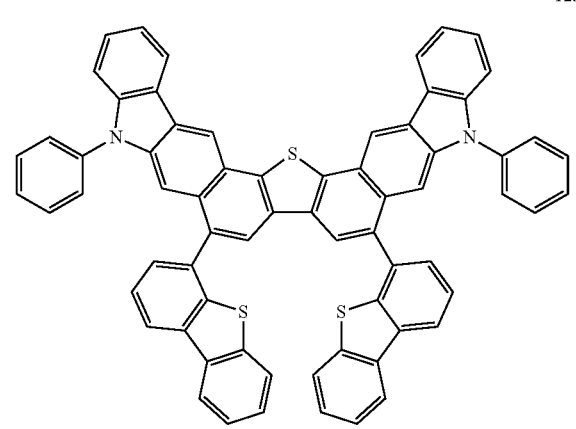
125
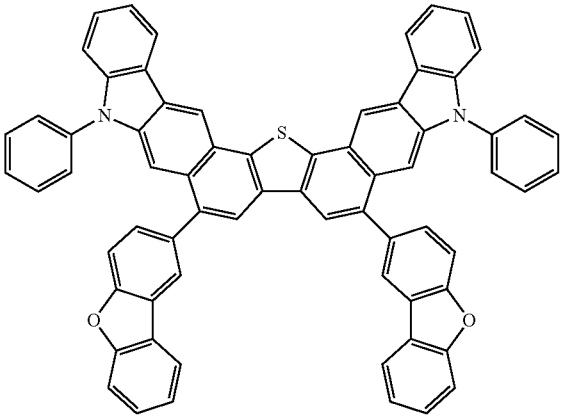
126
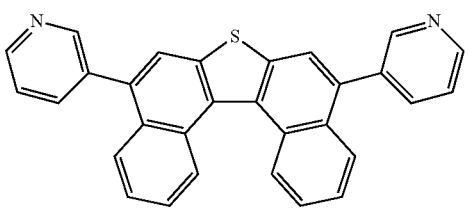
127
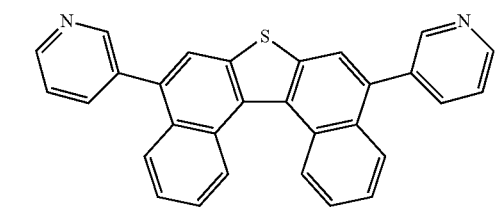
128
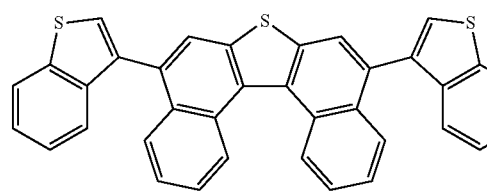
129
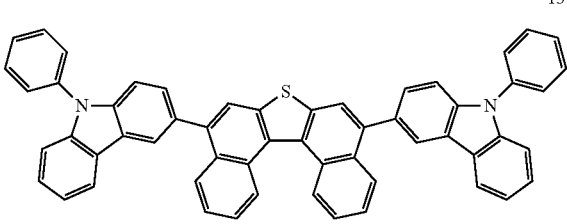
130
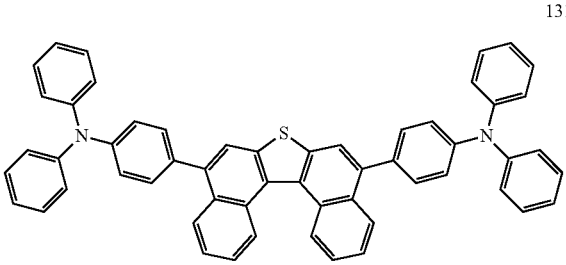
131

132
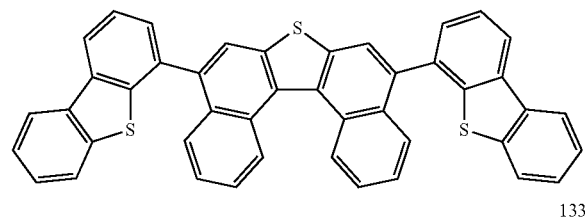
133
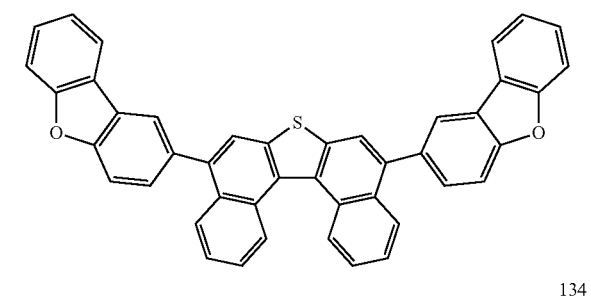
134
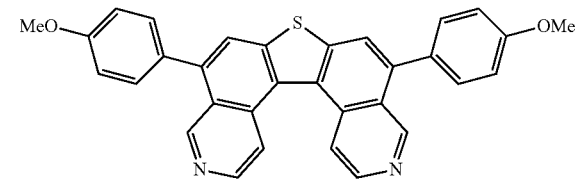
135
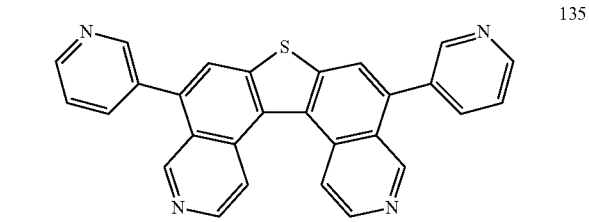
136
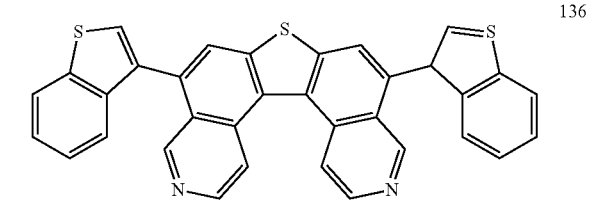
137
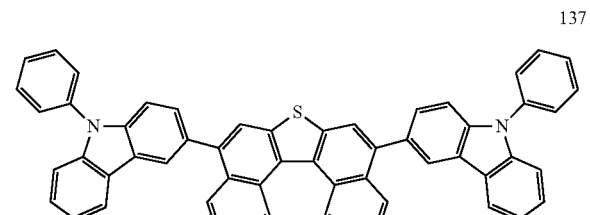
138
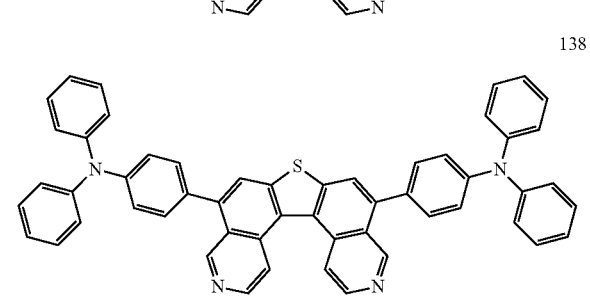
139
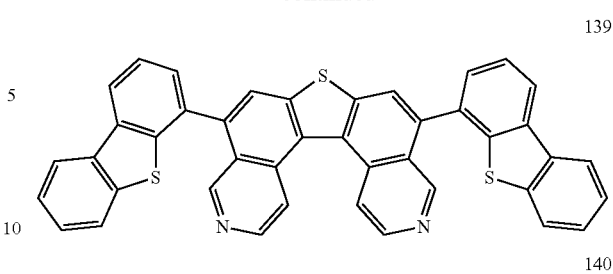
140
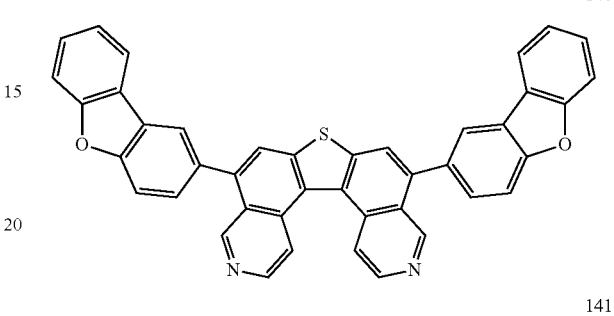
141
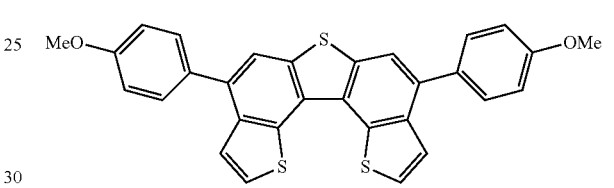
142
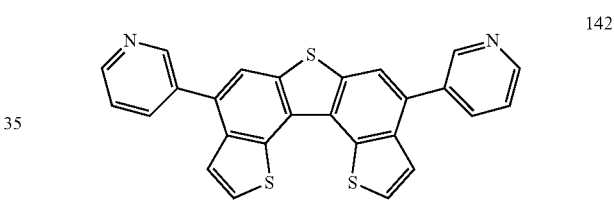
143
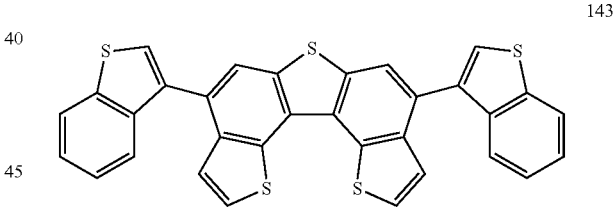
144
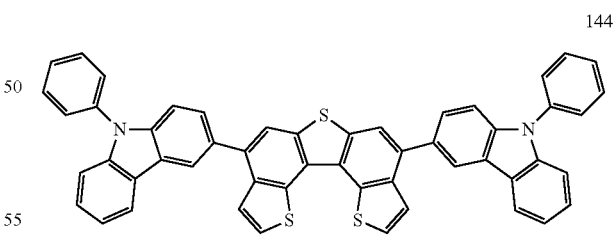
145
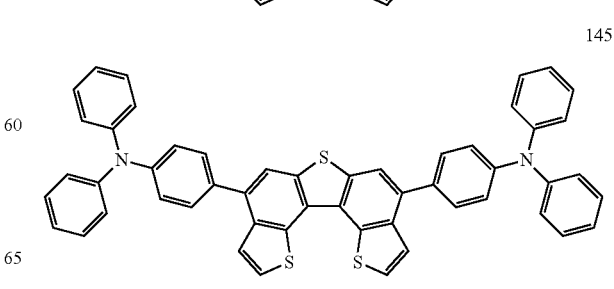

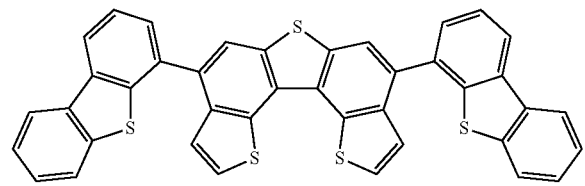
146
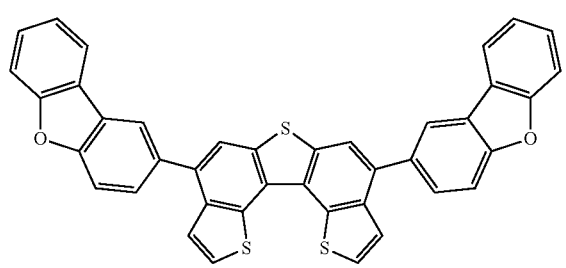
147
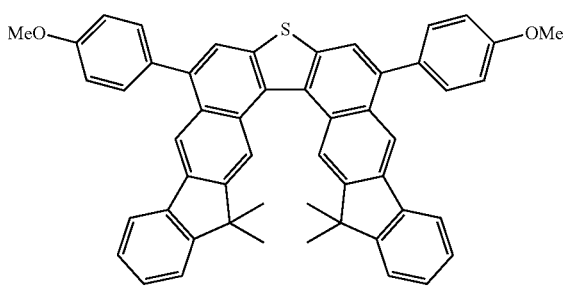
148
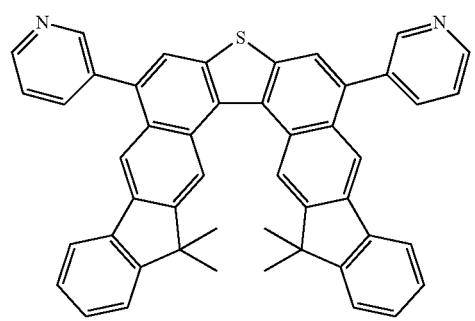
149
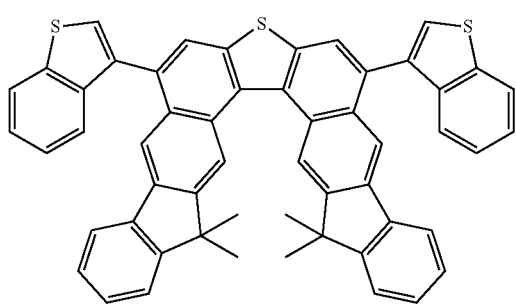
150
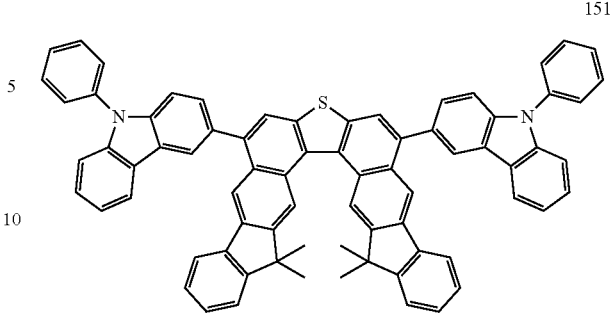
151
152
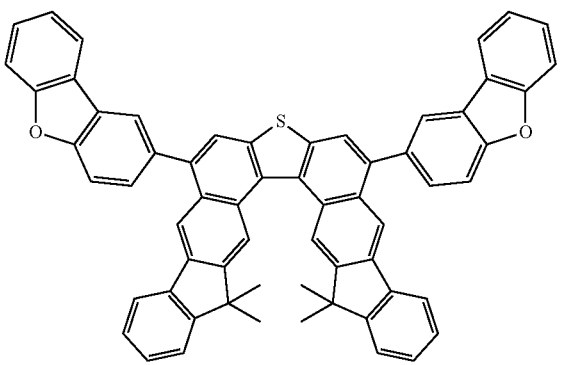
153
154

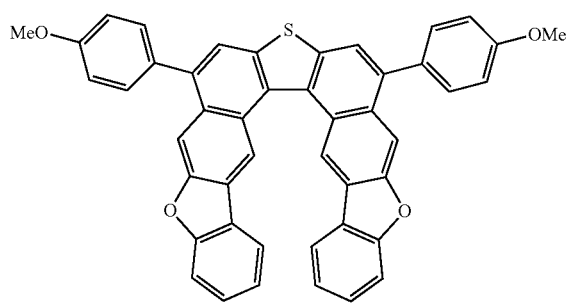
155
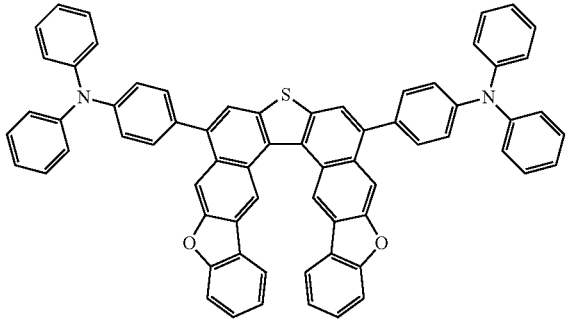
159
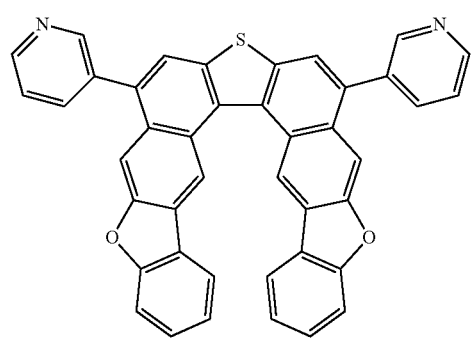
156
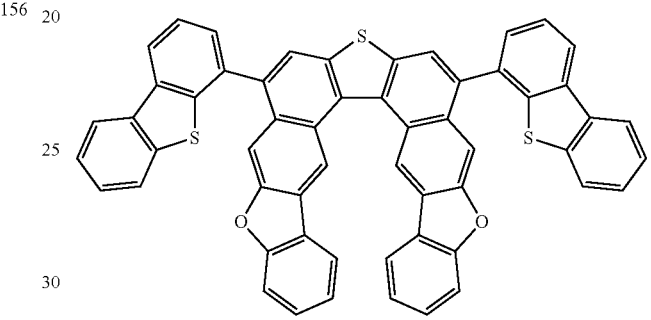
160
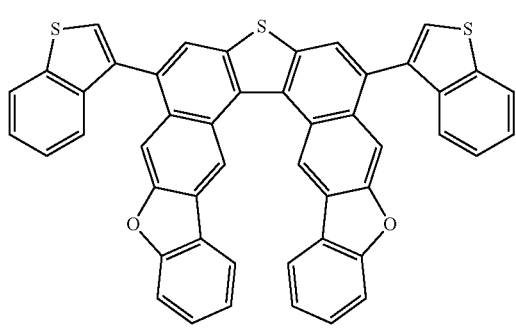
157
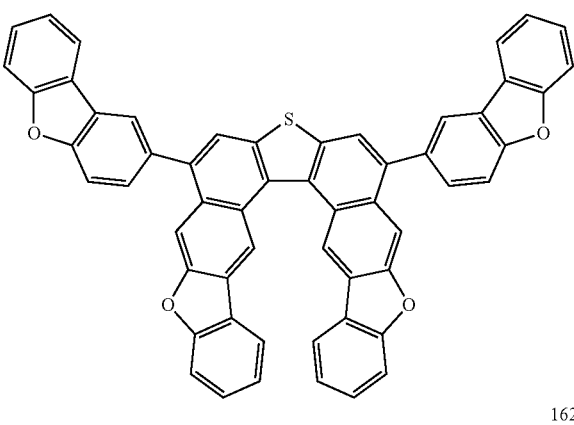
161
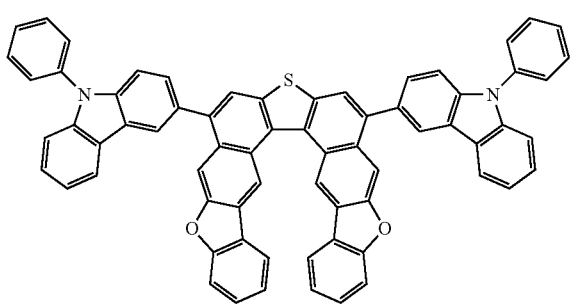
158
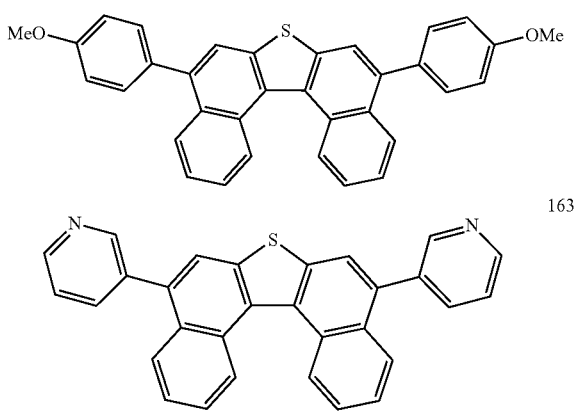
162
163

-continued

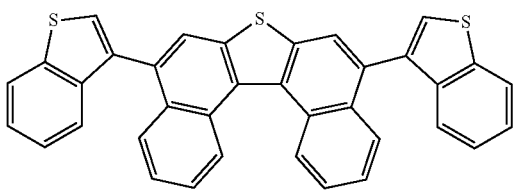
164

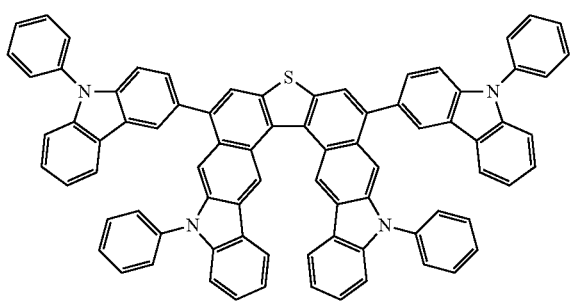
165

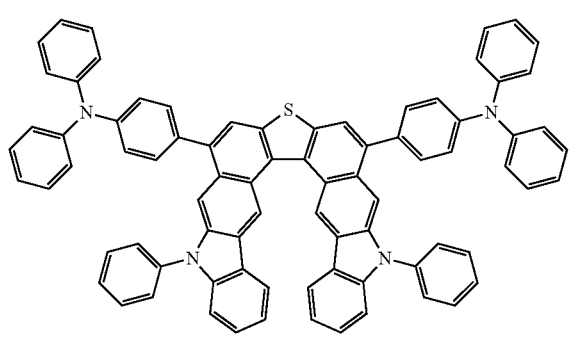
166

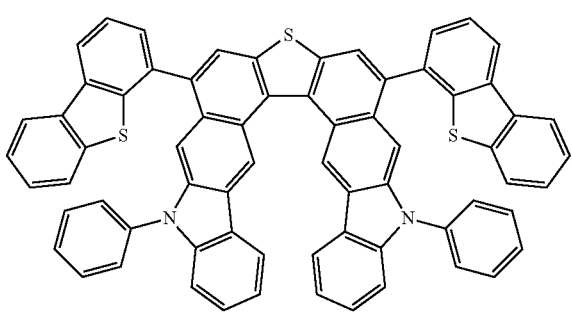
167

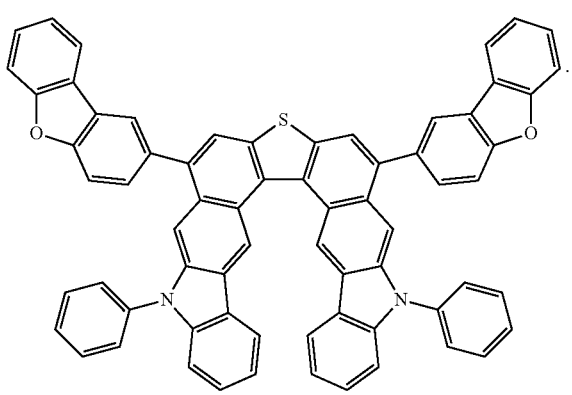
168

The heterocyclic compound of Formula 1 may have a rigid backbone structure including an aromatic ring or a heteroaromatic ring fused to a molecular dibenzofuran or dibenzothiophene structure. The compound may have a high glass transition temperature and a high melting point.

An organic light-emitting device including the heterocyclic compound of Formula 1 may have high heat resistance against Joule's heat generated between organic layers, in an organic layer, and/or between the EML and a metal electrode when stored and/or operated.

The heterocyclic compound of Formula 1 may be synthesized using known organic synthesis methods. Synthesis methods of the heterocyclic compound of Formula 1 may be understood by those of ordinary skill in the art from the examples that will be described below. The heterocyclic compound of Formula 1 may be used between a pair of electrodes of an organic light-emitting device. For example, the heterocyclic compound of Formula 1 may be used in an emission layer, or in a layer between a cathode and the emission layer (for example, in an electron injection layer, an electron transport layer, or a functional layer having both electron injection and electron transport capabilities).

Hereinafter, an organic light-emitting device 10 according to an embodiment of the present invention will be described with reference to FIG. 1, but the structure of the organic light-emitting device is not limited to the structure illustrated in FIG. 1.

Referring to FIG. 1, the organic light-emitting device 10 includes a substrate 11, a first electrode 13 disposed on the substrate 11, a second electrode 19 facing the first electrode 13, and an organic layer 15 between the first electrode 13 and the second electrode 19. The organic layer 15 includes the heterocyclic compound of Formula 1 described above.

The term "organic layer" as used herein refers to a single layer and/or a plurality of layers disposed between the first and second electrodes of the organic light-emitting device.

As used herein, the phrase "(for example, the organic layer) including the heterocyclic compound of Formula 1" means "(the organic layer) including one or at least two different heterocyclic compounds represented by Formula 1 above."

The heterocyclic compound of Formula 1 may have high heat resistance against Joule's heat generated between multiple layers of the organic layer 15, in the organic layer 15, and/or between the emission layer and a metal electrode when the organic light-emitting device 10 is operated. Therefore, the organic light-emitting device 10 including the heterocyclic compound of Formula 1 may be consistently thermally stable in high-temperature environments over time, and thus have high durability and a long lifetime.

The organic layer 15 may include at least one of a hole injection layer, a hole transport layer, a functional layer having both hole injection and hole transport capabilities, a buffer layer, an emission layer 16, a hole blocking layer, an electron transport layer, an electron injection layer, and/or a functional layer having both electron injection and electron transport capabilities. In this regard, the heterocyclic compound of Formula 1 may be included in at least one of the hole injection layer, the hole transport layer, the functional layer having both hole injection and hole transport capabilities, the buffer layer, the emission layer 16, the hole blocking layer, the electron transport layer, the electron injection layer, and/or the functional layer having both electron injection and electron transport capabilities.

The organic layer 15 may include at least one of a hole injection layer, a hole transport layer, and/or a functional layer having both hole injection and hole transport capabilities between the emission layer 16 and the first electrode 13.

At least one of the hole injection layer, the hole transport layer, and/or the functional layer having both hole injection and hole transport capabilities may include the heterocyclic compound of Formula 1.

At least one of the hole injection layer, the hole transport layer, and/or the functional layer having both hole injection and hole transport capabilities may further include a charge-generating material, which may be at least one of a quinone derivative, a metal oxide, and/or a cyano group-containing compound. Examples of the metal oxide include molybdenum oxides and vanadium oxides. The charge-generating material, have strong hole acceptability, may facilitate the injection and transport of holes.

The organic layer 15 may include at least one of an electron injection layer, an electron transport layer, and/or a functional layer having both electron injection and electron transport capabilities between the emission layer 16 and the second electrode 19. At least one of the electron injection layer, the electron transport layer, and/or the functional layer having both electron injection and electron transport capabilities may include the heterocyclic compound of Formula 1.

The organic layer 15 may further include the emission layer 16, and the emission layer 16 may include the heterocyclic compound of Formula 1.

The heterocyclic compound of Formula 1 in the emission layer 16 may serve as a fluorescent or phosphorescent host. The heterocyclic compound of Formula 1 in the emission layer 16 may serve as a fluorescent or phosphorescent host emitting red, green, or blue light, and in some embodiments, may be effectively used as a blue fluorescent host. In some embodiments, the heterocyclic compound of Formula 1 in the emission layer 16 may serve as a fluorescent dopant.

The organic layer 15 may include the emission layer 16, and at least one of an electron injection layer, an electron transport layer, and/or a functional layer having both electron injection and electron transport capabilities. The emission layer 16 and the at least one of the electron injection layer, the electron transport layer, and/or the functional layer having both electron injection and electron transport capabilities may include the heterocyclic compound of Formula 1 above. The emission layer 16 may include an arylamine compound. The arylamine compound may be any known compound used in the emission layer.

Hereinafter, a method of manufacturing the organic light-emitting device 10, according to an embodiment of the present invention will be described with reference to FIG. 1.

The substrate 11, which may be any substrate generally used in organic light-emitting devices, may be a glass substrate or a transparent plastic substrate with good mechanical strength, thermal stability, transparency, surface smoothness, ease of handling, and water resistance.

The first electrode 13 may be formed by depositing or sputtering a first electrode-forming material on the substrate 11. When the first electrode 13 is an anode, a material having a high work function may be used as the first electrode-forming material to facilitate hole injection. The first electrode 13 may be a reflective electrode or a transparent electrode. A transparent material with high conductivity, such as ITO, IZO, $SnO_2$, and ZnO, may be used as the first electrode-forming material. In some embodiments, the first electrode 13 may be formed as a reflective electrode using magnesium (Mg), aluminum (Al), aluminum-lithium (Al—Li), calcium (Ca), magnesium-indium (Mg—In), magnesium-silver (Mg—Ag), or the like. The first electrode 13 may have a single-layer structure or a multi-layer structure including at least two layers. For example, the first electrode 13 may have a three-layered structure of ITO:Ag:ITO, but is not limited thereto.

The organic layer 15 may be formed on the first electrode 13. The organic layer 15 may include a hole injection layer (HIL, not shown), a hole transport layer (HTL, not shown), a buffer layer (not shown), an emission layer (EML) 16, an electron transport layer (ETL, not shown), and an electron injection layer (EIL, not shown).

The HIL may be formed on the first electrode 13 using any of a variety of methods, such as vacuum deposition, spin coating, casting, Langmuir-Blodgett (LB) deposition, or the like. When the HIL is formed using vacuum deposition, the vacuum deposition conditions may vary according to the compound that is used to form the HIL, and the desired structure and thermal properties of the HIL to be formed. For example, vacuum deposition may be performed at a temperature of about 100° C. to about 500° C., a pressure of about $10^{-8}$ torr to about $10^{-3}$ torr, and a deposition rate of about 0.01 to about 100 Å/sec. However, the deposition conditions are not limited thereto.

When the HIL is formed using spin coating, the coating conditions may vary according to the compound that is used to form the HIL, and the desired structure and thermal properties of the HIL to be formed. For example, the coating rate may be in a range of about 2000 rpm to about 5000 rpm, and a temperature at which heat treatment is performed to remove solvent after coating may be in a range of about 80° C. to about 200° C. However, the coating conditions are not limited thereto.

The HIL may be formed of any material that is commonly used to form a HIL. Non-limiting examples of the material that can be used to form the HIL include N,N'-diphenyl-N,N'-bis-[4-(phenyl-m-tolyl-amino)-phenyl]-biphenyl-4,4'-diamine, (DNTPD), a phthalocyanine compound such as copperphthalocyanine, 4,4',4"-tris(3-methylphenylphenylamino)triphenylamine (m-MTDATA), N,N'-di(1-naphthyl)-N,N'-diphenylbenzidine (NPB), TDATA, 2-TNATA, polyaniline/dodecylbenzenesulfonic acid (Pani/DBSA), poly(3,4-ethylenedioxythiophene)/poly(4-styrenesulfonate) (PEDOT/PSS), polyaniline/camphor sulfonicacid (Pani/CSA), and polyaniline/poly(4-styrenesulfonate (PANI/PSS).

The thickness of the HIL may be from about 100 Å to about 10000 Å, and in some embodiments, may be from about 100 Å to about 1000 Å. When the thickness of the HIL is within these ranges, the HIL may have good hole injecting ability without substantially increasing driving voltage.

Then, a HTL may be formed on the HIL by vacuum deposition, spin coating, casting, Langmuir-Blodgett (LB) deposition, or the like. When the HTL is formed using vacuum deposition or spin coating, the conditions for deposition or coating may be similar to those for the formation of the HIL, though the conditions for the deposition or coating may vary according to the material that is used to form the HTL.

The HTL-forming material may be any known compound. Non-limiting examples of suitable HTL-forming materials include carbazole derivatives, such as N-phenylcarbazole or polyvinylcarbazole, N,N'-bis(3-methylphenyl)-N,N'-diphenyl-[1,1-biphenyl]-4,4'-diamine (TPD), 4,4',4"-tris(N-carbazolyl)triphenylamine (TCTA), and N,N'-di(1-naphthyl)-N,N'-diphenylbenzidine) (NPB).

The thickness of the HTL may be from about 50 Å to about 2000 Å, and in some embodiments, may be from about 100 Å to about 1500 Å. When the thickness of the HTL is within these ranges, the HTL may have good hole transporting ability without substantially increasing driving voltage.

The functional layer having both hole injection and hole transport capabilities may include at least one of a HIL-forming material and a HTL-forming material. The functional layer having both hole injection and hole transport capabilities may have a thickness of from about 500 Å to about 10,000 Å, and in some embodiments, may have a thickness of from about 100 Å to about 1,000 Å. When the thickness of the functional layer having both hole injection and hole transport capabilities is within these ranges, the functional layer may have good hole injection and transport capabilities without substantially increasing driving voltage.

At least one of the HIL, the HTL, and the functional layer having both hole injection and hole transport capabilities may further include, in addition to a HIL-forming material, a charge-generating material, as described above.

A buffer layer may be disposed between the EML 16 and at least one of the HIL, HTL, and functional layer having both hole injection and transport capabilities. The buffer layer may compensate for an optical resonance distance of light according to a wavelength of the light emitted from the EML 16, and thus may increase efficiency. The butter layer may include any HIL-forming material, or a HTL-forming material.

Then, the EML 16 may be formed on the HTL, the functional layer having both hole injection and transport capabilities, or the buffer layer by vacuum deposition, spin coating, casting, Langmuir-Blodget (LB) deposition, or the like. When the EML 16 is formed by vacuum deposition or spin coating, the deposition or coating conditions may be similar to those for the formation of the HIL, though the conditions for deposition or coating may vary according to the material that is used to form the EML 16.

The EML 16 may include the heterocyclic compound of Formula 1 as a host material. In some embodiments, the EML 16 may further include a known host, in addition to the heterocyclic compound of Formula 1. Non-limiting examples of the host include $Alq_3$, 4,4'-N,N'-dicarbazole-biphenyl (CBP), poly(n-vinylcarbazole) (PVK), 9,10-di(naphthalene-2-yl)anthracene (ADN), TCTA, 1,3,5-tris(N-phenylbenzimidazole-2-yl)benzene (TPBI), 3-tert-butyl-9,10-di-2-naphthylanthracene (TBADN), E3, distyrylarylene (DSA), and dmCBP.

When the organic light-emitting device 10 includes at least one of a red EML, a green EML, and a blue EML, the EML 16 may include the heterocyclic compound of Formula 1. In some embodiments the EML 16 may further include a known dopant, in addition to the heterocyclic compound of Formula 1 above. Non-limiting examples of dopants are as follows. "ppy" is the abbreviation for phenylpyridine.

Non-limiting examples of a blue dopant include compounds represented by the following formulae.

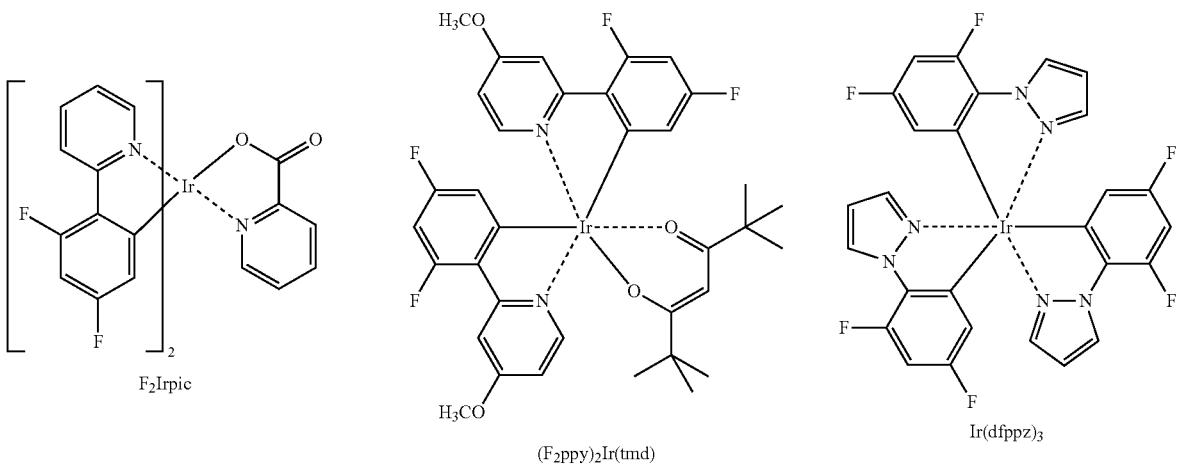

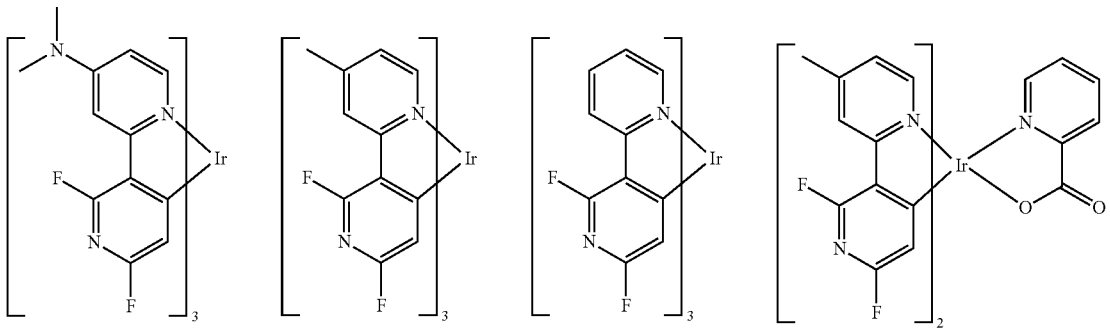

51
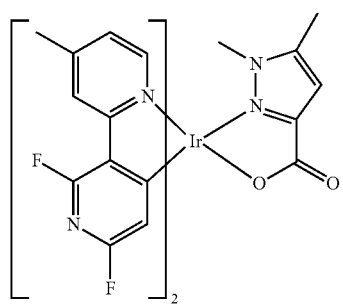
-continued
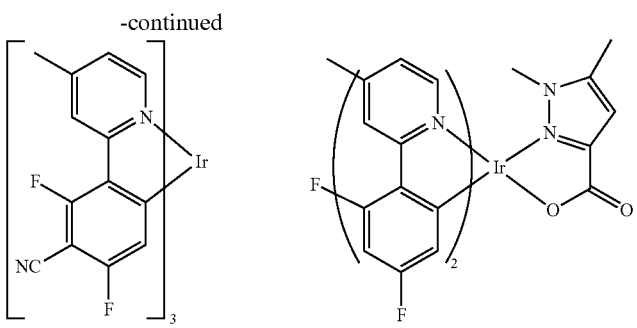
52
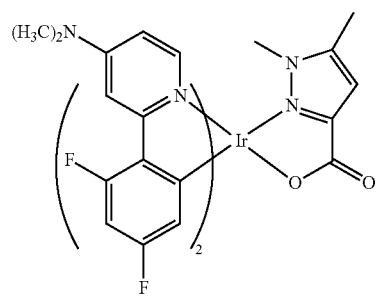 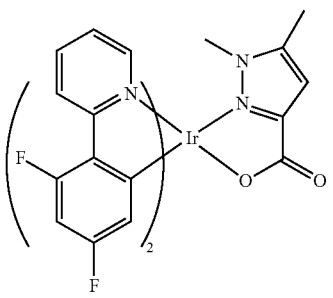
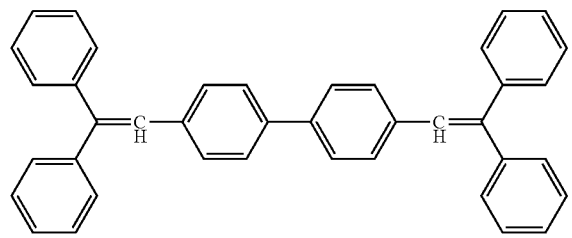
DPVBi

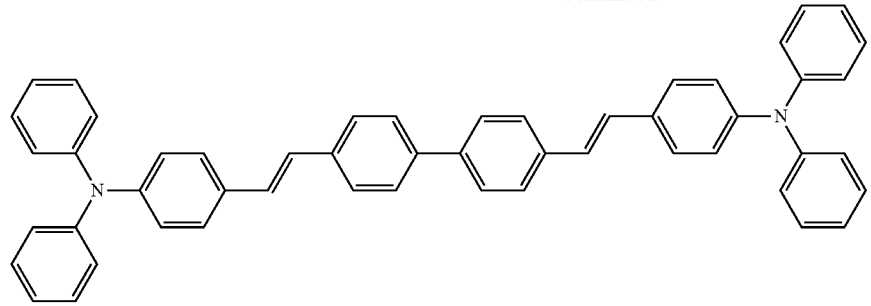
DPAVBi
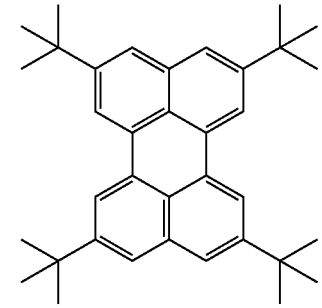
TBPe
Non-limiting examples of a red dopant include compounds represented by the following formulae.
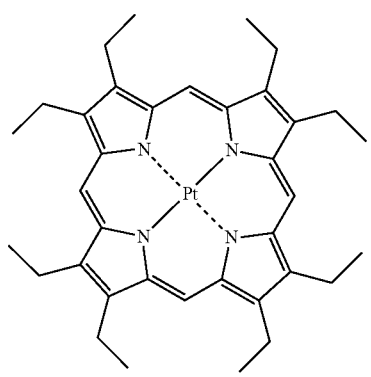
PtOEP
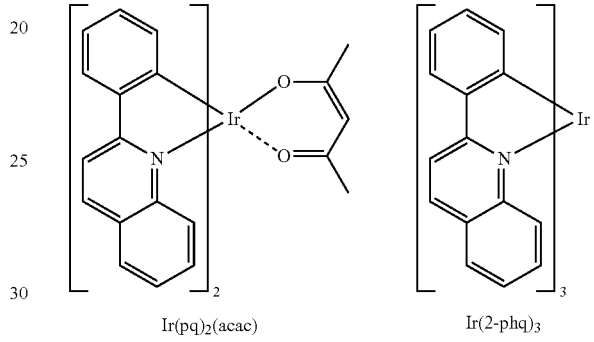
Ir(pq)₂(acac)  Ir(2-phq)₃
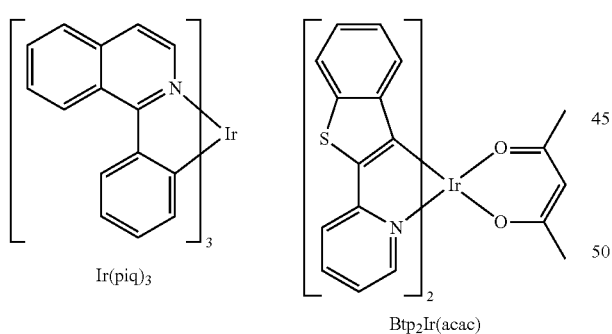
Ir(piq)₃  Btp₂Ir(acac)
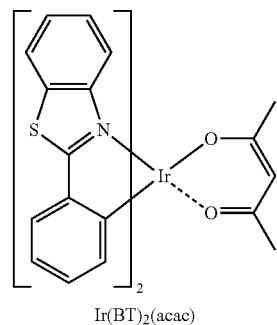
Ir(BT)₂(acac)
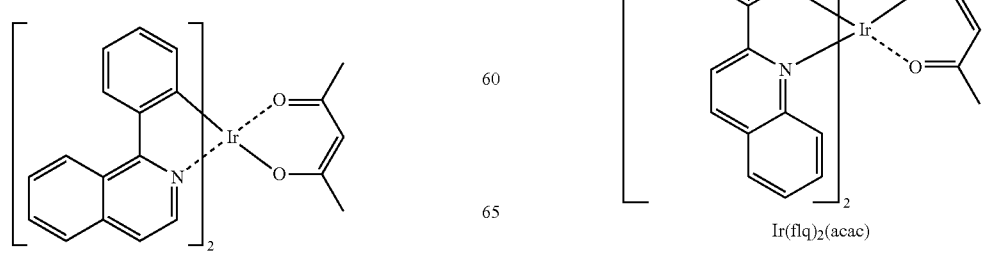
Ir(flq)₂(acac)

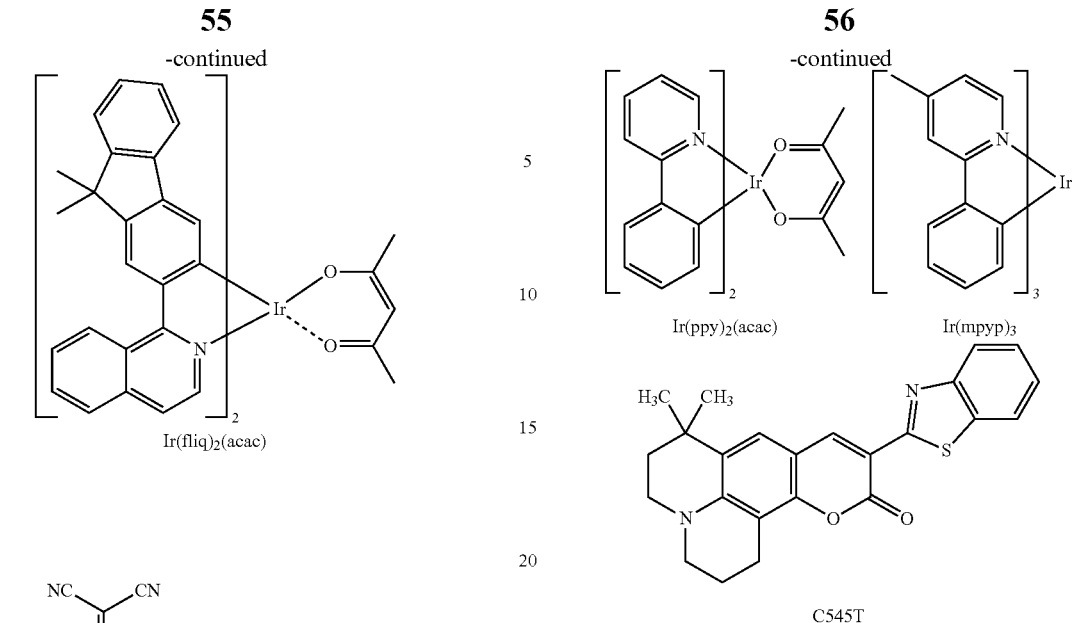

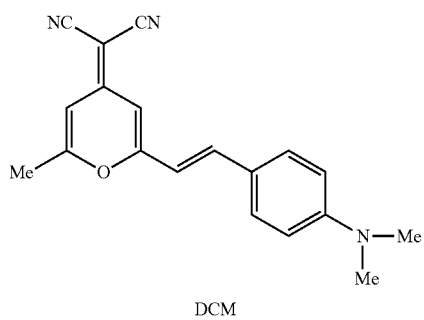
DCM

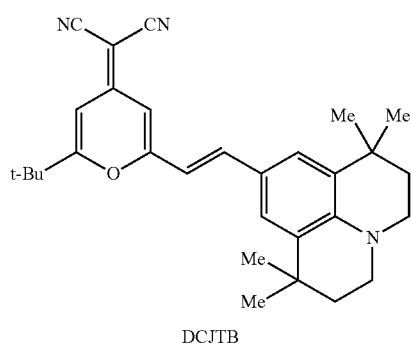
DCJTB

Non-limiting examples of a green dopant include compounds represented by the following formulae.

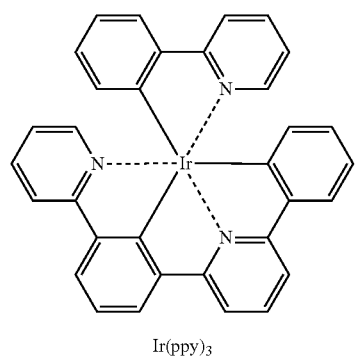
Ir(ppy)₃

Non-limiting examples of dopants for the EML 16 include Pt-complexes and Os-complexes.

In the organic light-emitting device 10, when at least one of the EML 16, the EIL, the ETL, and/or the functional layer having both electron injection and transport capabilities includes the heterocyclic compound of Formula 1, the EML 16 may include a known arylamine compound.

When the EML 16 includes both a host and a dopant, the amount of the dopant may be from about 0.01 parts to about 15 parts by weight based on 100 parts by weight of the host. However, the amount of the dopant is not limited to this range.

A thickness of the EML 16 may be from about 100 Å to about 1000 Å, and in some embodiments, may be from about 200 Å to about 600 Å. When the thickness of the EML 16 is within these ranges, the EML 160 may have improved light emitting ability without substantially increasing driving voltage.

Then, an ETL may be formed on the EML 16 using any of a variety of methods, such as vacuum deposition, spin coating, casting, or the like. When the ETL is formed by vacuum deposition or spin coating, the deposition or coating conditions may be similar to those for the formation of the HIL, though the deposition or coating conditions may vary according to the compound that is used to form the ETL. An ETL-forming material may be at least one of the heterocyclic compound of Formula 1 and/or any known ETL-forming material. Non-limiting examples of ETL forming materials include a quinoline derivative, such as tris(8-quinolinorate) aluminum (Alq3), TAZ, BAlq, beryllium bis(benzoquinolin-10-olate) (Bebq₂), 9,10-di(naphthalene-2-yl)anthracene (ADN), Compound 201, and Compound 202.

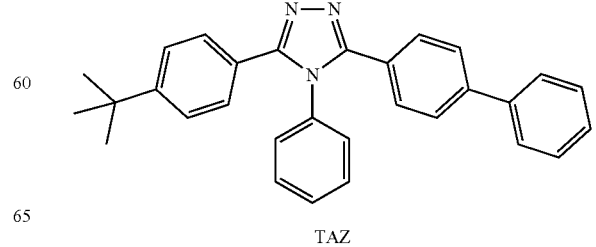
TAZ

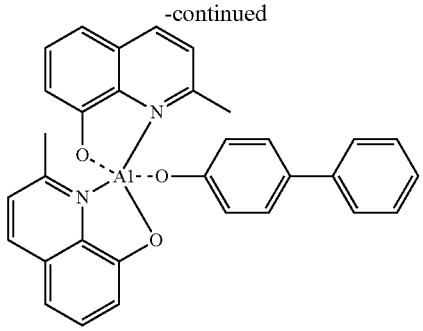

BAlq

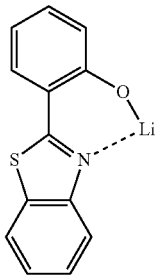

Compound 203

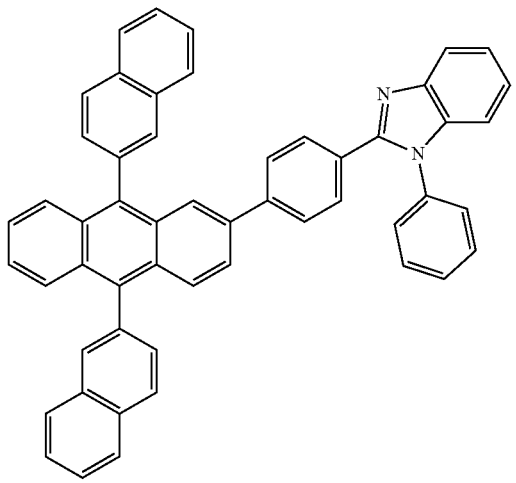

Compound 201

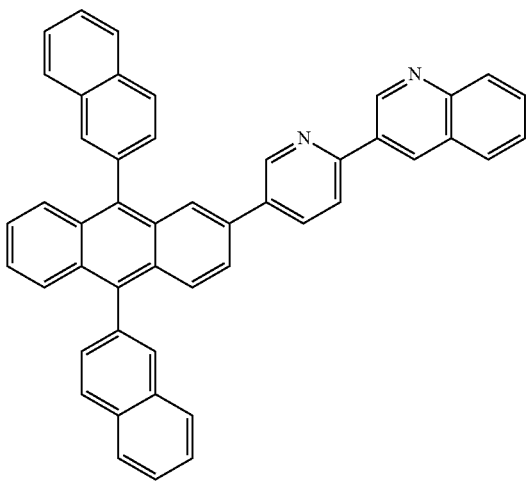

Compound 202

The thickness of the ETL may be from about 100 Å to about 1,000 Å, and in some embodiments, may be from about 150 Å to about 500 Å. When the thickness of the ETL is within these ranges, the ETL may have satisfactory electron transporting ability without substantially increasing driving voltage.

The ETL may further include a metal complex, in addition to at least one of the heterocyclic compound of Formula 1 and/or a known ETL-forming material. The metal complex may be a lithium (Li) complex. Non-limiting examples of the Li complex include lithium quinolate (LiQ) or Compound 203 below.

An EIL, which facilitates injection of electrons from the cathode, may be formed on the ETL. Examples of an EIL-forming material include LiF, NaCl, CsF, $Li_2O$, and BaO. The deposition or coating conditions for forming the EIL 18 may be similar to those for the formation of the HIL, though the deposition or coating conditions may vary according to the material that is used to form the EIL 18. A thickness of the EIL may be from about 1 Å to about 100 Å, and in some embodiments, from about 3 Å to about 90 Å. When the thickness of the EIL is within these ranges, the EIL may have satisfactory electron injection ability without substantially increasing driving voltage.

The second electrode 19 may be formed on the organic layer 15. The second electrode 19 may be a cathode, which is an electron injection electrode. Suitable metals for forming the second electrode 19 include metals, alloys, electro-conductive compounds that have low work functions, or mixtures thereof. For example, the second electrode 19 may be formed as a transmission electrode in a thin film form using Li, Mg, Al, Al:Li, Ca, Mg:In, Mg:Ag, or the like. In some embodiments, to manufacture a top-emission light-emitting device, the transmission electrode may be formed of indium tin oxide (ITO) or indium zinc oxide (IZO).

When a phosphorescent dopant is used in the EML, a HBL may be formed between the HTL and the EML 16 or between the functional layer having both hole injection and transport capabilities and the EML 16 by vacuum deposition, spin coating, casting, Langmuir-Blodgett (LB) deposition, or the like, in order to prevent diffusion of triplet excitons or holes into the ETL. When the HBL is formed using vacuum deposition or spin coating, the conditions for deposition or coating may be similar to those for the formation of the HIL, although the conditions for deposition or coating may vary according to the material that is used to form the HBL. The HBL may be formed using a known HBL-forming material, for example, an oxadiazole derivative, a triazole derivative, a phenanthroline derivative, or the like, but is not limited thereto. For example, the HBL may be formed from 2,9-dimethyl-4,7-diphenyl-1,10-phenanthroline (BCP) represented by the following formula.

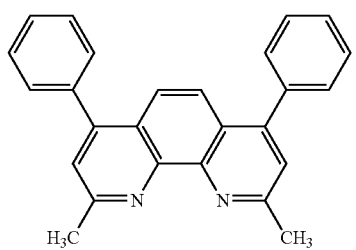

BCP

A thickness of the HBL may be from about 20 Å to about 1000 Å, and in some embodiments, may be from about 30 Å to about 300 Å. When the thickness of the HBL is within these ranges, the HBL may have improved hole blocking properties without substantially increasing driving voltage.

According to an aspect of the present invention, an organic light-emitting display apparatus includes: a transistor with a source, a drain, a gate, and an active layer; and the above-described organic light-emitting device. One of the source and the drain of the transistor is electrically connected to the first electrode of the organic light-emitting device.

The active layer of the transistor may be in any of a variety of forms, for example, an amorphous silicon layer, a crystalline silicon layer, an organic semiconductor layer, or an oxide semiconductor layer.

As used herein, examples of the "unsubstituted $C_1$-$C_{30}$ alkyl group" (or "$C_1$-$C_{30}$alkyl group") include C1-C30 linear of branched alkyl groups, such as methyl, ethyl, propyl, isobutyl, sec-butyl, pentyl, iso-amyl, and hexyl. Examples of the substituted $C_1$-$C_{30}$alkyl groups include the unsubstituted $C_1$-$C_{30}$ alkyl group in which at least one hydrogen atom is substituted with one of a deuterium atom, a halogen atom, a hydroxyl group, a cyano group, an amino group, a nitro group, an amidino group, hydrazine, hydrazone, a carboxyl group or a salt thereof, a sulfonic acid group or a salt thereof, a phosphoric acid group or a salt thereof, a $C_1$-$C_{30}$alkyl group, a $C_2$-$C_{30}$alkenyl group, a $C_2$-$C_{30}$alkynyl group, a $C_1$-$C_{30}$alkoxy group, a $C_3$-$C_{30}$cycloalkyl group, a $C_3$-$C_{30}$cycloalkenyl group, a $C_6$-$C_{30}$ aryl group, an unsubstituted $C_6$-$C_{30}$aryloxy group, a $C_6$-$C_{30}$arylthio group, a $C_2$-$C_{30}$ heteroaryl group, —N($Q_{101}$)($Q_{102}$), and —Si($Q_{103}$)($Q_{104}$)($Q_{105}$)($Q_{106}$). $Q_{101}$ to $Q_{106}$ are each independently one of a hydrogen atom, a $C_1$-$C_{30}$alkyl group, a $C_2$-$C_{30}$ alkenyl group, a $C_2$-$C_{30}$ alkynyl group, a $C_6$-$C_{30}$ aryl group, or $C_2$-$C_{30}$ heteroaryl group).

As used herein, the unsubstituted $C_2$-$C_{30}$ alkenyl group is a hydrocarbon chain having a carbon-carbon double bond in the center or at a terminal end of the unsubstituted $C_2$-$C_{30}$ alkyl group. Examples of the unsubstituted $C_2$-$C_{30}$ alkenyl group include ethenyl, propenyl, and butenyl groups. To obtain the substituted $C_2$-$C_{30}$ alkenyl group, at least one hydrogen atom in the $C_2$-$C_{30}$ alkenyl group may be substituted with the substituents described above in connection with the substituted $C_1$-$C_{30}$ alkyl group.

As used herein, the unsubstituted $C_2$-$C_{30}$ alkynyl group is an alkyl group having at least one carbon-carbon triple bond in the center or at a terminal end of the $C_2$-$C_{30}$ alkyl group. Examples of the unsubstituted $C_2$-$C_{30}$ alkynyl group are ethynyl and propynyl. The substituted $C_2$-$C_{30}$ alkynyl groups include the unsubstituted $C_2$-$C_{30}$ alkynyl groups in which at least one hydrogen atom is substituted with the substituents described above in connection with the substituted $C_1$-$C_{30}$ alkyl group.

As used herein, the unsubstituted $C_1$-$C_{30}$alkoxy group may be represented by the formula —OA in which A is an unsubstituted $C_1$-$C_{30}$alkyl group as described above. Non-limiting examples thereof include methoxy, ethoxy, and isopropyloxy. The substituted $C_1$-$C_{30}$ alkoxy group may be a $C_1$-$C_{30}$ alkyl group in which at least one hydrogen atom is substituted with the same substituents described above in connection with the substituted $C_1$-$C_{30}$ alkyl group.

As used herein, the unsubstituted $C_3$-$C_{30}$ cycloalkyl group may be a saturated $C_3$-$C_{30}$ monocyclic, bicyclic, or tricyclic non-aromatic hydrocarbon group. Non-limiting examples thereof include cyclopropyl, cyclobutyl, cyclopentyl, cyclohexyl, cycloheptyl, cyclooctyl, and decahydronaphthalenyl. The substituted $C_3$-$C_{30}$ cycloalkyl group may be a $C_3$-$C_{30}$ cycloalkyl group in which at least one hydrogen atom is substituted with the same substituents described above in connection with the substituted $C_1$-$C_{30}$ alkyl group.

As used herein, the unsubstituted $C_3$-$C_{30}$ cycloalkenyl group may be an unsaturated $C_3$-$C_{30}$ monocyclic, bicyclic, or tricyclic non-aromatic hydrocarbon group. Non-limiting examples thereof include cyclopentenyl, and cyclohexenyl. The substituted $C_3$-$C_{30}$ cycloalkenyl group may be a $C_3$-$C_{30}$ cycloalkenyl group in which at least one hydrogen atom is substituted with the same substituents described above in connection with the substituted $C_1$-$C_{30}$ alkyl group.

The unsubstituted $C_6$-$C_{30}$ aryl group is a monovalent group having a carbocyclic aromatic system having 6 to 30 carbon atoms including at least one aromatic ring. The unsubstituted $C_6$-$C_{30}$ arylene group is a bivalent group having a carbocyclic aromatic system having 6 to 30 carbon atoms including at least one aromatic ring. When the aryl group or the arylene group has at least two rings, they may be fused to each other or connected to each other via a single bond. The substituted $C_6$-$C_{30}$ aryl group is a $C_6$-$C_{30}$ aryl group in which at least one hydrogen atom is substituted with the same substituents described above in connection with the substituted $C_1$-$C_{30}$ alkyl group. The substituted $C_6$-$C_{30}$ arylene group is a $C_6$-$C_{30}$ arylene group in which at least one hydrogen atom is substituted with the same substituents described above in connection with the substituted $C_1$-$C_{30}$ alkyl group.

As used herein, the unsubstituted $C_6$-$C_{30}$ aryloxy group is represented by —O$A_2$ in which $A_2$ is a substituted or unsubstituted $C_6$-$C_{30}$aryl group. The substituted $C_6$-$C_{30}$ aryloxy group is a $C_6$-$C_{30}$ aryloxy group in which at least one hydrogen atom is substituted with the same substituents described above in connection with the substituted $C_1$-$C_{30}$ alkyl group.

As used herein, the unsubstituted $C_6$-$C_{30}$ arylthio group is represented by —S$A_3$ in which $A_3$ is a substituted or unsubstituted $C_3$-$C_{30}$ aryl group. The substituted $C_6$-$C_{30}$ arylthio group is a $C_6$-$C_{30}$ arylthio group in which at least one hydrogen atom is substituted with the same substituents described above in connection with the substituted $C_1$-$C_{30}$ alkyl group.

The unsubstituted $C_2$-$C_{30}$ heteroaryl group is a monovalent group having at least one aromatic ring having at least one heteroatom selected from N, O, P, and S, and at least one carbon atom. The unsubstituted $C_2$-$C_{30}$ heteroarylene group is a bivalent group having at least one aromatic ring having at least one heteroatom selected from N, O, P, and S, and at least one carbon atom. In this regard, when the heteroaryl group and the heteroarylene group have at least two rings, they may be fused to each other or connected to each other via a single bond. The substituted $C_2$-$C_{30}$ heteroaryl group is a $C_2$-$C_{30}$ heteroaryl group in which at least one hydrogen atom is substituted with the same substituents described above in connection with the substituted $C_1$-$C_{30}$ alkyl group. The substituted $C_2$-$C_{30}$ heteroarylene group is a $C_2$-$C_{30}$ heteroarylene group in which at least one hydrogen atom is substituted with the same substituents described above in connection with the substituted $C_1$-$C_{30}$ alkyl group.

Hereinafter, the present invention will be described with reference to the following synthesis examples and other examples. However, these examples are presented for illustrative purposes only and are not intended to limit the scope of the present invention.

INTERMEDIATES A TO E WERE SYNTHESIZED AS FOLLOWS
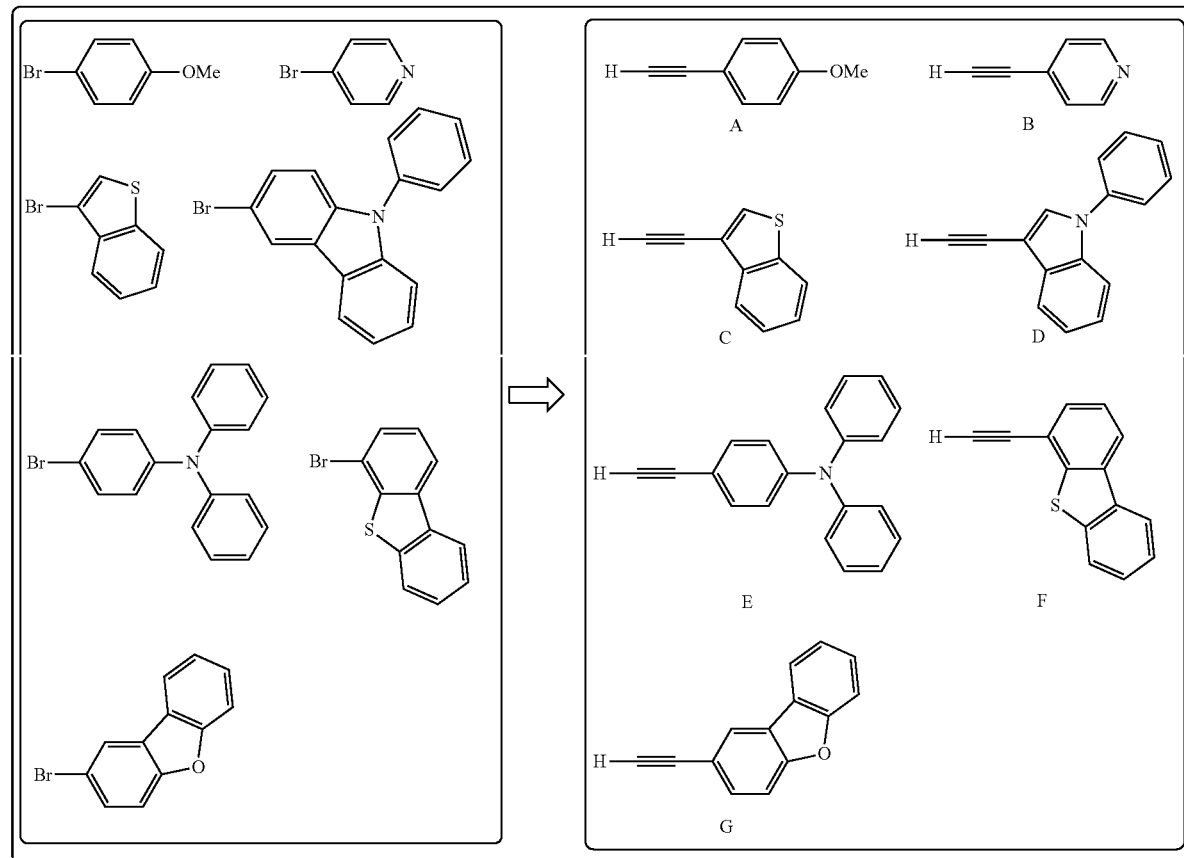
Synthesis of Intermediate D
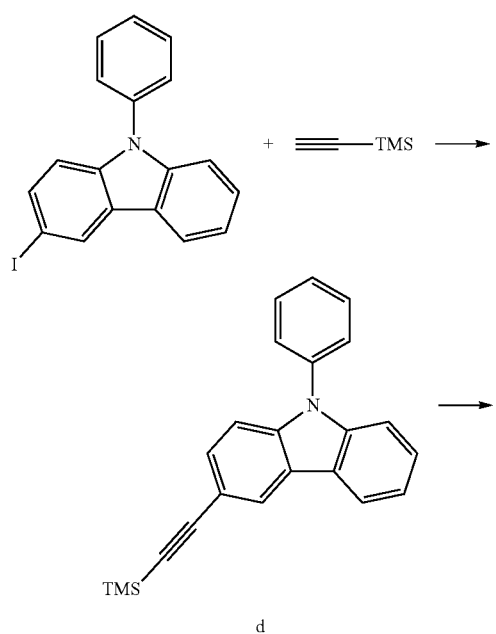
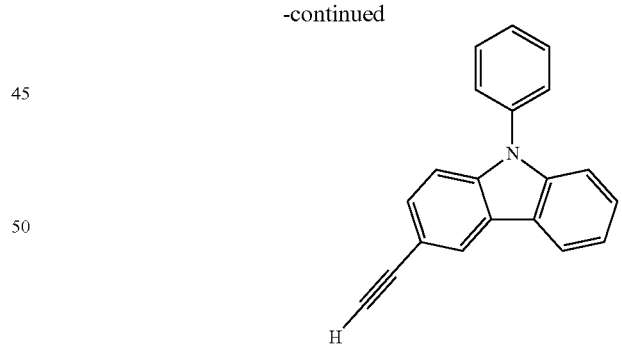
Synthesis Example 1
Synthesis of Intermediate d
22 g of 3-Iodo-9-phenyl-9H-carbazole, 2.8 g (0.04 eq) of Pd(PPh$_3$)$_4$, and 914 mg (0.08 eq) of CuI were put into a flask in a vacuum, which was then supplied with N$_2$ gas. After 200 mL of tetrahydrofuran (THF) was added into the flask and then stirred, 10 mL (1.2 eq) of triethylamine and 10.0 g (1.2 eq) of TMS-acetylene were slowly dropwise added thereto, and then stirred at room temperature for about 2 hours in a $N_2$ atmosphere. After removing the solvent using a rotary evaporator, the resulting reaction product was extracted two times each with 200 mL of $Et_2O$ and 150 mL of water. The organic layer was collected and then dried using magnesium sulfate to evaporate the solvent. The residue was separated and purified by silica gel column chromatography to obtain 20 g of Intermediate d (Yield: 99%). This compound was identified using liquid chromatography-mass spectroscopy (LC-MS). $C_{23}H_{21}N_1Si_1$: M+339.14

Synthesis Example 2

Synthesis of Intermediate D 4.2 g of Intermediate d was dissolved in 50 mL of THF, and 30 mL (3 eq) of tetrabutylammonium fluoride in THF (1.0M) was dropwise added thereto and stirred for about 30 minutes. 50 mL of water was added to the solution and the reaction solution was extracted three times each with 50 mL of ethylether. The organic layer was collected and then dried using magnesium sulfate to evaporate the solvent. The residue was separated and purified by silica gel column chromatography to obtain 3.5 g of Intermediate D (Yield: 95%). This compound was identified using LC-MS. $C_{20}H_{13}N_1$: M+267.10

Synthesis of Intermediates A, B, C, D, E, F, and G

Intermediates A, B, C, E, F, and G were synthesized in the same manner as Intermediate D using the same equivalents of the reactants. These compounds were identified using LC-MS.

| Intermediate | Yield (%) | | LC-MS |
| | Synthesis Example 1 | Synthesis Example 2 | |
| --- | --- | --- | --- |
| A | 98 | 95 | 132.06 |
| B | 97 | 94 | 132.04 |
| C | 98 | 96 | 158.02 |
| D | 99 | 95 | 267.10 |
| E | 98 | 97 | 269.12 |
| F | 99 | 96 | 208.03 |
| G | 97 | 97 | 192.06 |

Synthesis of Compound 25

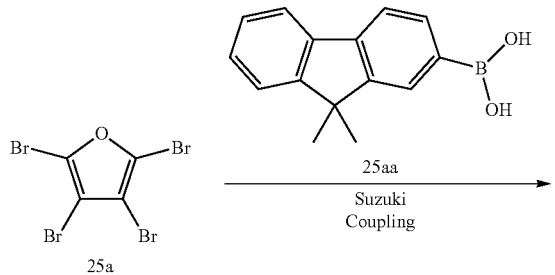

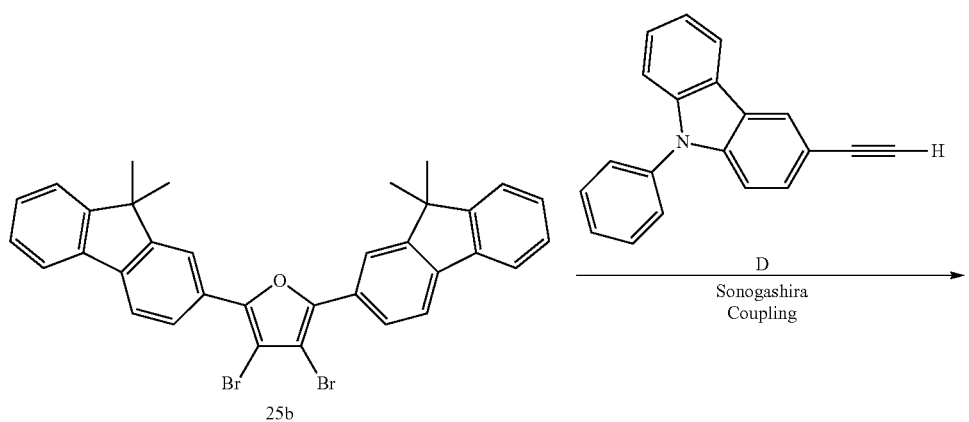

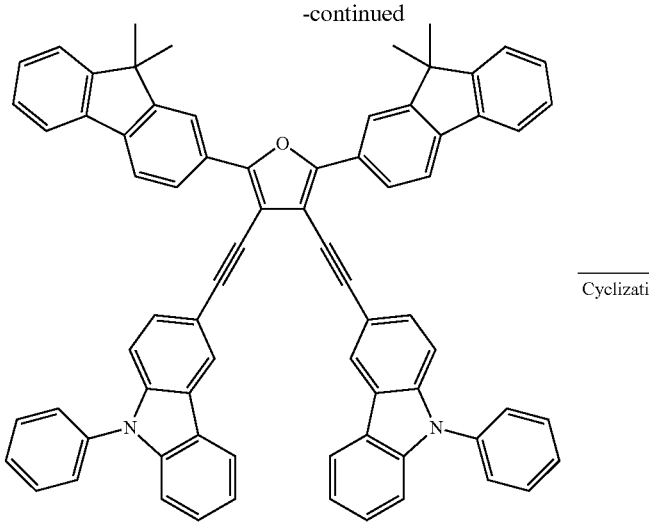

25c

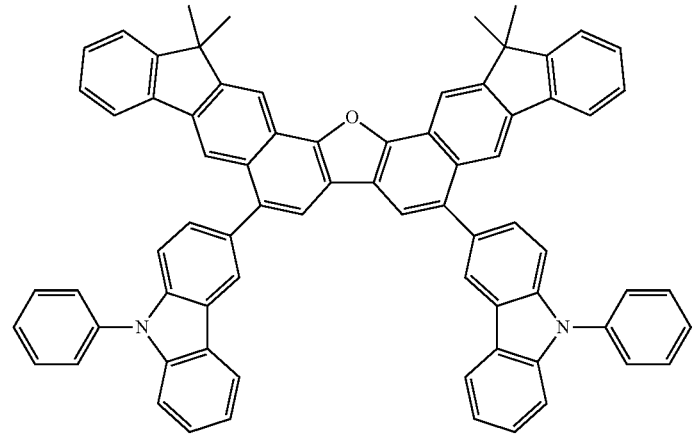

25

Synthesis Example 3

Synthesis of Intermediate 2b 5 of Intermediate 25a, 6.83 g (2.2 eq) of Intermediate 25aa, 1.5 g (0.1 eq) of Pd(PPh$_3$)$_4$, and 18.0 g (10 eq) of K$_2$CO$_3$ were dissolved in 100 mL of THF and 30 mL of distilled water to obtain a mixed solution, which was then refluxed for about 24 hours while being stirred after a temperature increase to about 120° C. The reaction solution was cooled to room temperature, followed by extraction three times each with 100 mL of water and 100 mL of diethylether. The organic phase was collected and then dried using magnesium sulfate to evaporate the solvent. The residue was separated and purified using silica gel column chromatography to obtain 5.89 g of Intermediate 25b (Yield: 74%). This compound was identified using LC-MS. C$_{34}$H$_{26}$Br$_2$O$_1$: M+610.03

Synthesis Example 4

Synthesis of Intermediate 25c 5.5 g (1 eq) of Intermediate 25b, 1.56 g (0.15 eq) of Pd(PPh$_3$)$_4$, and 510 mg (0.30 eq) of CuI were put into a flask in a vacuum, which was then supplied with N$_2$ gas. After 100 mL of THF was added into the flask and then stirred, 5.65 mL (4.5 eq) of triethylamine and 5.3 g (2.2 eq) of Compound D were slowly dropwise added thereto, and then stirred at room temperature for about 2 hours in a N$_2$ atmosphere. After removing the solvent using a rotary evaporator, 100 mL of water was added to the resulting reaction solution, which was then extracted three times each with 100 mL of ethylether. The organic layer was collected and then dried using magnesium sulfate to evaporate the solvent. The residue was separated and purified using silica gel column chromatography to obtain 5.14 g of Intermediate 25c (Yield: 58%). This compound was identified using LC-MS. C$_{74}$H$_{50}$N$_2$O$_1$: M+982.39

Synthesis Example 5

Synthesis of Compound 25

4.0 g of Intermediate 25c was dissolved in 100 mL of methylene chloride, and 11.5 mL (40 eq) of trifluoroacetic acid was dropwise added thereto and stirred at room temperature for about 1 hour. After completion of the reaction, the reaction solution was extracted three times each with 100 mL of water and 100 mL of diethylether. The organic layer was collected and then dried using magnesium sulfate, and the residue obtained by evaporating the solvent was separated and purified by silica gel column chromatography to obtain 3.68 g of Compound 25 (Yield: 92%). This compound was identified using LC-MS. $C_{74}H_{50}N_2O_1$: M+982.39

Synthesis of Compounds 1, 9, 17, 28, 33 and 41

Compounds 1, 9, 17, 28, 33, and 41 were synthesized as in Synthesis Examples 3 to 5 using the same equivalents of the reactants as in the synthesis of Compound 25. These compounds were identified using LC-MS and nuclear magnetic resonance (NMR).

| Comp. | LC-MS | NMR |
|---|---|---|
| 1 | 480.17 | 7.71 (s, 2H), 7.67 (d, 4H), 7.37 (d, 4H), 7.32 (t, 4H), 6.83 (d, 4H), 3.73 (s, 6H) |
| 9 | 424.13 | 9.15 (s, 2H), 8.81 (s, 2H), 8.55 (d, 2H), 8.45 (d, 2H), 7.97 (d, 2H), 7.72 (s, 2H), 7.50 (d, 2H), 7.44 (d, 2H) |
| 17 | 544.01 | 7.90 (d, 2H), 7.80 (d, 2H), 7.55 (s, 2H), 7.40 (d, 4H), 7.30-7.29 (m, 6H) |
| 25 | 982.39 | 8.06 (d, 2H), 7.83 (s, 2H), 7.77 (s, 2H), 7.71 (s, 2H), 7.61 (d, 2H), 7.55-7.52 (t, 4H), 7.46-7.40 ((m, 6H), 7.30-7.24 (m, 14H), 7.08 (t, 2H), 7.00 (t, 2H), 1.73 (s, 12H) |
| 28 | 832.30 | 8.06 (d, 2H), 7.83 (s, 2H), 7.71 (s, 4H), 7.61 (d, 2H), 7.52-7.41 (m, 12H), 7.24 (t, 2H), 7.19 (t, 2H), 7.13 (t, 2H), 1.73 (s, 12H) |
| 33 | 934.32 | 7.71 (s, 2H), 7.49 (d, 2H), 7.42 (d, 4H), 7.23 (d, 4H), 7.19 (m, 4H), 6.52 (t, 2H), 7.01 (t, 8H), 6.62 (t, 4H), 6.52 (d, 4H), 6.46 (d, 8H) |
| 41 | 962.24 | 7.86 (d, 2H), 7.78 (d, 2H), 7.74-7.71 (t, 4H), 7.55-7.53 (m, 6H), 7.40-7.39 (m, 6H), 7.33-7.31 (m, 4H), 7.30 (m, 10H), 7.08-7.00 (m, 4H) |

Synthesis of Compound 75

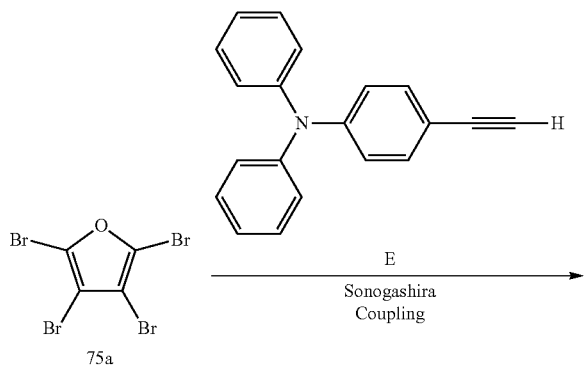

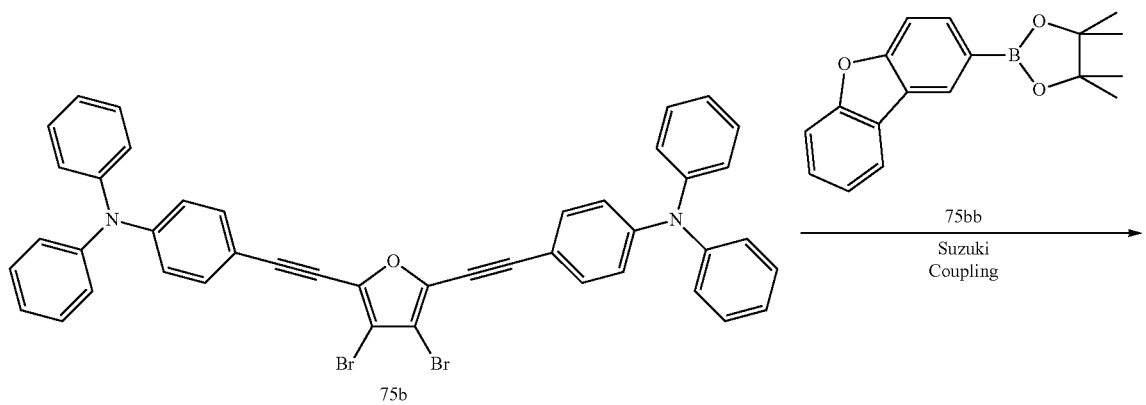

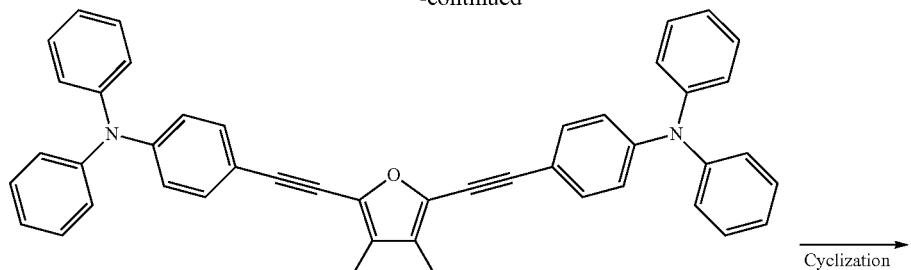

75c

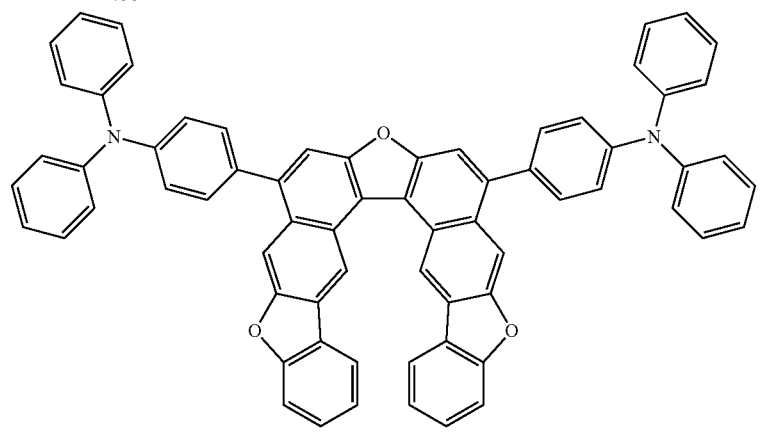

75

Synthesis Example 6

Synthesis of Intermediate 75B 5 g (1 eq) of Intermediate 75a, 2.26 g (0.15 eq) of Pd(PPh$_3$)$_4$, and 740 mg (0.30 eq) of CuI were put into a flask in a vacuum, which was then supplied with N$_2$ gas. After 100 mL of THF was added into the flask and then stirred, 58.2 mL (4.5 eq) of triethylamine and 7.7 g (2.2 eq) of Compound E were slowly dropwise added thereto, and then stirred at room temperature for about 2 hours in a N$_2$ atmosphere. After removing the solvent using a rotary evaporator, 100 mL of water was added to the resulting reaction solution, which was then extracted three times each with 100 mL of ethylether. An organic layer was collected and then dried using magnesium sulfate to evaporate the solvent. The residue was separated and purified using silica gel column chromatography to obtain 6.24 g of Intermediate 75b (Yield: 63%). This compound was identified using LC-MS. C$_{44}$H$_{28}$Br$_2$N$_2$O$_1$: M+760.05

Synthesis Example 7

Synthesis of Intermediate 75c 5 of Intermediate 75b, 4.25 g (2.2 eq) of Intermediate 75bb, 760 mg (0.1 eq) of Pd(PPh$_3$)$_4$, and 9.1 g (10 eq) of K$_2$CO$_3$ were dissolved in 100 mL of THF and 30 mL of distilled water to obtain a mixed solution, which was then refluxed for about 24 hours while being stirred after a temperature increase to about 120° C. The reaction solution was cooled to room temperature, followed by extraction three times each with 100 mL of water and 100 mL of diethylether. The organic phase was collected and then dried using magnesium sulfate to evaporate the solvent. The residue was separated and purified using silica gel column chromatography to obtain 4.24 g of Intermediate 25b (Yield: 69%). This compound was identified using LC-MS. C$_{68}$H$_{42}$N$_2$O$_3$: M+934.32

Synthesis Example 8

Synthesis of Compound 75

4.0 g of Intermediate 75c was dissolved in 100 mL of methylene chloride, and 13.1 mL (40 eq) of trifluoroacetic acid was dropwise added thereto and stirred at room temperature for about 1 hour. After completion of the reaction, the reaction solution was extracted three times each with 100 mL of water and 100 mL of diethylether. The organic layer was collected and then dried using magnesium sulfate, and the residue obtained by evaporating the solvent was separated and purified by silica gel column chromatography to obtain 3.6 g of Compound 75 (Yield: 90%). This compound was identified using LC-MS. C$_{68}$H$_{42}$N$_2$O$_3$: M+934.32

Synthesis of Compounds 48, 50, 56, 58, 66 and 81

Compounds 48, 50, 56, 58, 66, and 81 were synthesized as in Synthesis Examples 6 to 8 using the same equivalents of the reactants as in the synthesis of Compound 75. These compounds were identified using LC-MS and NMR.

| Comp. | LC-MS | NMR |
|---|---|---|
| 48 | 632.13 | 7.86 (d, 2H), 7.78 (d, 2H), 7.74 (d, 2H), 7.67-7.64 (m, 6H), 7.53 (d, 2H), 7.39 (t, 2H), 7.33-7.31 (m, 8H) |
| 50 | 482.16 | 9.15 (s, 2H), 8.45 (d, 2H), 7.72 (s, 2H), 7.50 (d, 2H), 7.37 (d, 4H), 6.83 (d, 4H), 3.73 (s, 6H) |
| 56 | 602.16 | 9.15 (s, 2H), 8.45 (d, 2H), 7.72 (s, 2H), 7.71 (s, 2H), 7.49-7.41 (m, 10H), 7.19 (t, 2H), 7.13 (t, 2H) |
| 58 | 434.05 | 8.81 (s, 2H), 8.55 (d, 2H), 7.97 (d, 2H), 7.55 (s, 2H), 7.44-7.40 (m, 4H), 7.29 (d, 2H) |
| 66 | 764.22 | 8.06 (d, 2H), 7.90-7.80 (m, 6H), 7.64-7.61 (t, 4H), 7.52 (s, 2H), 7.44-7.40 (m, 4H), 7.30 (m, 4H), 7.24 (t, 2H), 1.73 (s, 12H) |
| 75 | 934.32 | 7.64 (s, 2H), 7.49 (d, 4H), 7.42 (d, 4H), 7.23 (d, 4H), 7.19 (t, 2H), 7.13 (t, 2H), 7.01 (t, 8H), 6.62 (t, 4H), 6.52 (d, 4H), 6.46 (d, 8H) |
| 81 | 1080.38 | 7.77 (s, 2H), 7.64 (s, 2H), 7.55 (d, 6H), 7.46 (d, 2H), 7.40 (s, 6H), 7.30 (m, 22H), 7.08 (t, 4H), 7.00 (t, 4H) |

Synthesis of Compound 91

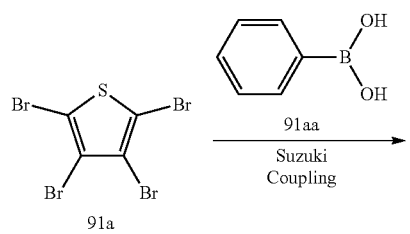

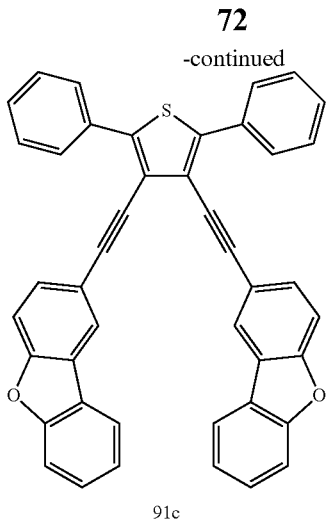

Synthesis Example 9

Synthesis of Intermediate 91b

Intermediate 91b was synthesized with a yield of about 63% as in Synthesis Example 3 using the same equivalents of the reactants, except that Intermediate 91a was used instead of Intermediate 25a. This compound was identified using LC-MS. $C_{16}H_{10}Br_2S_1$: M+393.88

Synthesis Example 10

Synthesis of Intermediate 91c

Intermediate 91c was synthesized with a yield of about 63% as in Synthesis Example 4 using the same equivalents of the reactants, except that Intermediate 91b was used instead of Intermediate 25b. This compound was identified using LC-MS. $C_{44}H_{24}O_2S_1$: M+616.15

Synthesis Example 11

Synthesis of Compound 91

Compound 91 was synthesized with a yield of about 94% as in Synthesis Example 5 using the same equivalents of the reactants, except that Intermediate 91c was used instead of Intermediate 25c. This compound was identified using LC-MS. $C_{44}H_{24}O_2S_1$: M+616.15

Synthesis of Compounds 88, 89, 97, 99, 103, 109, 115, and 121

Compounds 88, 89, 97, 99, 103, 109, 115, and 121 were synthesized as in Synthesis Examples 9 to 11 using the same equivalents of the reactants as in the synthesis of Compound 91. These compounds were identified using LC-MS and nuclear magnetic resonance (NMR).

| Comp. | LC-MS | NMR |
|---|---|---|
| 88 | 766.24 | 8.00 (s, 2H), 7.77 (s, 2H), 7.67 (d, 4H), 7.55 (d, 2H), 7.46 (d, 2H), 7.40 (d, 2H), 7.32-7.30 (m, 16H), 7.08 (t, 2H), 7.00 (t, 2H) |
| 89 | 770.28 | 8.00 (s, 2H), 7.67 (d, 4H), 7.32 (t, 4H), 7.23 (d, 4H), 7.01 (t, 8H), 6.62 (t, 4H), 6.52 (d, 4H), 6.46 (d, 8H) |
| 91 | 616.15 | 8.00 (s, 2H), 7.71 (s, 2H), 7.67 (d, 4H), 7.49-7.48 (m, 4H), 7.42-7.41 (t, 4H), 7.32 (t, 4H), 7.19 (t, 2H), 7.13 (t, 2H) |
| 97 | 650.09 | 9.15 (s, 2H), 8.45 (d, 2H), 7.86 (d, 2H), 7.78-7.72 (6H), 7.53-7.50 (m, 4H), 7.39 (t, 2H), 7.33-7.31 (m, 4H) |
| 99 | 508.06 | 8.00 (s, 2H), 7.40-7.37 (t, 6H), 7.29 (d, 2H), 6.83 (d, 4H), 3.73 (s, 6H) |
| 103 | 782.19 | 8.00 (s, 2H), 7.40 (d, 2H), 7.29 (d, 2H), 7.23 (d, 4H), 7.01 (t, 8H), 6.62 (t, 4H), 6.52 (d, 4H), 6.46 (d, 8H) |
| 109 | 998.37 | 8.06 (d, 2H), 8.00 (s, 2H), 7.83 (d, 2H), 7.77 (s, 2H), 7.61 (d, 2H), 7.55-7.52 (t, 4H), 7.46-7.40 (m, 6H), 7.30-7.24 (m, 14H), 7.08-7.00 (m, 4H), 1.73 (s, 12H) |
| 115 | 728.09 | 8.00 (s, 2H), 7.90 (d, 2H), 7.80 (, 2H), 7.40 (d, 2H), 7.49-7.42 (t, 6H), 7.30 (m, 4H), 7.19 (t, 4H), 7.13 (t, 2H) |
| 121 | 768.23 | 8.81 (s, 2H), 8.55 (d, 2H), 8.00 (s, 2H), 7.97 (s, 2H), 7.55 (d, 4H), 7.44-7.40 (t, 6H), 7.30 (m, 10H), 7.08-7.00 (m, 4H) |

Synthesis of Compound 138

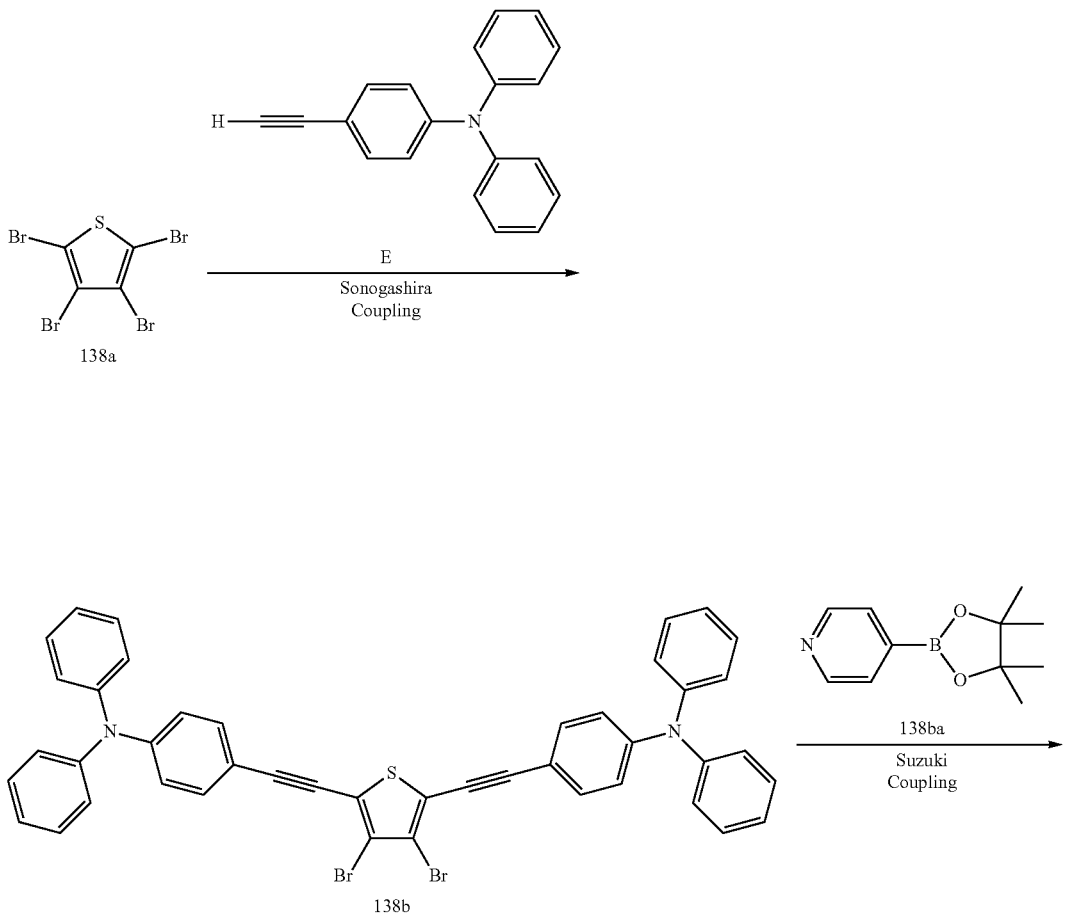

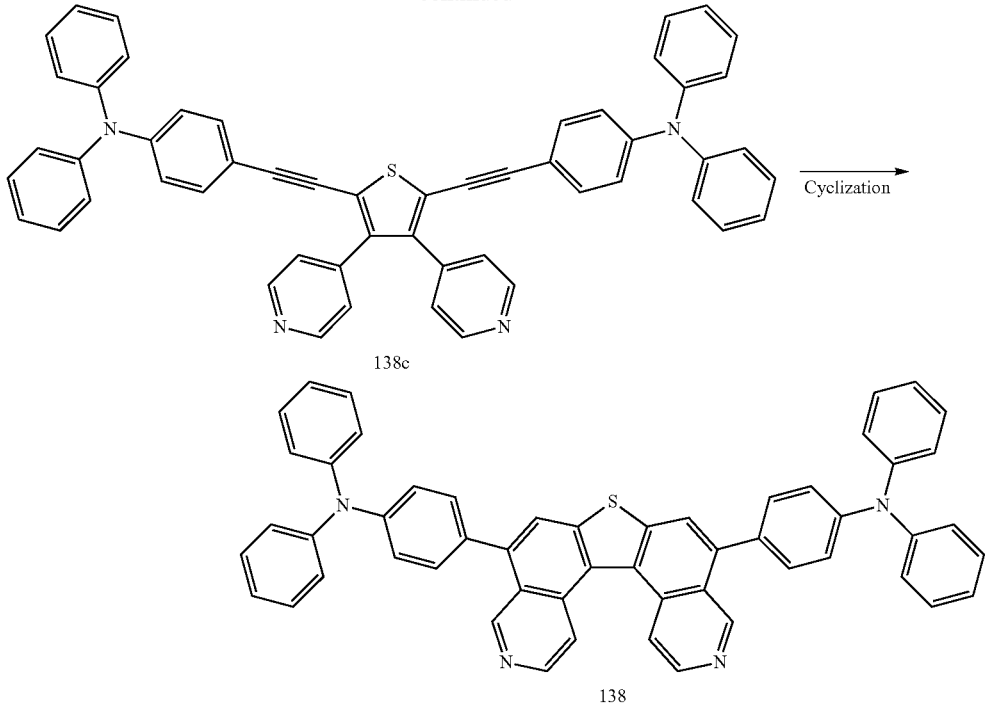

Synthesis Example 12

Synthesis of Intermediate 138b

Intermediate 138b was synthesized with a yield of about 58% as in Synthesis Example 6 using the same equivalents of the reactants, except that Intermediate 138a was used instead of Intermediate 75a. This compound was identified using LC-MS. $C_{16}H_{10}Br_2S_1$: M+393.88

Synthesis Example 13

Synthesis of Intermediate 138c

Intermediate 138c was synthesized with a yield of about 60 as in Synthesis Example 7 using the same equivalents of the reactants, except that Intermediate 138b was used instead of Intermediate 75b. This compound was identified using LC-MS. $C_{54}H_{36}N_4S_1$: M+772.27

Synthesis Example 14

Synthesis of Compound 138

Compound 138 was synthesized with a yield of about 91% as in Synthesis Example 8 using the same equivalents of the reactants, except that Intermediate 138c was used instead of Intermediate 75c. This compound was identified using LC-MS. $C_{54}H_{36}N_4S_1$: M+772.27

Synthesis of Compounds 129, 130, 146, 154, 155 and 163

Compounds 129, 130, 146, 154, 155 and 163 were synthesized as in Synthesis Examples 12 to 14 using the same equivalents of the reactants as in the synthesis of Compound 138. These compounds were identified using LC-MS and nuclear magnetic resonance (NMR).

| Comp. | LC-MS | NMR |
|---|---|---|
| 129 | 548.07 | 8.08 (s, 2H), 7.90 (d, 2H), 7.80 (d, 2H), 7.67 (d, 4H), 7.40 (s, 2H), 7.32-7.30 (8H) |
| 130 | 766.24 | 8.08 (s, 2H), 7.77 (s, 2H), 7.67 (d, 4H), 7.55 (d, 2H), 7.46 (d, 2H), 7.40 (d, 2H), 7.32-7.30 (m, 16H), 7.08 (t, 2H), 7.00 (t, 2H) |
| 138 | 772.27 | 9.15 (s, 2H), 8.45 (d, 2H), 7.72 (s, 2H), 7.50 (d, 2H), 7.23 (d, 4H), 7.01 (t, 8H), 6.62 (t, 4H), 6.52 (d, 4H), 6.46 (d, 8H) |
| 146 | 660.02 | 8.08 (s, 2H), 7.86 (d, 2H), 7.78-7.74 (m, 4H), 7.53 (d, 2H), 7.40-7.39 (m, 4H), 7.33-7.29 (m, 6H) |
| 154 | 848.27 | 8.08-8.06 (t, 4H), 7.83 (s, 2H), 7.71 (s, 2H), 7.61 (d, 2H), 7.52-7.41 (m, 12H), 7.24 (t, 2H), 7.19 (t, 2H), 7.13 (t, 2H), 1.73 (s, 12H) |
| 155 | 676.17 | 8.08 (s, 2H), 7.49 (t, 4H), 7.42 (t, 4H), 7.37 (d, 4H), 7.19 (t, 2H), 7.13 (t, 2H), 6.83 (d, 4H), 3.73 (s, 6H) |
| 163 | 768.23 | 8.81 (s, 2H), 8.55 (d, 2H), 8.08 (s, 2H), 7.97 (d, 2H), 7.55 (d, 4H), 7.44-7.40 (t, 6H), 7.30 (m, 10H), 7.08 (t, 2H), 7.00 (t, 2H) |

Example 1

To manufacture an anode, a corning 15 $\Omega/cm^2$ (1200 Å) ITO glass substrate was cut to a size of 50 mm×50 mm×0.7 mm and then sonicated in isopropyl alcohol and pure water each for five minutes. Then, the substrate was cleaned by ultrasonication, followed by ultraviolet (UV) irradiation for about 30 minutes, and washing by exposure to ozone. The resulting glass substrate was loaded into a vacuum deposition device.

2-TNATA was vacuum-deposited on the ITO glass substrate to form an HIL having a thickness of 600 Å on the anode, and then NPS was vacuum-deposited on the HIL to form a HTL having a thickness of 300 Å.

Compound 28 as a host and DPVBi as a blue fluorescent dopant were co-deposited on the HTL in a weight ratio of about 98:2 to form an EML having a thickness of about 300 Å.

Alq3 was deposited on the EML to form an ETL having a thickness of 300.

LiF was vacuum-deposited on the ETL to form an EIL having a thickness of about 10 Å and Al was vacuum-deposited on the EIL to form a cathode having a thickness of about 3000 Å, thereby completing the manufacture of an organic light-emitting device having the LiF/Al electrodes.

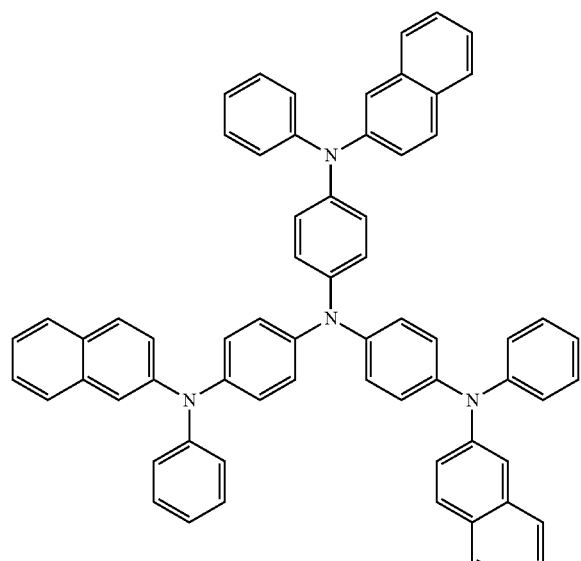

2-TNATA

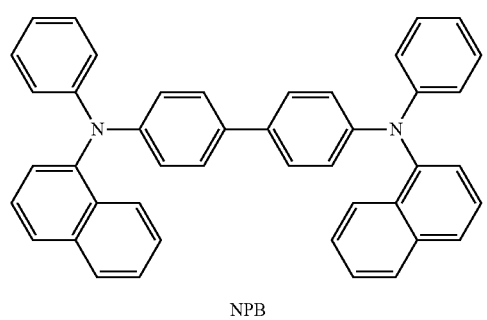

NPB

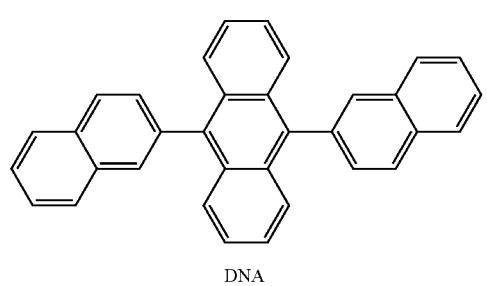

DNA

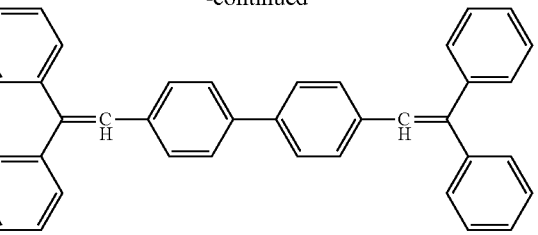

DPVBi

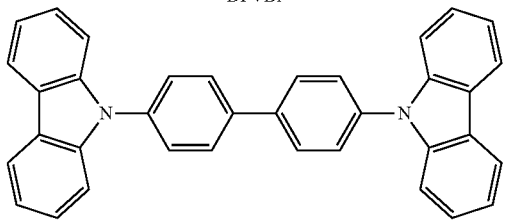

CBP

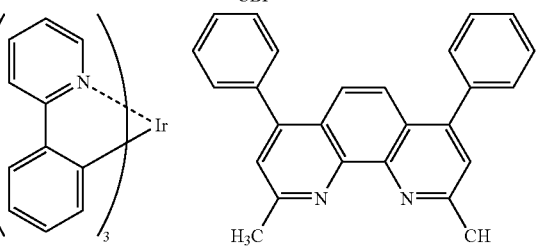

Irppy

BCP

Example 2

An organic light-emitting device was manufactured as in Example 1, except that Compound 48 was used instead of Compound 28 to form the EML.

Example 3

An organic light-emitting device was manufactured as in Example 1, except that Compound 88 (as a green phosphorescent host) and Irppy (as a green phosphorescent dopant) were co-deposited in a weight ratio of 91:9 to form an EML having a thickness of about 300 Å, and then, BCP (as a hole blocking compound) was vacuum-deposited on the EML to form a HBL having a thickness of about 50 Å.

Example 4

An organic light-emitting device was manufactured as in Example 3, except that Compound 91 was used instead of Compound 88 to form the EML.

Example 5

An organic light-emitting device was manufactured as in Example 1, except that DNA was used instead of Compound 28 to form the EML, and Compound 75 was used instead of NPB to form the HTL.

Example 6

An organic light-emitting device was manufactured as in Example 5, except that Compound 89 was used instead of Compound 75 to form the HTL.

Example 7

An organic light-emitting device was manufactured as in Example 1, except that Compound 75 was used instead of NPB to form the HTL.

Example 8

An organic light-emitting device was manufactured as in Example 1, except that Compound 89 was used instead of NPB to form the HTL.

Comparative Example 1

An organic light-emitting device was manufactured as in Example 1, except that DNA was used instead of Compound 28 to form the EML.

Comparative Example 2

An organic light-emitting device was manufactured as in Example 3, except that CBP was used instead of Compound 88 to form the EML.

Evaluation Example

Driving voltage, luminance, luminescent efficiency, and lifetime of the organic light-emitting devices of Examples 1 to 8 and Comparative Examples 1 and 2 were measured using a PR650 (Spectroscan) source measurement unit (available from PhotoResearch, Inc.). The results are shown in Table 1 below.

Referring to Table 1, the organic light-emitting devices of Examples 1 to 8 are found to have lower driving voltages, greatly improved luminescent efficiency, and remarkable improvements in luminance and lifetime, as compared with the organic light-emitting device of Comparative Example 1.

In particular, the organic light-emitting device of Example 8 had a lower driving voltage by about 0.8V, and a higher luminescent efficiency by about 160%, as compared with the organic light-emitting device of Comparative Example 1.

The organic light-emitting device of Example 4 had a lower driving voltage by about 1.1V, a higher luminescent efficiency by about 170%, and about 1.5 times longer lifetime, as compared with the organic light-emitting device of Comparative Example 2.

Therefore, the organic light-emitting devices of Examples 1 to 8 are found to have high efficiency, low voltage, high luminance, and long lifetimes, as compared with existing organic light-emitting devices.

According to the one or more embodiments, the heterocyclic compounds of Formula 1 above may have a glass transition temperature that is high enough to prevent crystallization, and improved electrical characteristics, high charge transport capability, and high emission capability. The heterocyclic compound of Formula 1 may be used as a light-emitting material in any color, such as red, green, blue, or white, or as an electron transporting material for fluorescent or phosphorescent organic light-emitting devices, and exhibits improved light-emitting characteristics.

According to the one or more embodiments of the present invention, the organic light-emitting device may include the heterocyclic compound of Formula 1 above as a light-emitting material or an electron-transporting material, and thus has high efficiency, low voltage, high luminance, and a long lifetime, as compared with existing light-emitting devices.

According to embodiments, an organic light-emitting display apparatus including the organic light-emitting device

TABLE 1

| Example | Driving voltage (V) | Current density ($mA/cm^2$) | Luminance ($cd/m^2$) | Luminescent efficiency (cd/A) | Emission color | T95 lifetime (hr @100 $mA/cm^2$) |
|---|---|---|---|---|---|---|
| Example 1 | 6.11 | 50 | 2,283 | 4.57 | blue | 28 |
| Example 2 | 6.08 | 50 | 2,237 | 4.47 | blue | 31 |
| Example 3 | 5.37 | 50 | 17,353 | 34.7 | blue | 88 |
| Example 4 | 5.63 | 50 | 18,409 | 36.8 | blue | 90 |
| Example 5 | 6.27 | 50 | 2,258 | 4.52 | blue | 29 |
| Example 6 | 6.31 | 50 | 2,345 | 4.69 | blue | 27 |
| Example 7 | 6.29 | 50 | 2,381 | 4.76 | blue | 34 |
| Example 8 | 6.15 | 50 | 2,404 | 4.81 | blue | 32 |
| Comp. Example 1 | 7.35 | 50 | 1,522 | 3.04 | blue | 15 |
| Comp. Example 2 | 6.8 | 50 | 10,902 | 21.8 | green | 60 | may have an increased lifetime and increased power efficiency with reduced power consumption.

While the present invention has been illustrated and described with reference to exemplary embodiments thereof, it will be understood by those of ordinary skill in the art that various changes may be made to the described embodiments without departing from the spirit and scope of the present invention as defined by the following claims.

What is claimed is:

1. A heterocyclic compound represented by Formula 2a or 2b:

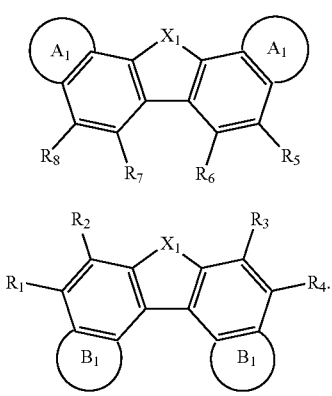

Formula 2a

Formula 2b wherein:
$X_1$ is an oxygen atom (—O—) or a sulfur atom (—S—); and
$R_1$ to $R_8$ are each independently one of a hydrogen atom, a deuterium atom, a halogen atom, a hydroxyl group, a cyano group, an amino group, a nitro group, a carboxyl group, a substituted or unsubstituted $C_3$-$C_{30}$ alkynyl group, a substituted or unsubstituted $C_2$-$C_{30}$ alkenyl group, a substituted or unsubstituted $C_2$-$C_{30}$ alkynyl group, a substituted or unsubstituted $C_1$-$C_{30}$ alkoxy group, a substituted or unsubstituted $C_3$-$C_{30}$ cycloalkyl group, a substituted or unsubstituted $C_3$-$C_{30}$ cycloalkenyl group, a substituted or unsubstituted $C_6$-$C_{30}$ aryl group, a substituted or unsubstituted $C_6$-$C_{30}$ aryloxy group, a substituted or unsubstituted $C_6$-$C_{30}$ arylthio group, a substituted or unsubstituted $C_2$-$C_{30}$ heteroaryl group, or a —$N(Q_1)(Q_2)$ group,
wherein at least one of R1 or R2, at least one of R3 or R4, at least one of R5 or R6, and at least one of R7 or R8 are independently one of a deuterium atom, a halogen atom, a cyano group, an amino group, a nitro group, a carboxyl group, a substituted or unsubstituted $C_1$-$C_{30}$ alkyl group, a substituted or unsubstituted $C_2$-$C_{30}$ alkenyl group, a substituted or unsubstituted $C_2$-$C_{30}$ alkynyl group, a substituted or unsubstituted $C_3$-$C_{30}$ cycloalkyl group, a substituted or unsubstituted $C_3$-$C_{30}$ cycloalkenyl group, a substituted or unsubstituted $C_6$-$C_{30}$ aryl group, a substituted or unsubstituted $C_6$-$C_{30}$ aryloxy group, a substituted or unsubstituted $C_6$-$C_{30}$ arylthio group, a substituted or unsubstituted $C_2$-$C_{30}$ heteroaryl group, or a —$N(Q_1)(Q_2)$ group,
wherein at least one of $R_2$ or $R_3$ is independently one of a deuterium atom, a halogen atom, a cyano group, an amino group, a nitro group, a carboxyl group, a substituted or unsubstituted $C_1$-$C_{30}$ alkyl group, a substituted or unsubstituted $C_2$-$C_{30}$ alkenyl group, a substituted or unsubstituted $C_2$-$C_{30}$ alkynyl group, a substituted or unsubstituted $C_3$-$C_{30}$ cycloalkyl group, a substituted or unsubstituted $C_3$-$C_{30}$ cycloalkenyl group, a substituted or unsubstituted $C_6$-$C_{30}$ aryloxy group, a substituted or unsubstituted $C_6$-$C_{30}$ arylthio group, a substituted or unsubstituted $C_2$-$C_{30}$ heteroaryl group, a substituted or unsubstituted biphenyl group, a substituted or unsubstituted naphthyl group, a substituted or unsubstituted anthryl group, a substituted or unsubstituted phenanthrenyl group, a substituted or unsubstituted pyrenyl group, a substituted or unsubstituted chrysenyl group, a substituted or unsubstituted naphthacenyl group, a substituted or unsubstituted fluorenyl group, or $N(Q_1)(Q_2)$ group,
wherein $Q_1$ and $Q_2$ are each independently one of a hydrogen atom, a deuterium atom, a halogen atom, a hydroxyl group, a cyano group, an amino group, a nitro group, a carboxyl group, a substituted or unsubstituted $C_1$-$C_{30}$ alkyl group, a substituted or unsubstituted $C_2$-$C_{30}$ alkenyl group, a substituted or unsubstituted $C_2$-$C_{30}$ alkynyl group, a substituted or unsubstituted $C_1$-$C_{30}$ alkoxy group, a substituted or unsubstituted $C_3$-$C_{30}$ cycloalkyl group, a substituted or unsubstituted $C_3$-$C_{30}$ cycloalkenyl group, a substituted or unsubstituted $C_6$-$C_{30}$ aryl group, a substituted or unsubstituted $C_6$-$C_{30}$ aryloxy group, a substituted or unsubstituted $C_6$-$C_{30}$ arylthio group, or a substituted or unsubstituted $C_2$-$C_{30}$ heteroaryl group, and
wherein rings $A_1$ and rings $B_1$ are each independently one of a substituted or unsubstituted $C_6$-$C_{30}$ aromatic ring or a substituted or unsubstituted $C_2$-$C_{30}$ heteroaromatic ring.

2. The heterocyclic compound of claim 1, wherein the rings $A_1$ and the rings $B_1$ are each independently one of a substituted or unsubstituted benzene ring, a substituted or unsubstituted anthracene ring, a substituted or unsubstituted phenanthrene ring, a substituted or unsubstituted fluorene ring, a substituted or unsubstituted pyridine ring, a substituted or unsubstituted carbazole ring, a substituted or unsubstituted thiophene ring, a substituted or unsubstituted dibenzothiophene ring, or a substituted or unsubstituted dibenzofuran ring.

3. The heterocyclic compound of claim 1, wherein the rings $A_1$ and the rings $B_1$ are each independently a group represented by one of Formulae 3a to 3f:

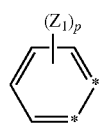

Formula 3a

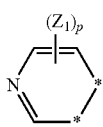

Formula 3b

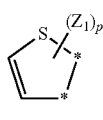

Formula 3c

-continued

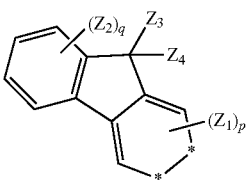

Formula 3d

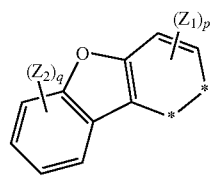

Formula 3e

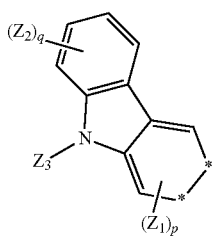

Formula 3f wherein:

$Z_1$ to $Z_4$ are each independently one of a hydrogen atom, a deuterium atom, a halogen atom, a cyano group, a substituted or unsubstituted methyl group, a substituted or unsubstituted ethyl group, a substituted or unsubstituted propyl group, a substituted or unsubstituted butyl group, a substituted or unsubstituted phenyl group, or a substituted or unsubstituted biphenyl group;

p and q are each independently an integer of from 2 to 4; and

* indicates a binding site of the ring $A_1$ or ring $B_1$ to the heterocyclic compound.

4. The heterocyclic compound of claim 1, wherein the rings $A_1$ and the rings $B_1$ are each independently a group represented by one of Formulae 4a to 4f:

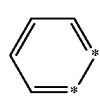

Formula 4a

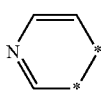

Formula 4b

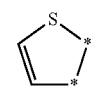

Formula 4c

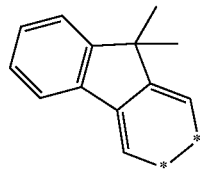

Formula 4d

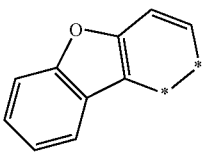

Formula 4e

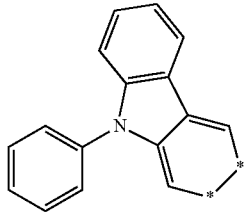

Formula 4f wherein * indicates a binding site of the ring $A_1$ or ring $B_1$ to the heterocyclic compound.

5. The heterocyclic compound of claim 1, wherein $R_1$ to $R_8$ are each independently one of a hydrogen atom, a deuterium atom, a halogen atom, a cyano group, a substituted or unsubstituted methyl group, a substituted or unsubstituted ethyl group, a substituted or unsubstituted propyl group, a substituted or unsubstituted butyl group, a substituted or unsubstituted phenyl group, a substituted or unsubstituted biphenyl group, a substituted or unsubstituted naphthyl group, a substituted or unsubstituted anthryl group, a substituted or unsubstituted phenanthrenyl group, a substituted or unsubstituted pyrenyl group, a substituted or unsubstituted chrysenyl group, a substituted or unsubstituted naphthacenyl group, a substituted or unsubstituted fluorenyl group, a substituted or unsubstituted pyridinyl group, a substituted or unsubstituted bipyridinyl group, a substituted or unsubstituted pyrazinyl group, a substituted or unsubstituted pyrimidinyl group, a substituted or unsubstituted pyridazinyl group, a substituted or unsubstituted carbazolyl group, a substituted or unsubstituted benzothiophenyl group, a substituted or unsubstituted dibenzothiophenyl group, a substituted or unsubstituted dibenzofuranyl group, or a group represented by -ph-N($Q_3$)($Q_4$), wherein at least one of R1 or R2, at least one of R3 or R4, at least one of R5 or R6, and at least one of R7 or R8 are each independently one of a deuterium atom, a halogen atom, a cyano group, a substituted or unsubstituted methyl group, a substituted or unsubstituted ethyl group, a substituted or unsubstituted propyl group, a substituted or unsubstituted butyl group, a substituted or unsubstituted phenyl group, a substituted or unsubstituted biphenyl group, a substituted or unsubstituted naphthyl group, a substituted or unsubstituted anthryl group, a substituted or unsubstituted phenanthrenyl group, a substituted or unsubstituted pyrenyl group, a substituted or unsubstituted chrysenyl group, a substituted or unsubstituted naphthacenyl group, a substituted or unsubstituted fluorenyl group, a substituted or unsubstituted pyridinyl group, a substituted or unsubstituted bipyridinyl group, a substituted or unsubstituted pyrazinyl group, a substituted or unsubstituted pyrimidinyl group, a substituted or unsubstituted pyridazinyl group, a substituted or unsubstituted carbazolyl group, a substituted or unsubstituted benzothiophenyl group, a substituted or unsubstituted dibenzothiophenyl group, a substituted or unsubstituted dibenzofuranyl group, or a group represented by -ph-N($Q_3$)($Q_4$), wherein $Q_3$ and $Q_4$ are each independently one of a substituted or unsubstituted $C_6$-$C_{30}$ aryl group or a substituted or unsubstituted $C_2$-$C_{30}$ heteroaryl group.

6. The heterocyclic compound of claim 1, wherein $R_1$, $R_4$, $R_5$ and $R_8$ are each independently one of a substituted or unsubstituted phenyl group, a substituted or unsubstituted biphenyl group, a substituted or unsubstituted fluorenyl group, a substituted or unsubstituted pyridinyl group, a substituted or unsubstituted carbazolyl group, a substituted or unsubstituted benzothiophenyl group, a substituted or unsubstituted dibenzothiophenyl group, a substituted or unsubstituted dibenzofuranyl group, or a group represented by -ph-N(ph)(ph); and $R_2$, $R_3$, $R_6$ and $R_7$ are each independently a hydrogen atom or a deuterium atom.

7. The heterocyclic compound of claim 6, wherein $R_1$, $R_4$, $R_5$ and $R_8$ are each independently a group represented by one of Formulae 5a to 5g:

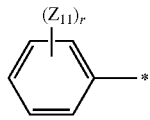

Formula 5a

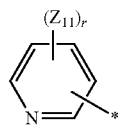

Formula 5b

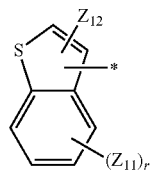

Formula 5c

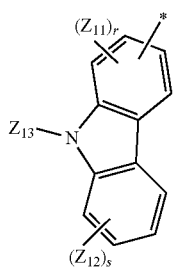

Formula 5d

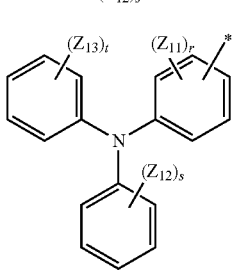

Formula 5e

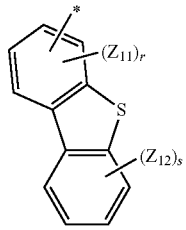

Formula 5f

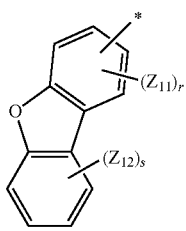

Formula 5g wherein:
$Z_{11}$ to $Z_{13}$ are each independently one of a hydrogen atom, a deuterium atom, a halogen atom, a cyano group, a substituted or unsubstituted methyl group, a substituted or unsubstituted ethyl group, a substituted or unsubstituted propyl group, a substituted or unsubstituted butyl group, a substituted or unsubstituted methoxy group, a substituted or unsubstituted ethoxy group, a substituted or unsubstituted propoxy group, a substituted or unsubstituted butoxy group, a substituted or unsubstituted phenyl group, or a substituted or unsubstituted biphenyl group;

r, s, and t are each independently an integer from 1 to 5; and

* indicates a binding site of $R_1$, $R_4$, $R_5$ and $R_8$ to the heterocyclic compound.

8. The heterocyclic compound of claim 6, wherein $R_1$, $R_4$, $R_5$ and $R_8$ are each independently a group represented by one of Formulae 6a to 6g:

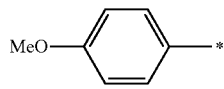

Formula 6a

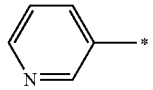

Formula 6b

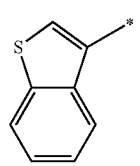

Formula 6c

Formula 6d
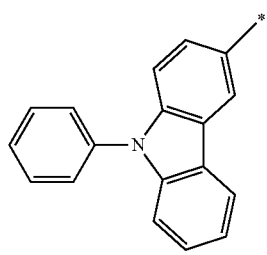
Formula 6e
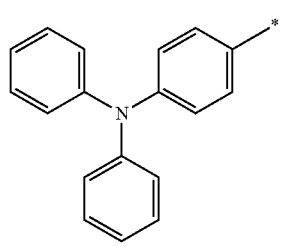
Formula 6f
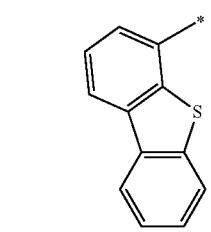
Formula 6g
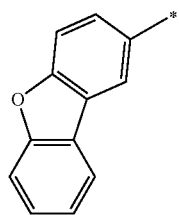
wherein * indicates a binding site of $R_1$, $R_4$, $R_5$ and $R_8$ to the heterocyclic compound.
9. The heterocyclic compound of claim 1, wherein the heterocyclic compound is one of Compounds 1 to 168:
1
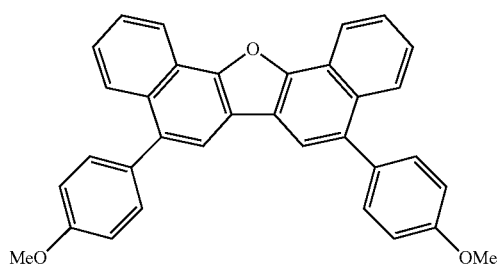
2
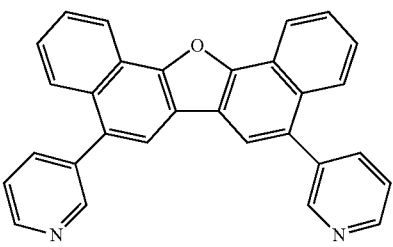
3
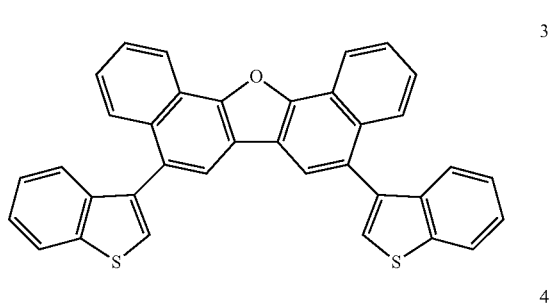
4
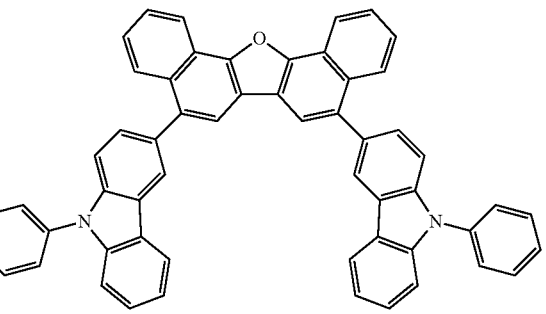
5
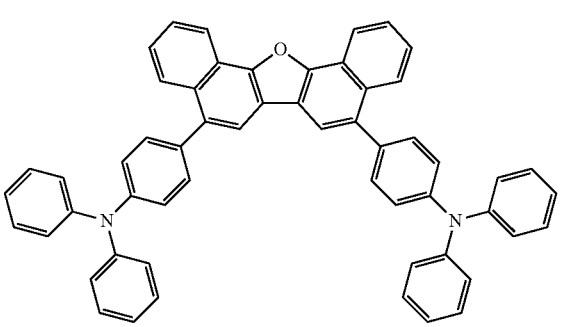
6
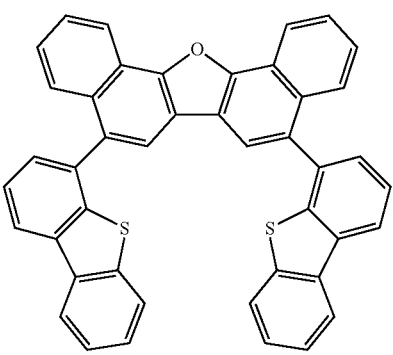

-continued
7
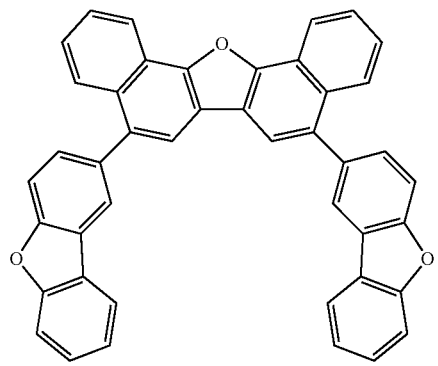
8
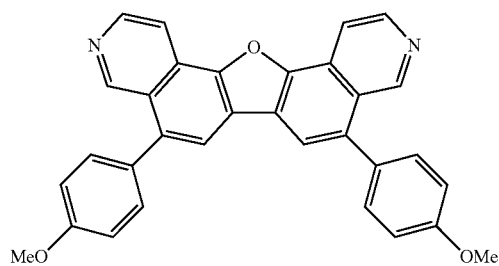
9
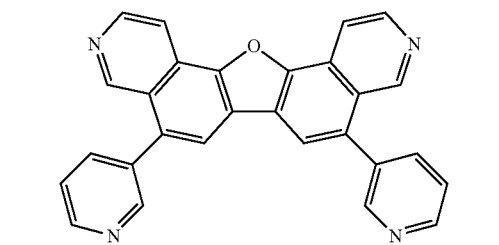
10
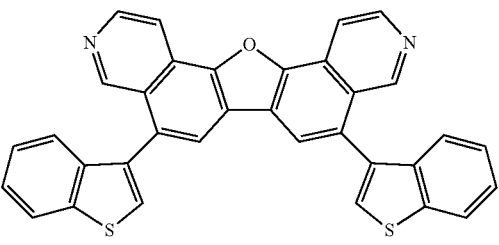
11
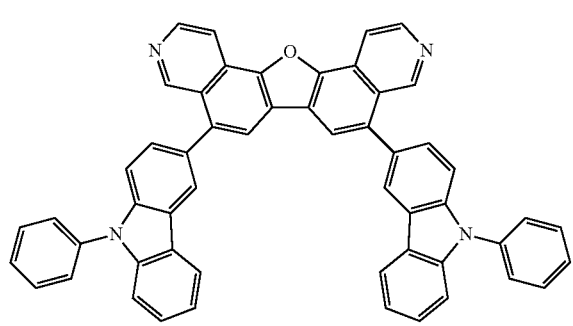
-continued
12
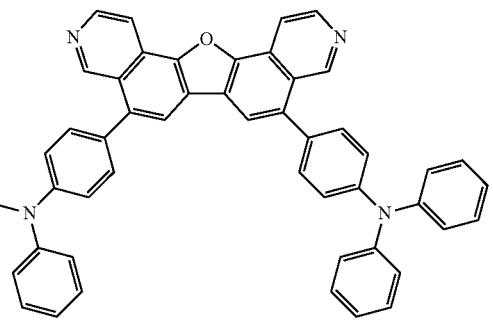
13
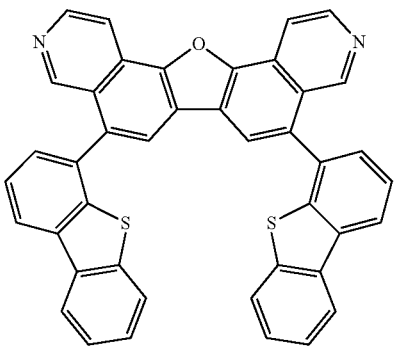
14
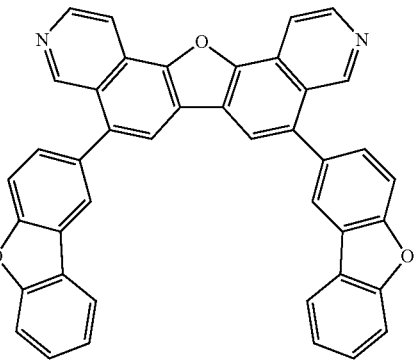
15
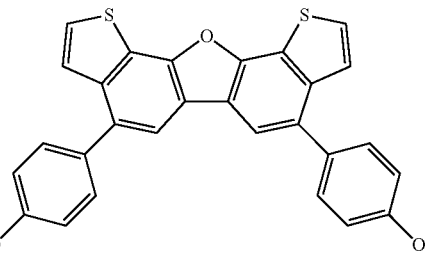
16
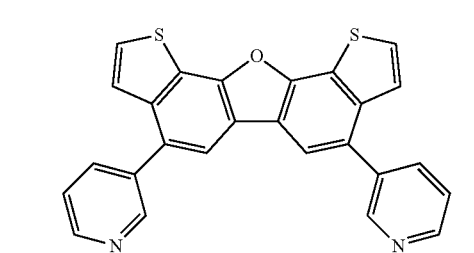

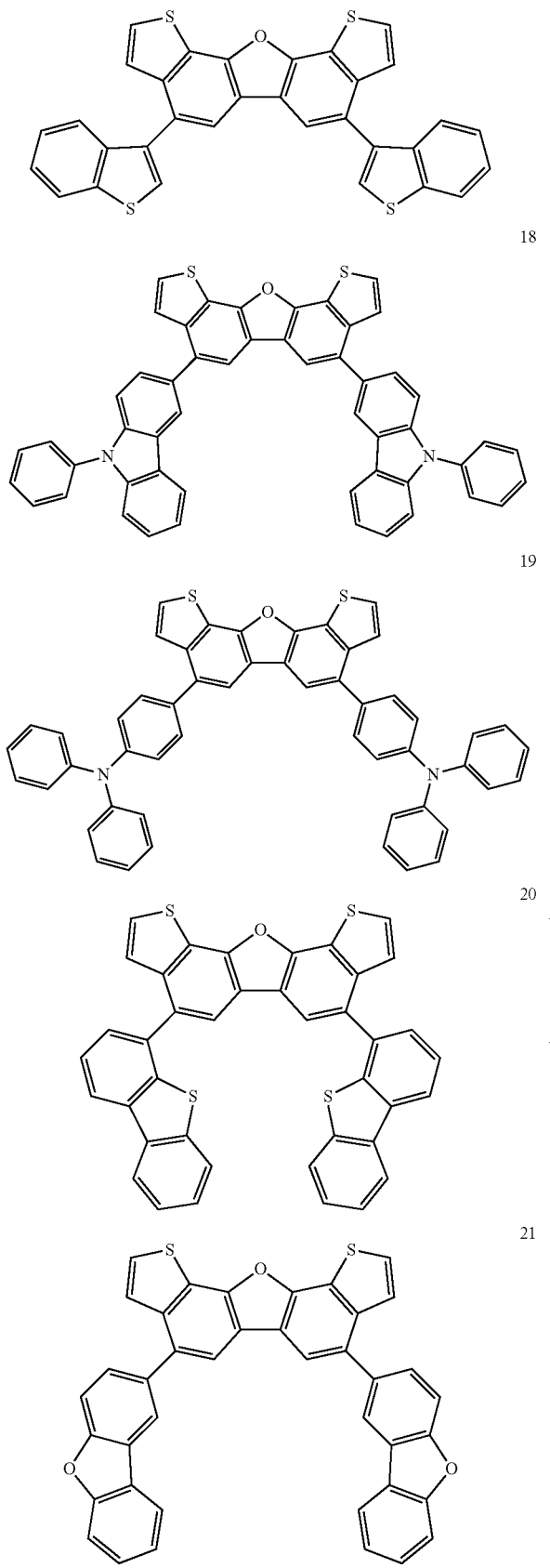
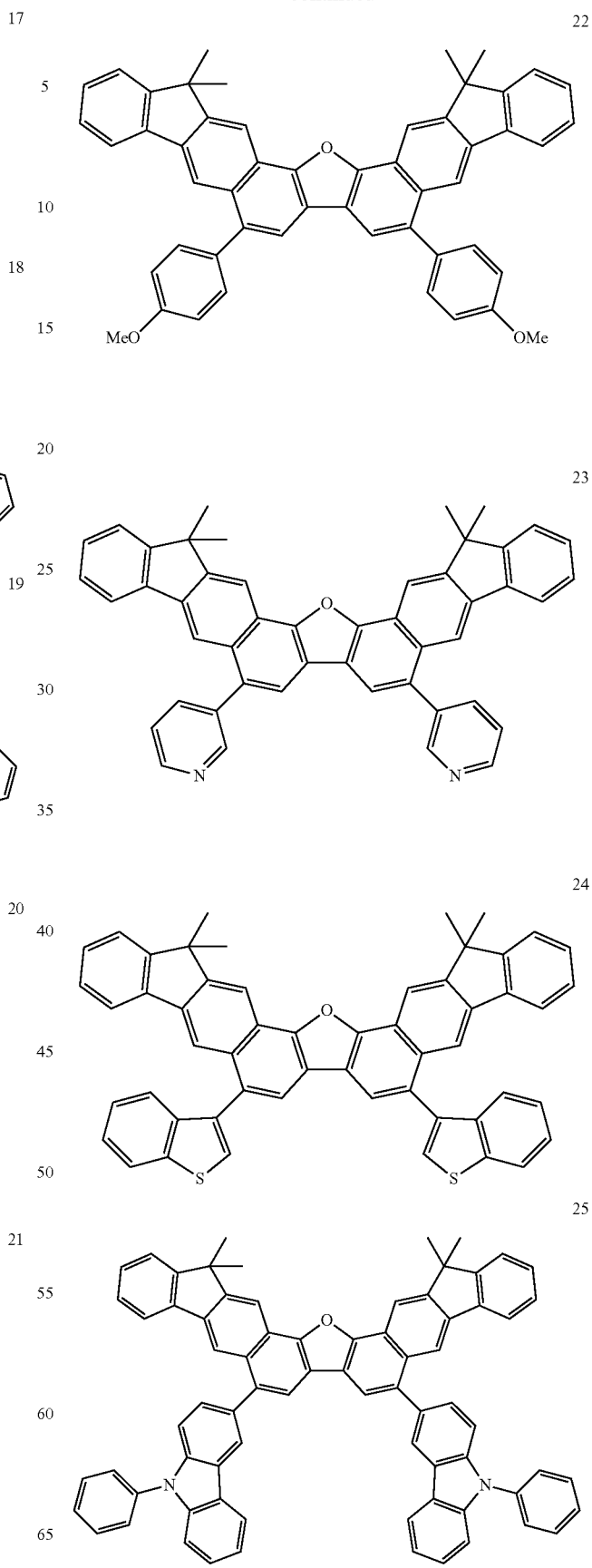

93
-continued
26
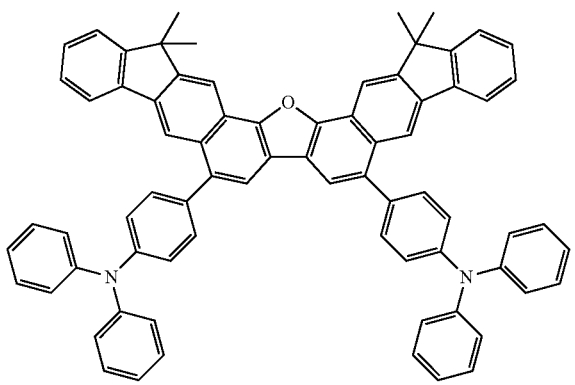
27
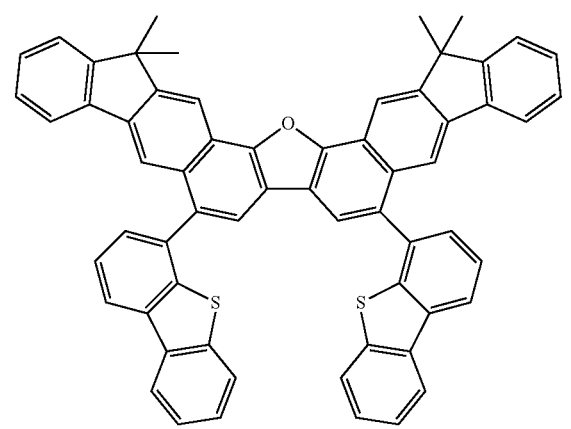
28
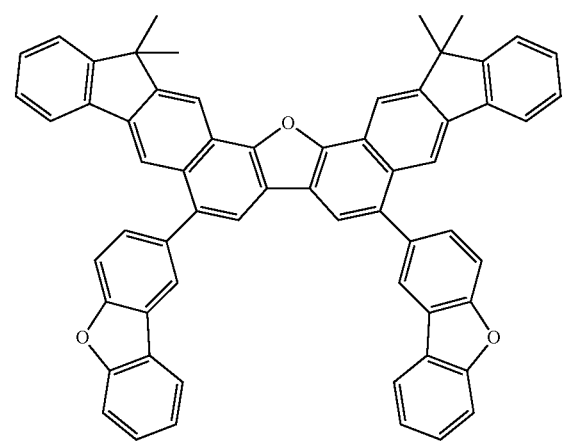
29
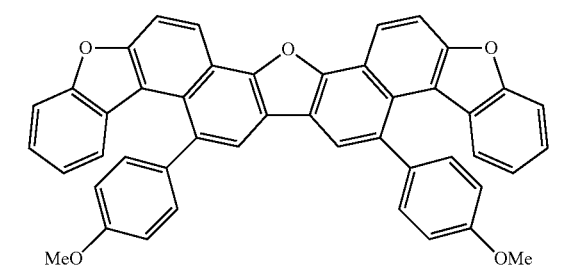
94
-continued
30
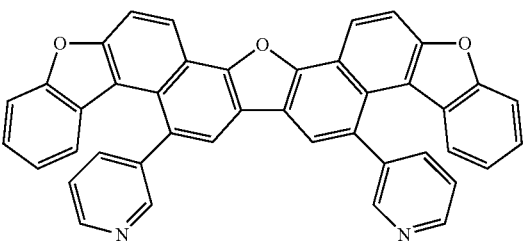
31
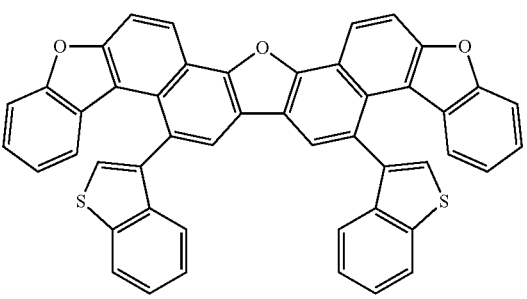
32
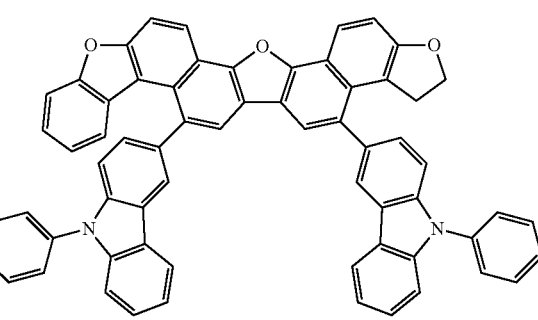
33
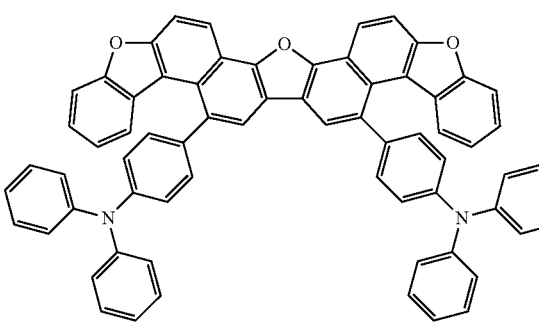
34
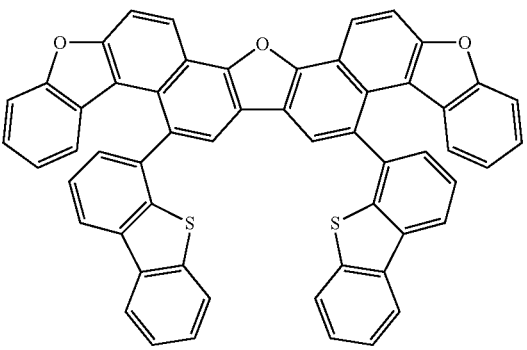

35
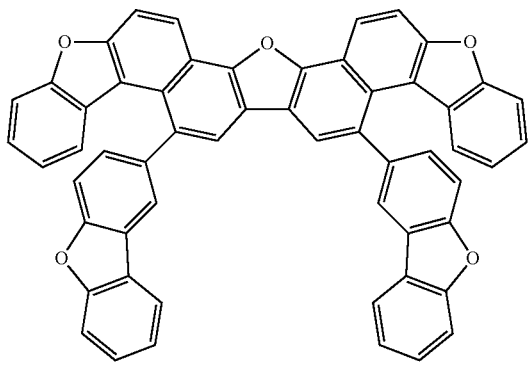
36
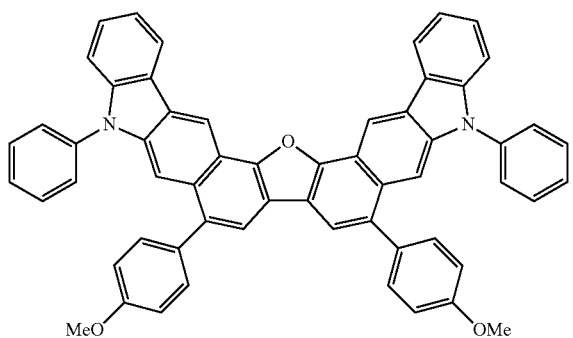
37
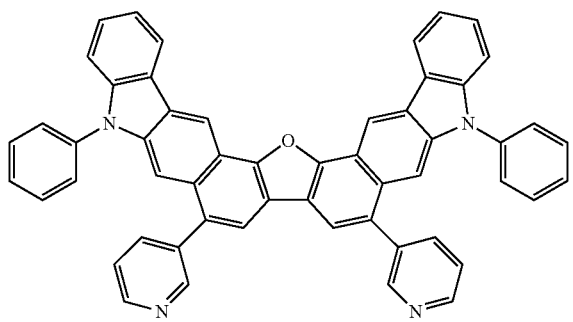
38
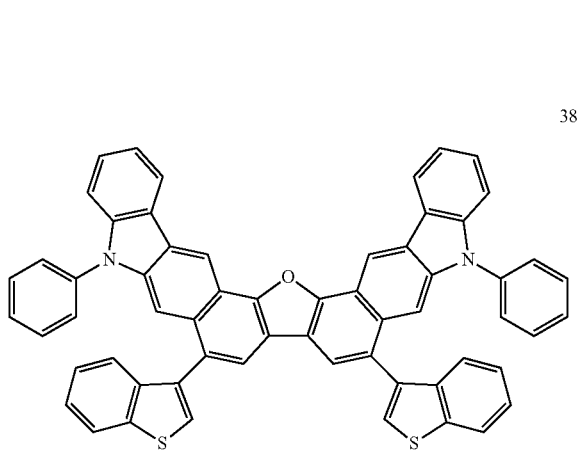
39
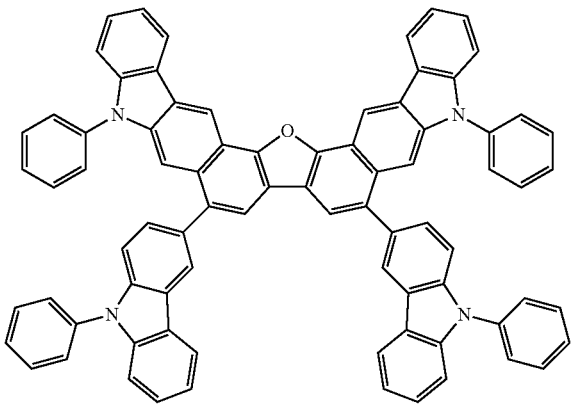
40
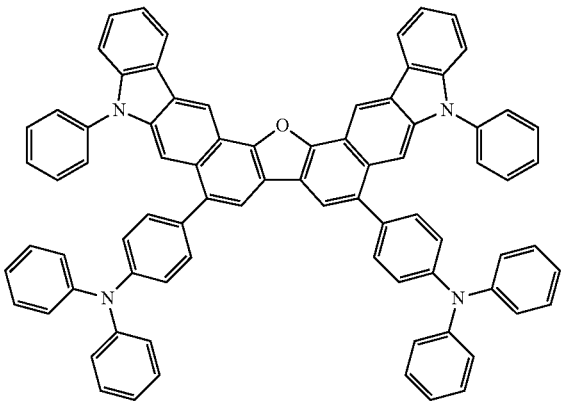
41
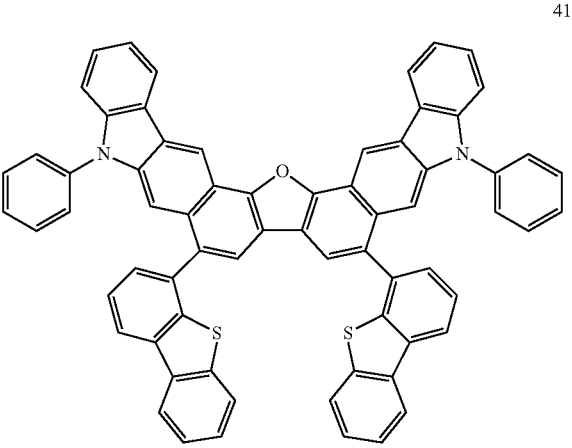

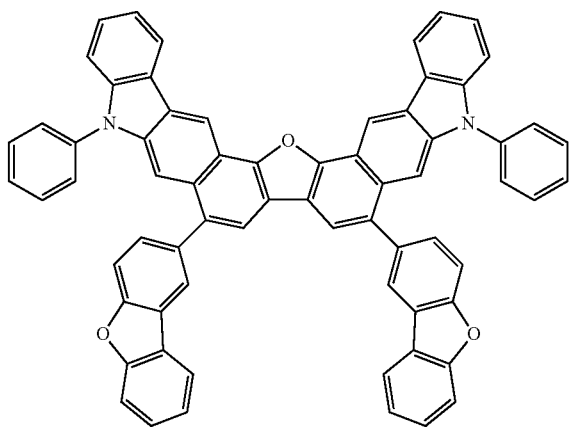
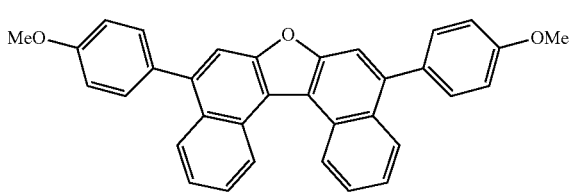
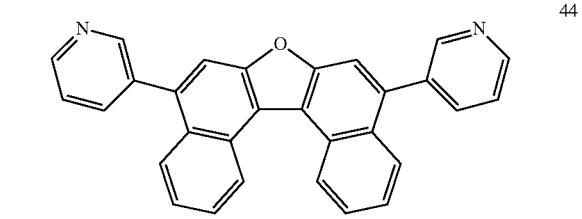
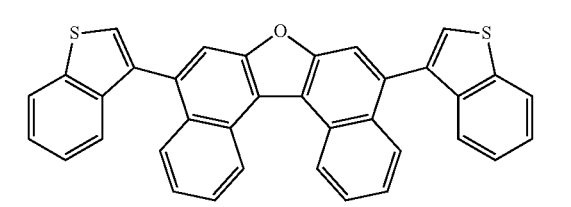
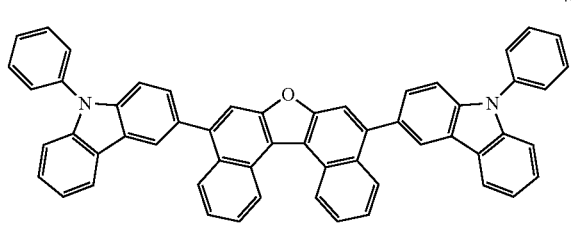
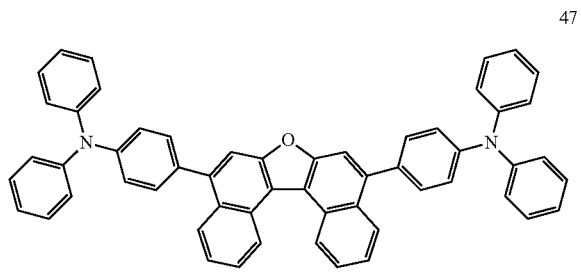
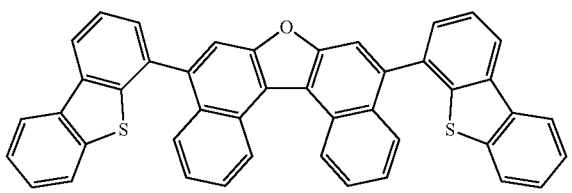

-continued
54
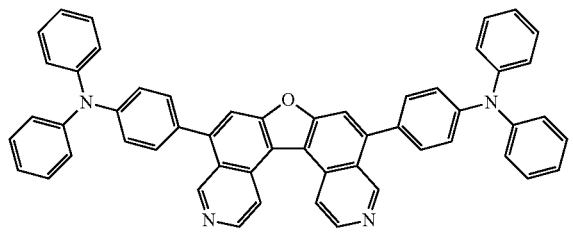
55
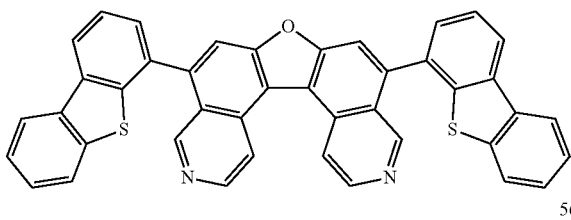
56
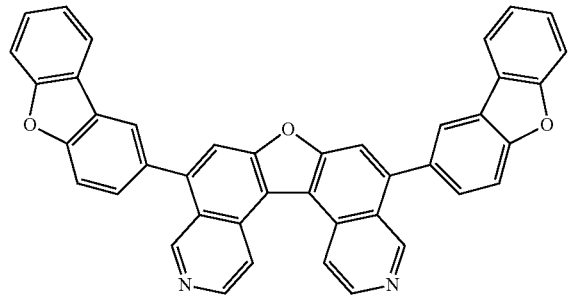
57
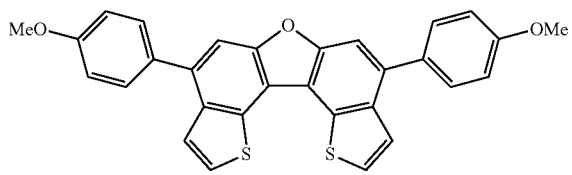
58
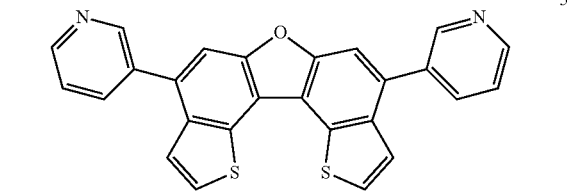
59
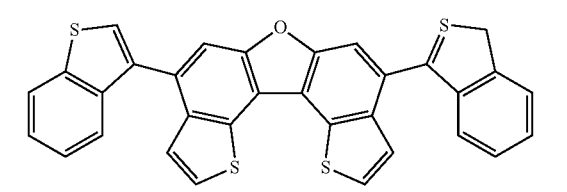
60
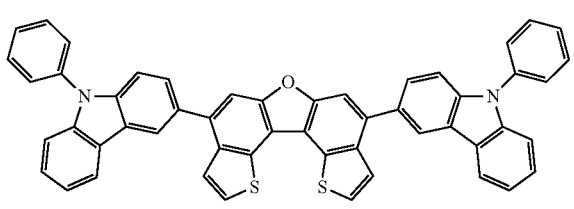
-continued
61
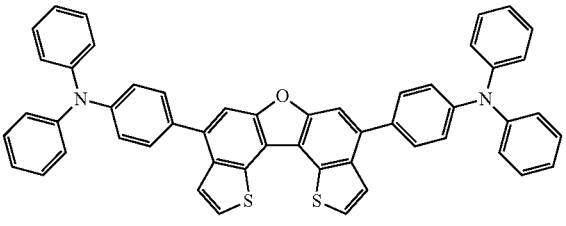
62
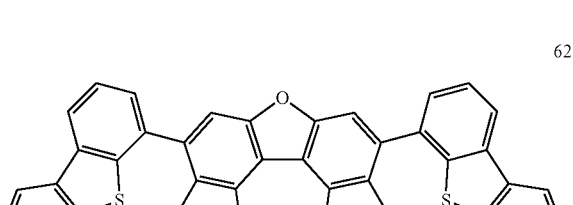
63
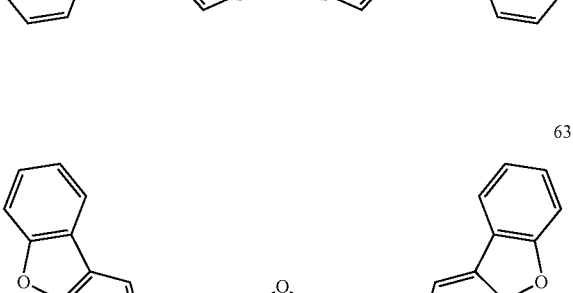
64
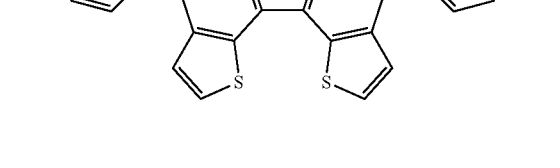
65
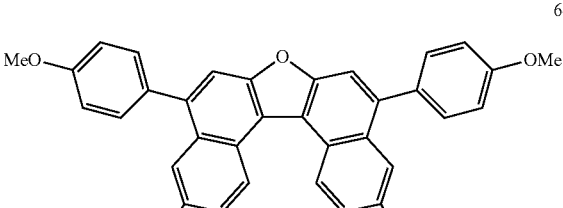

101
-continued
66
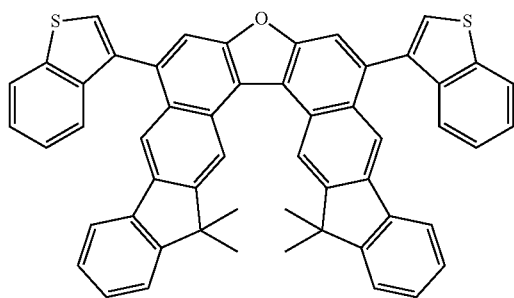
67
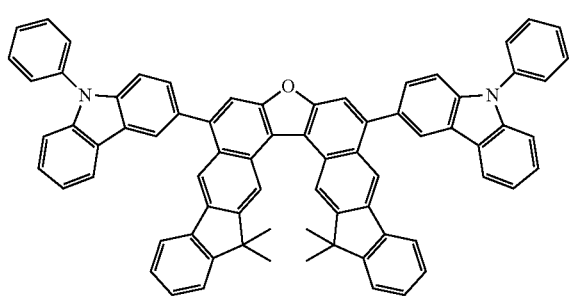
68
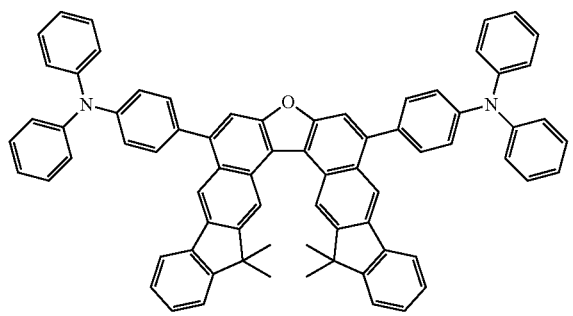
69
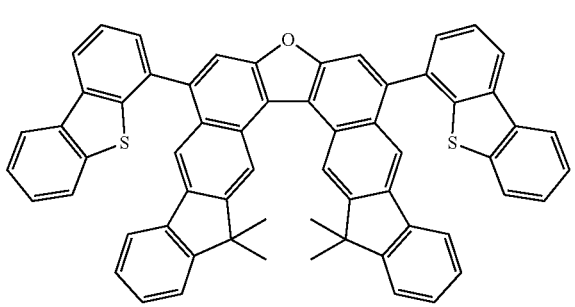
102
-continued
70
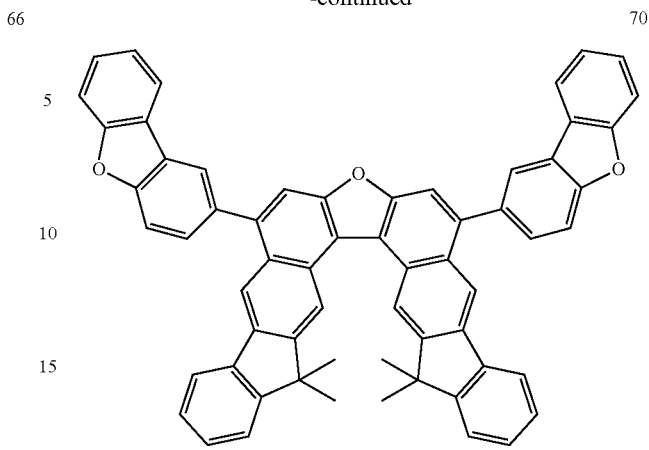
71
72
73
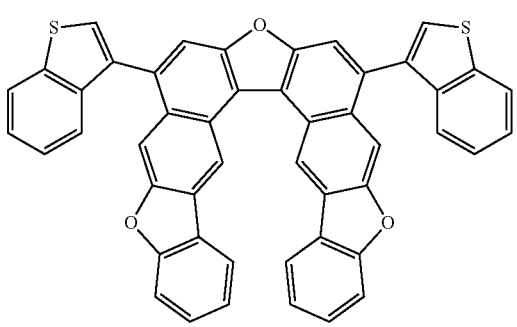

74
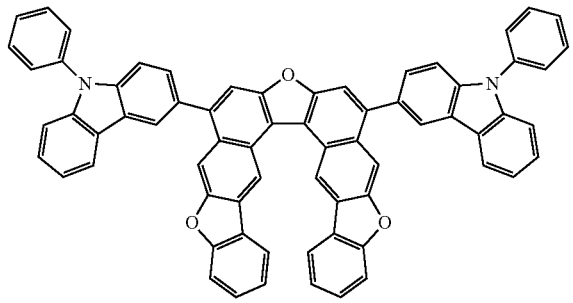
78
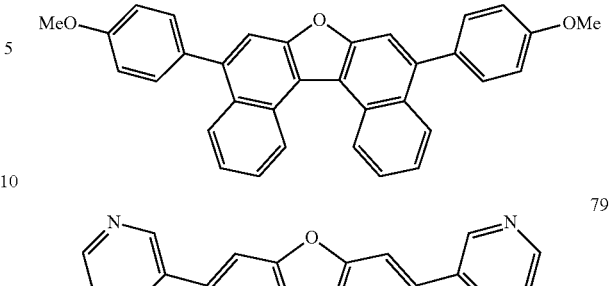
79
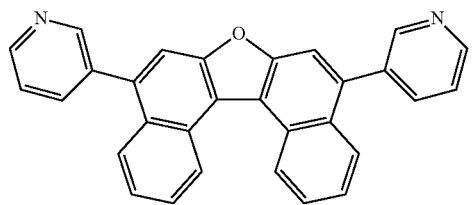
75
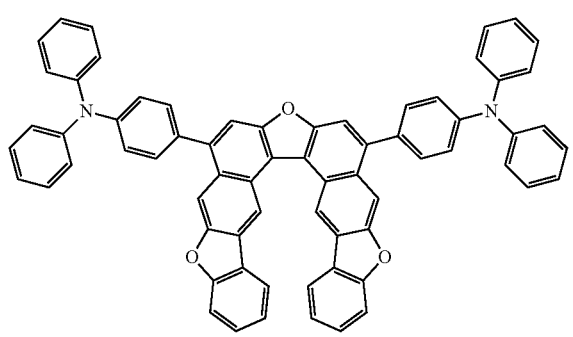
80
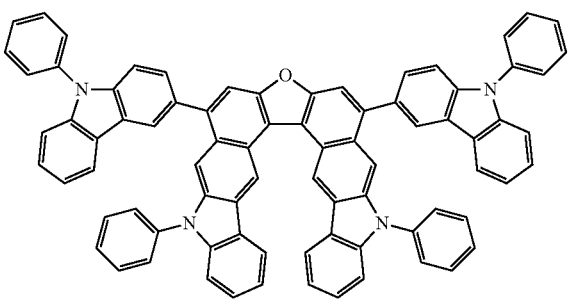
81
76
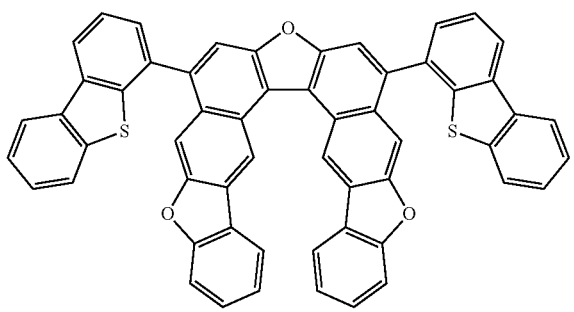
82
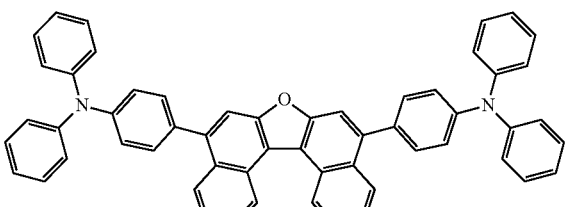
77
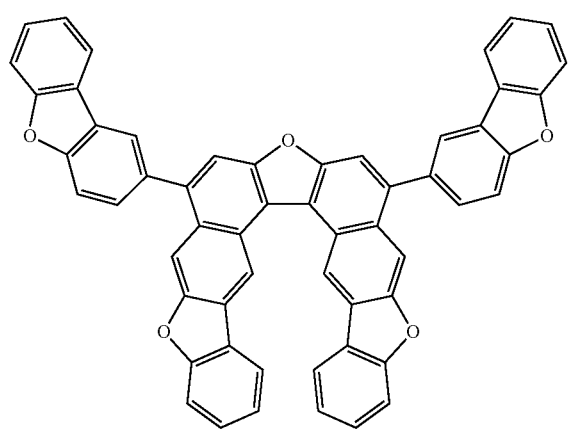
83
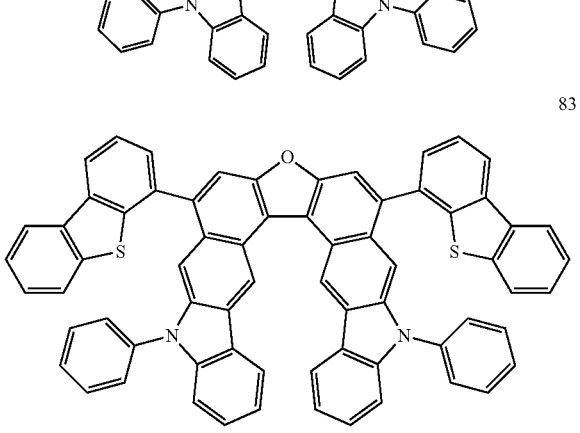

84
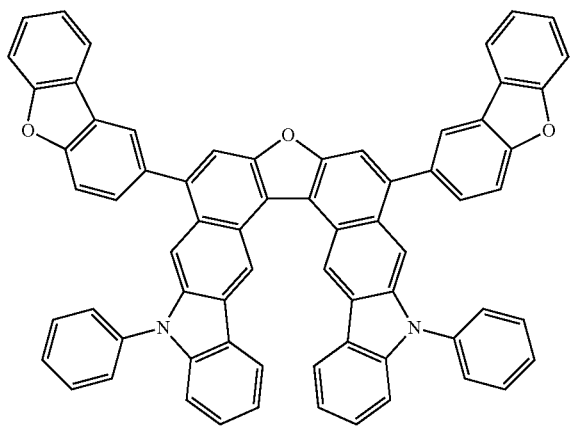
85
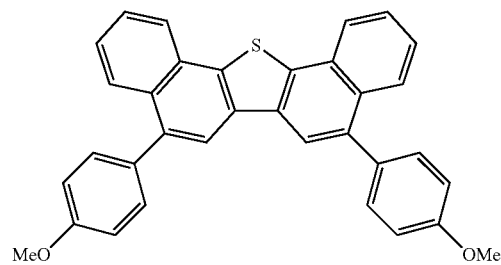
86
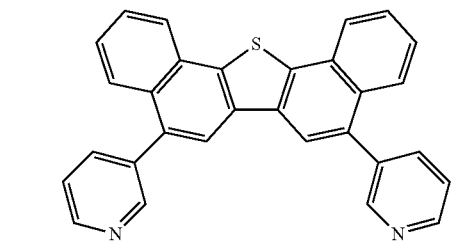
87
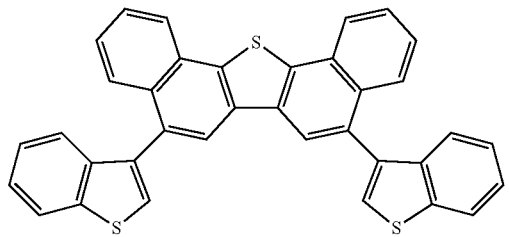
88
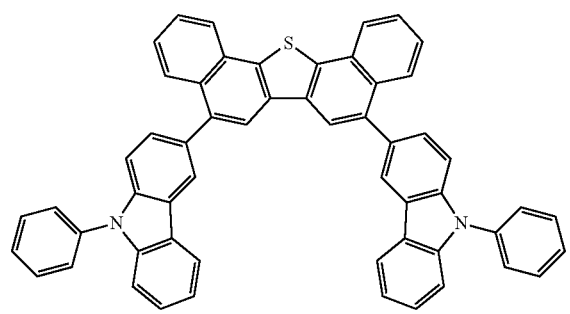
89
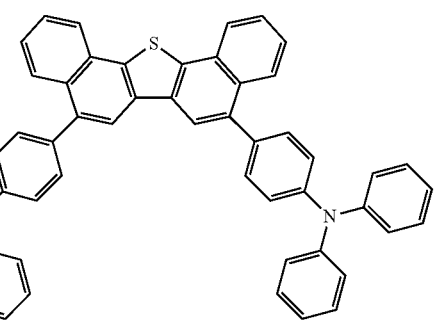
90
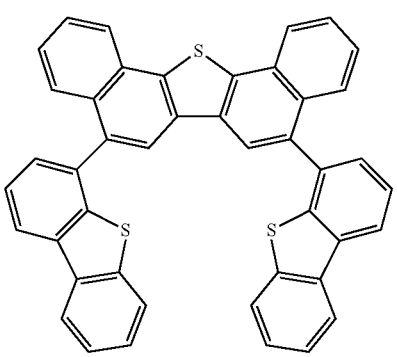
91
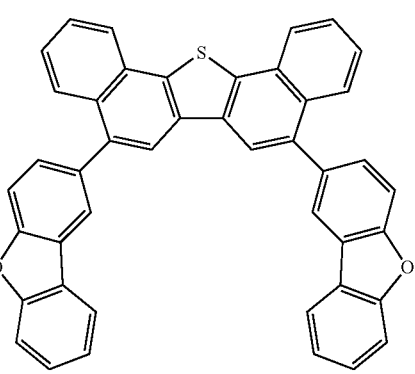
92
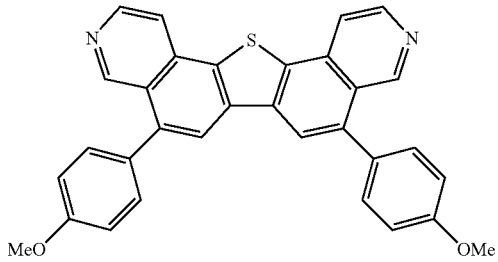
93
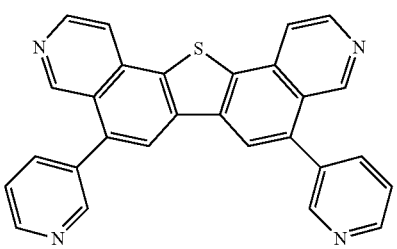

94
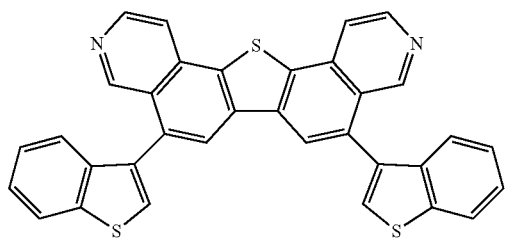
95
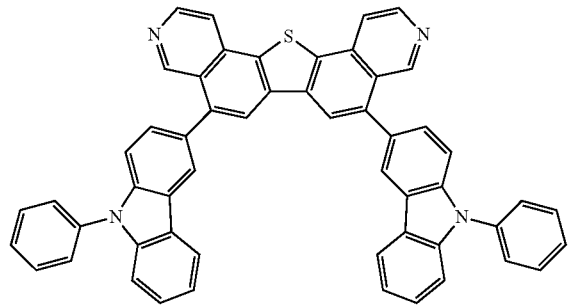
96
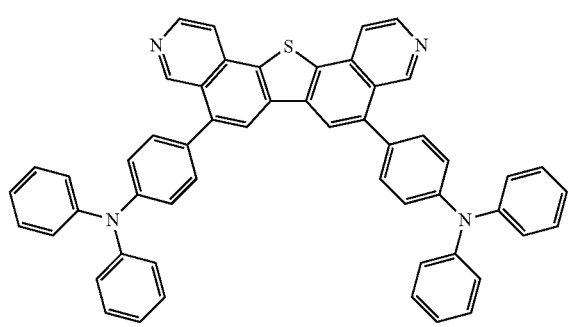
97
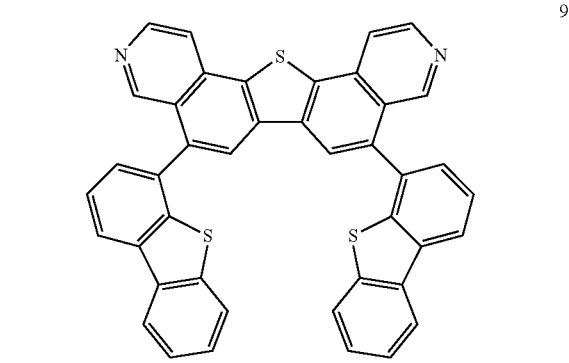
98
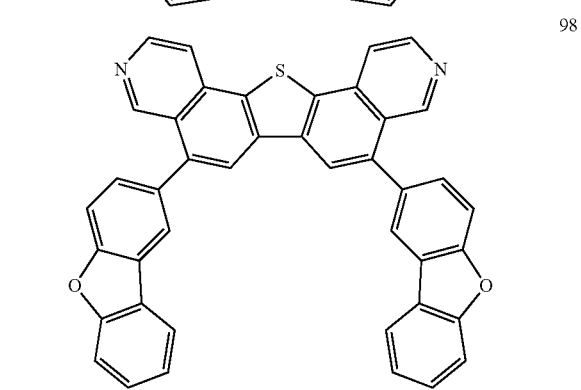
99
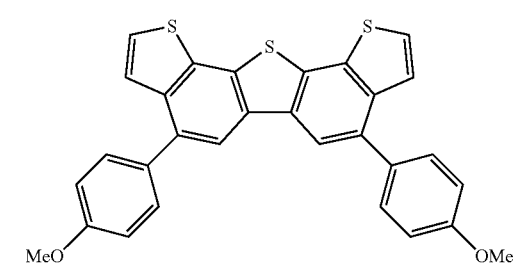
100
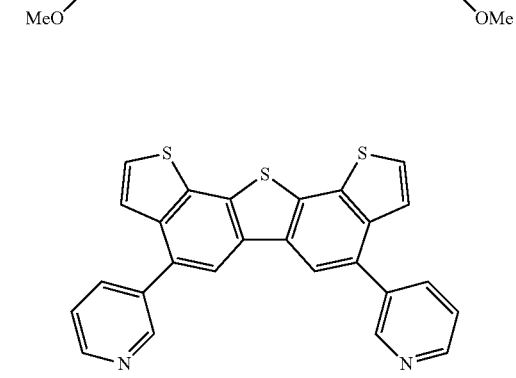
101
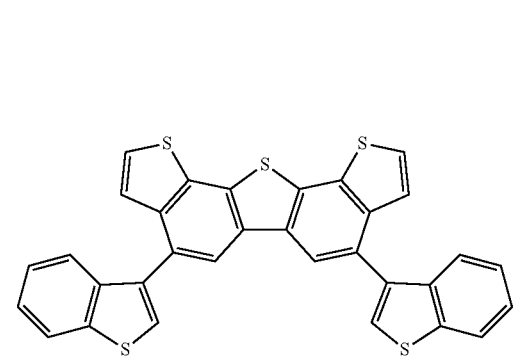
102
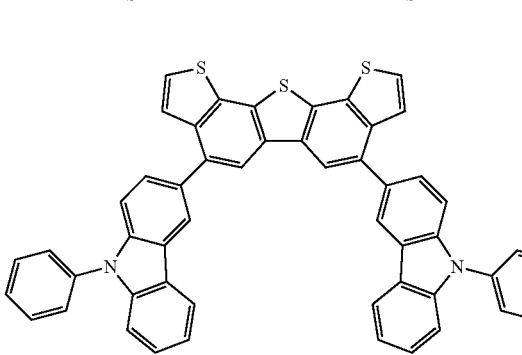
103
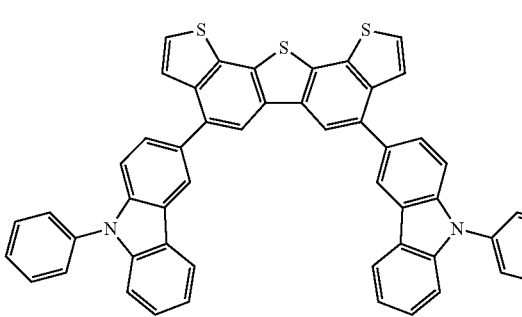

104
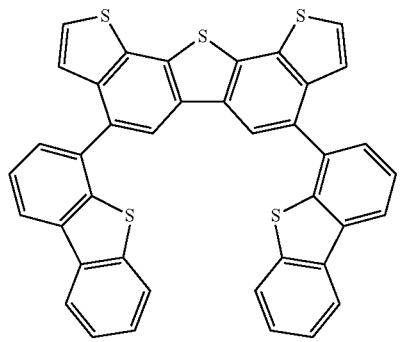
105
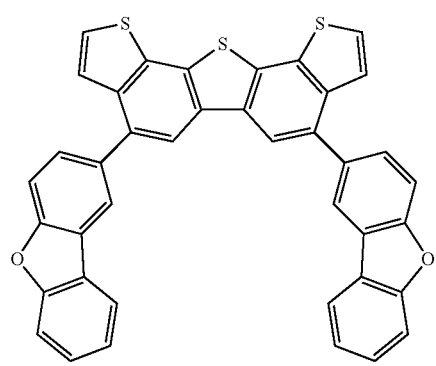
106
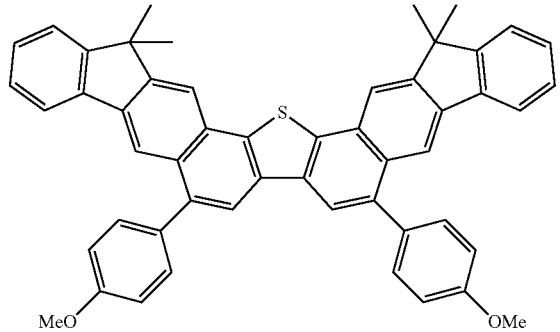
107
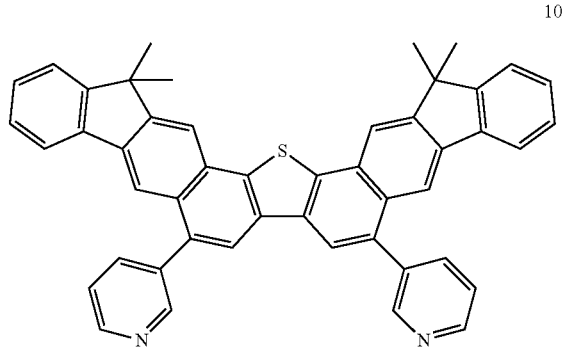
108
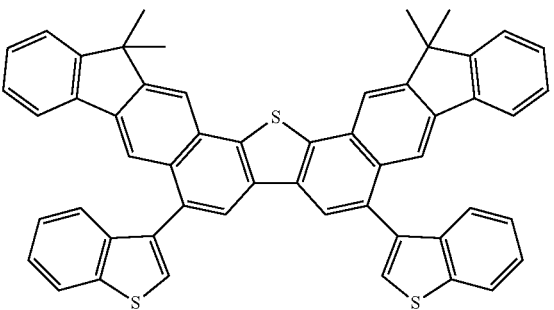
109
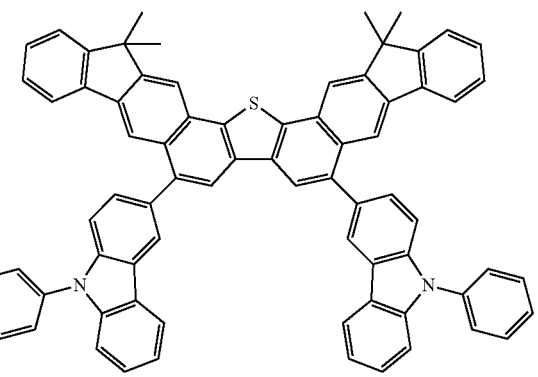
110
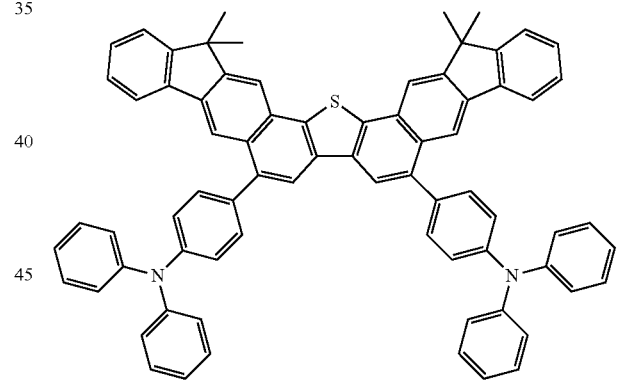
111
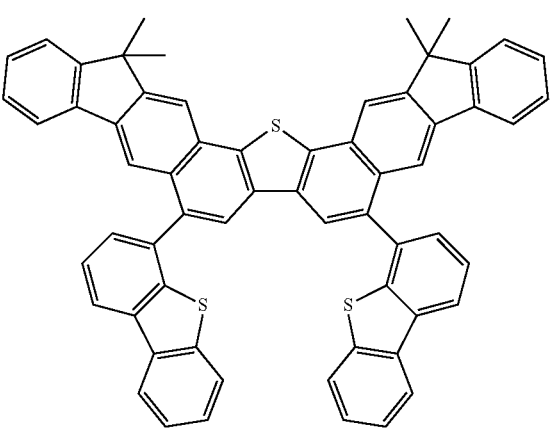

111
-continued
112
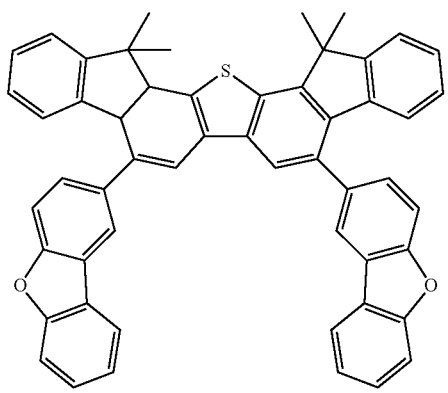
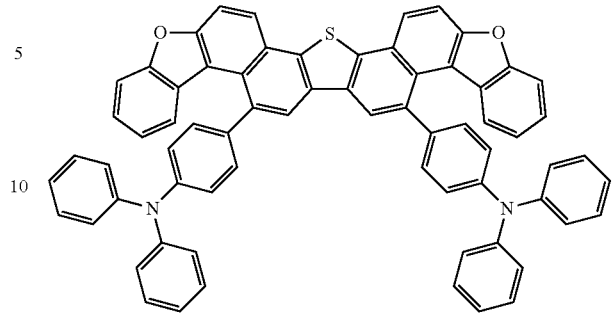
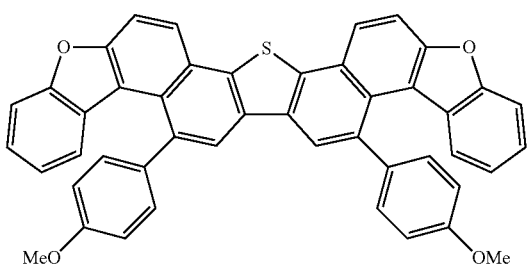
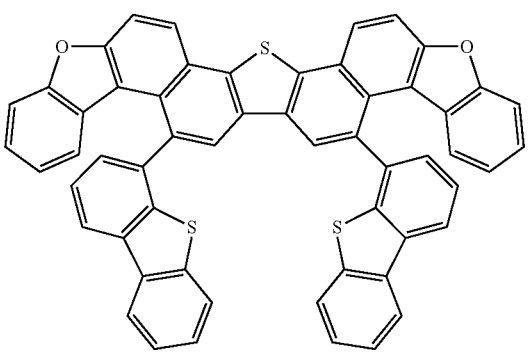
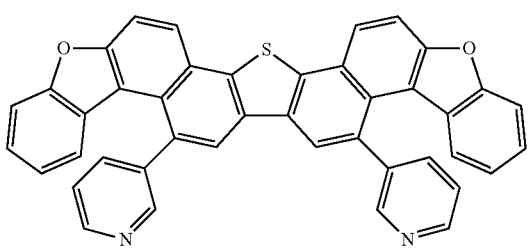
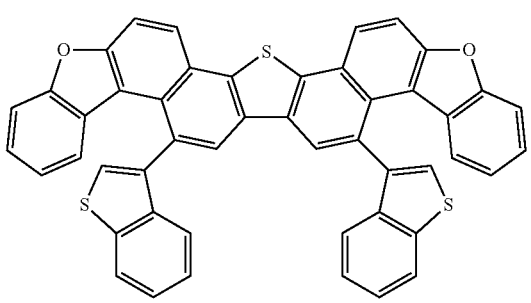
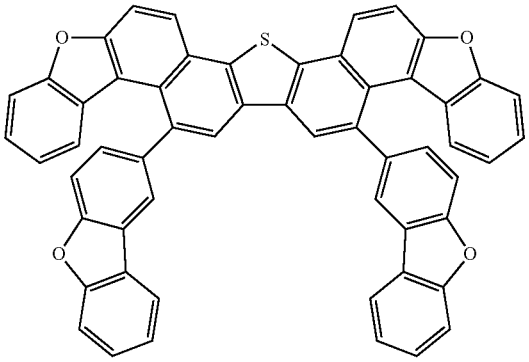
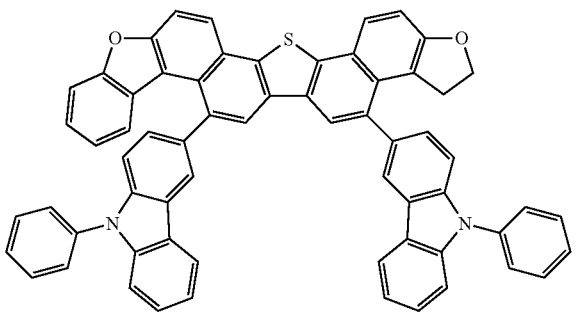
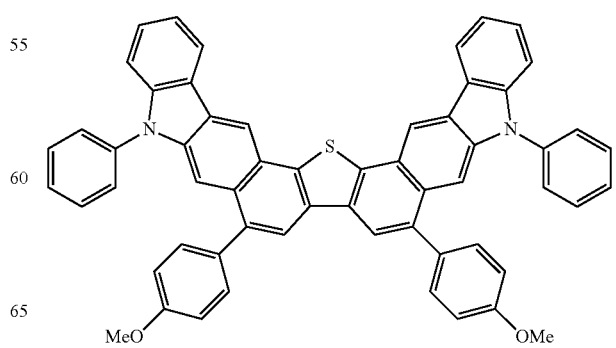

113
-continued
121
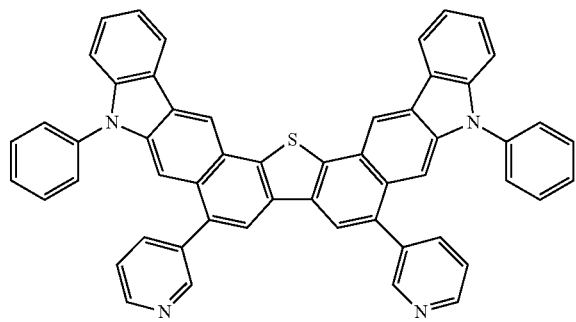
122
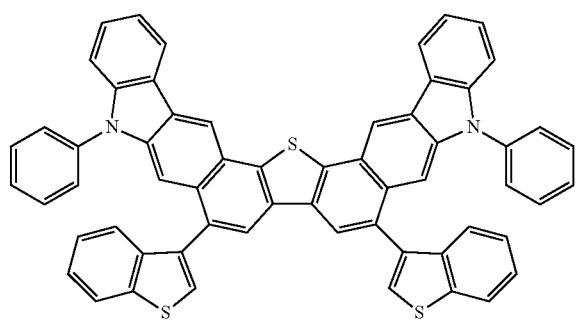
123
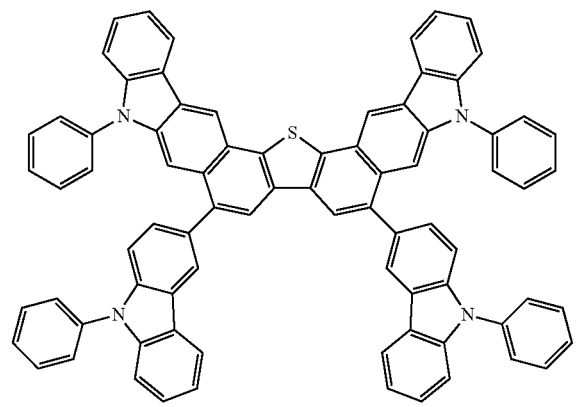
124
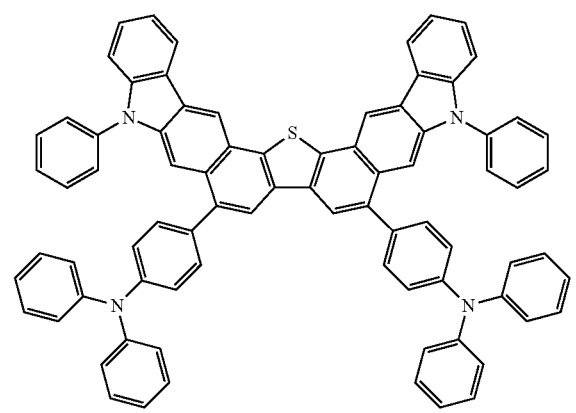
114
-continued
125
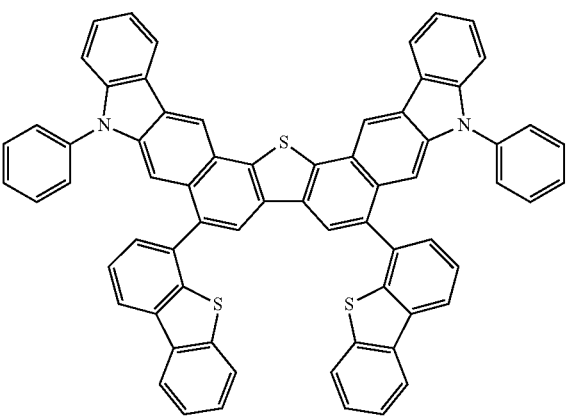
126
127
128
129
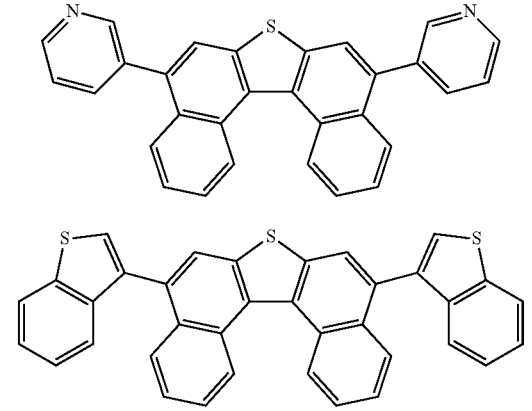

115
-continued
130
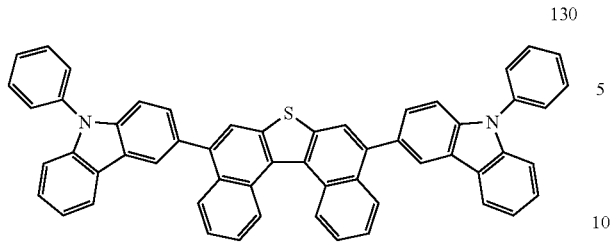
131
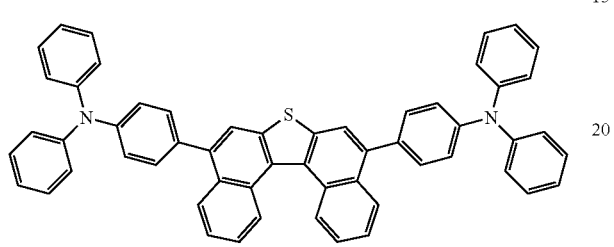
132
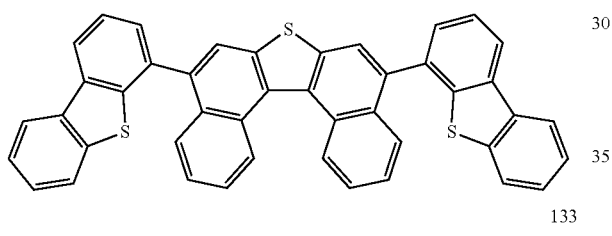
133
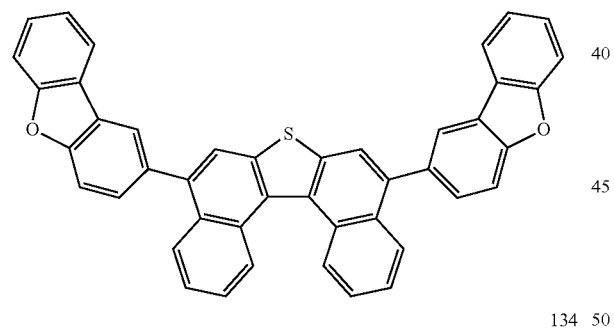
134
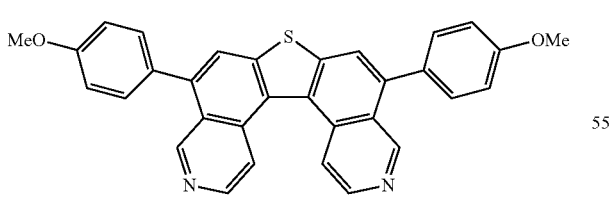
135
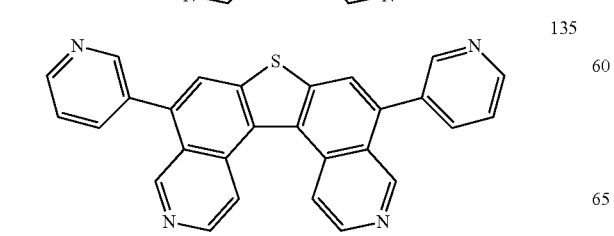
116
-continued
136
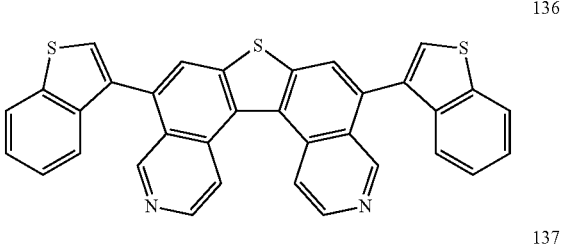
137
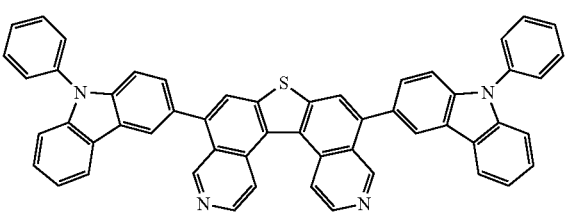
138
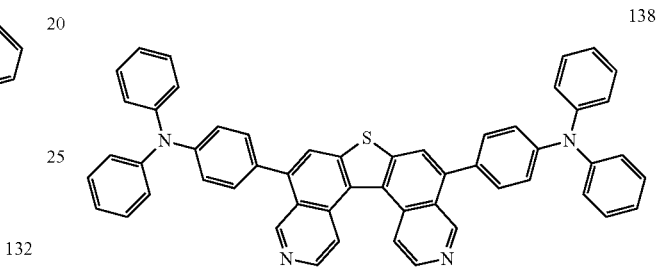
139
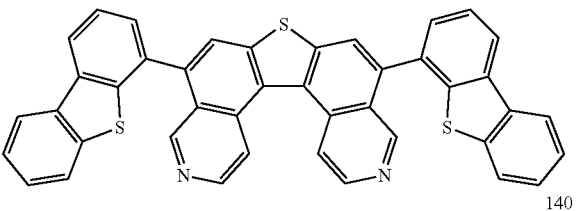
140
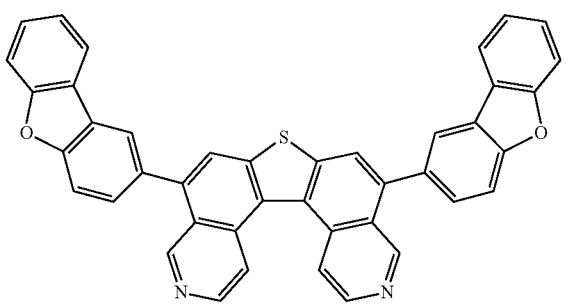
141
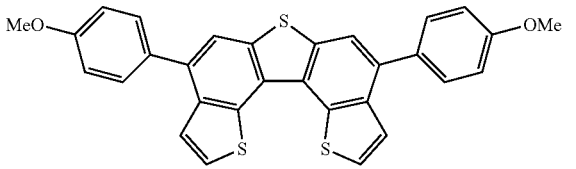
142
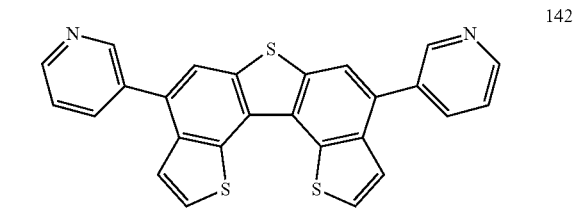

-continued
143
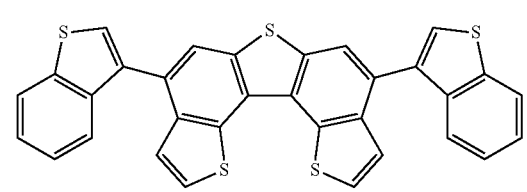
144
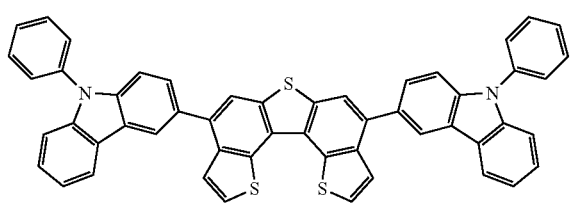
145
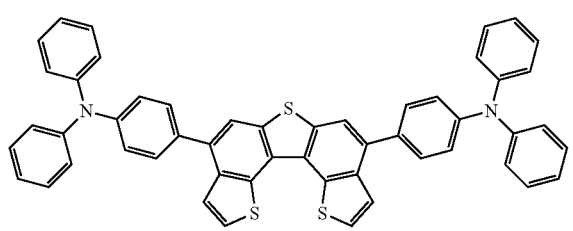
146
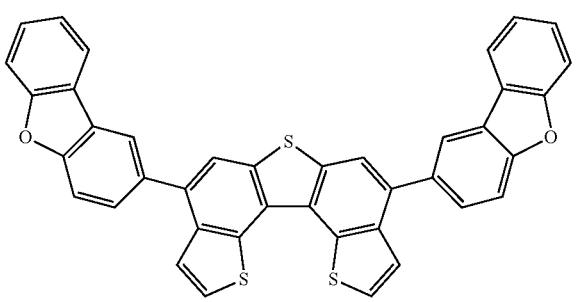
147
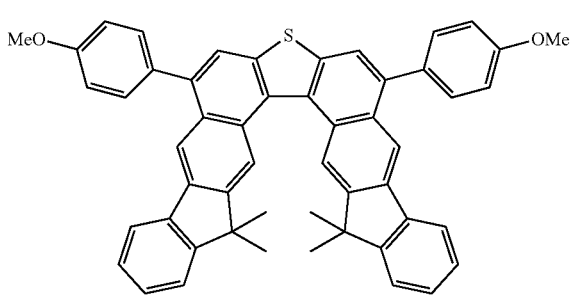
148
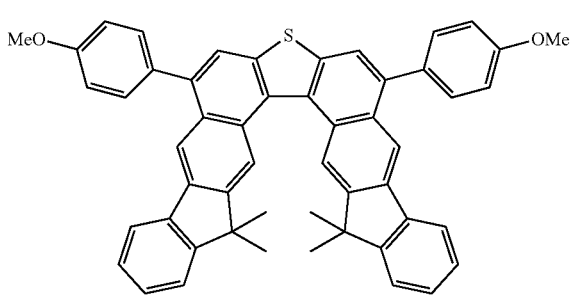
-continued
149
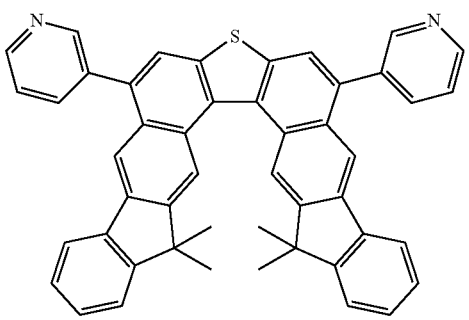
150
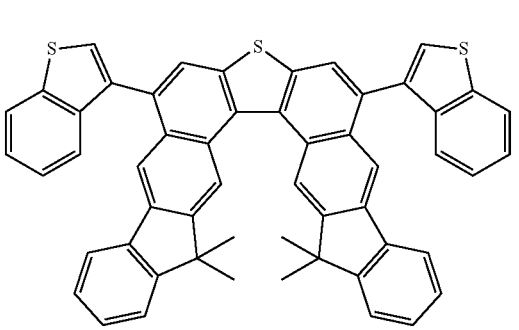
151
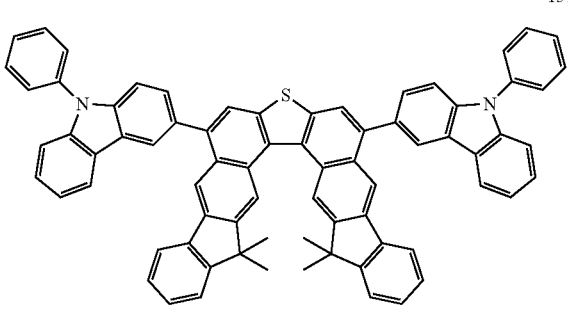
152
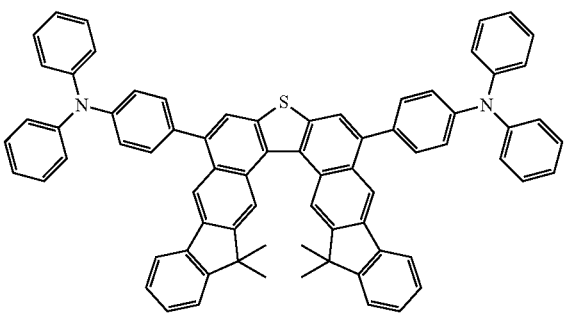
153
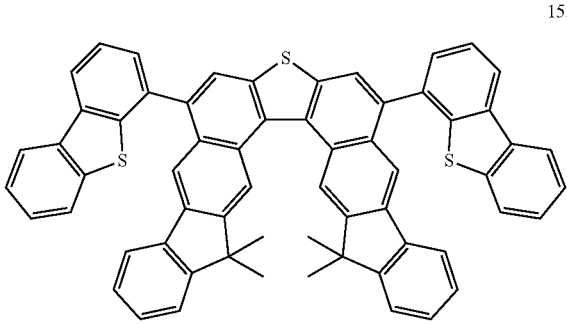

154
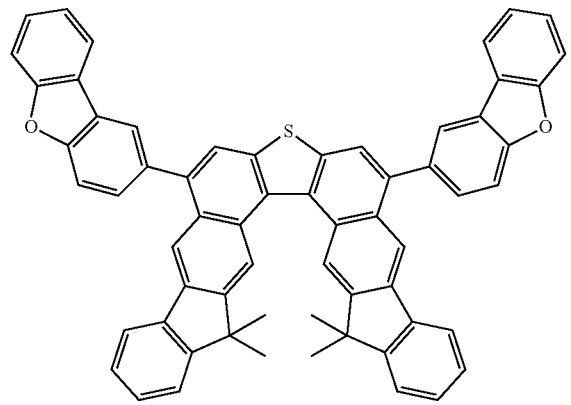
155
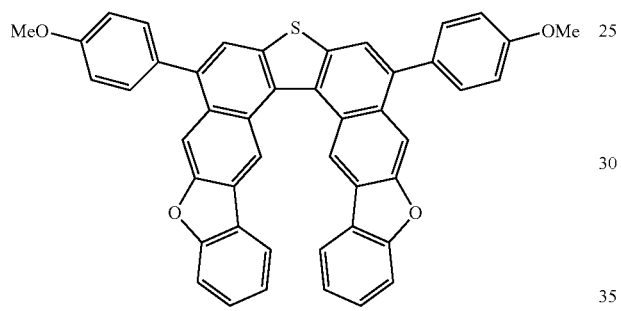
156
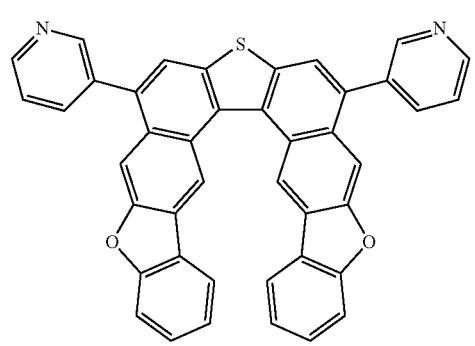
157
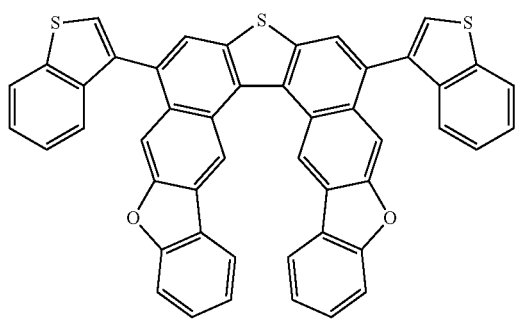
158
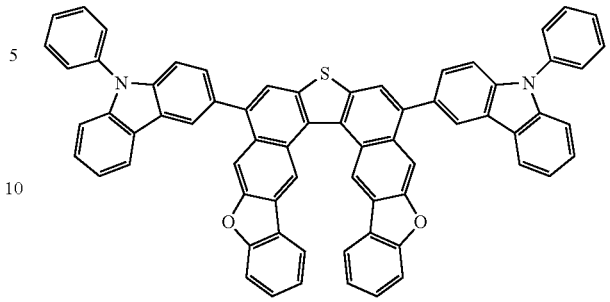
159
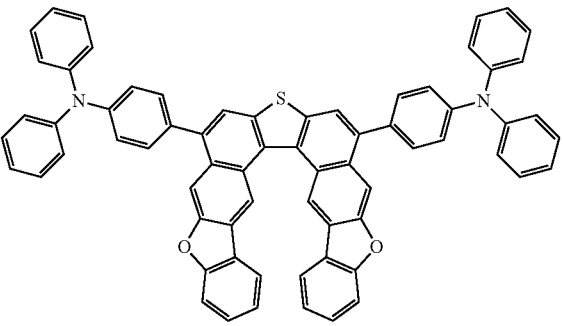
160
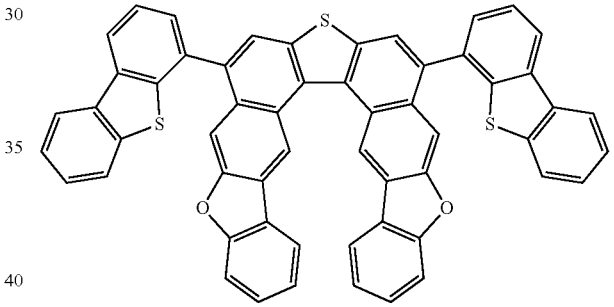
161
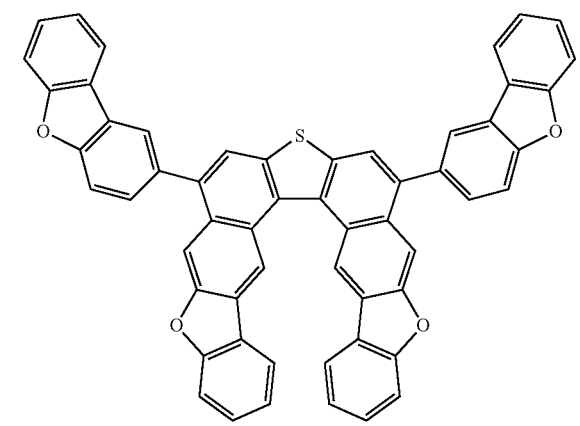
162
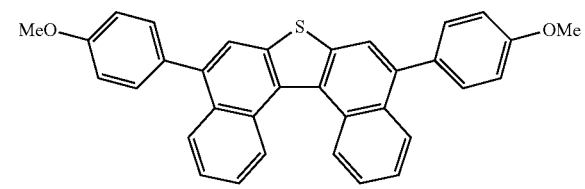

-continued

163
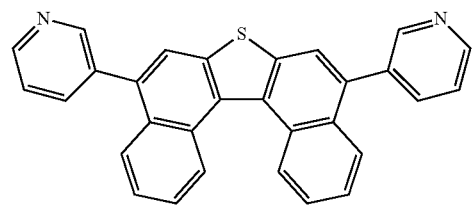

164
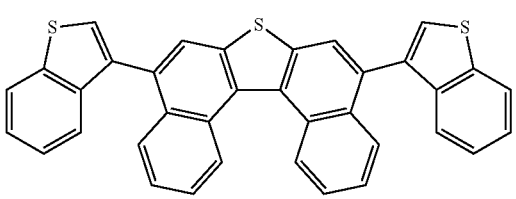

165
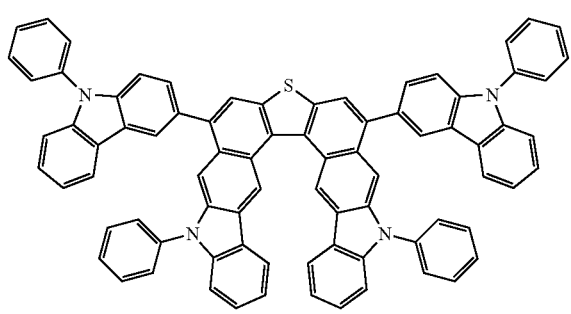

166
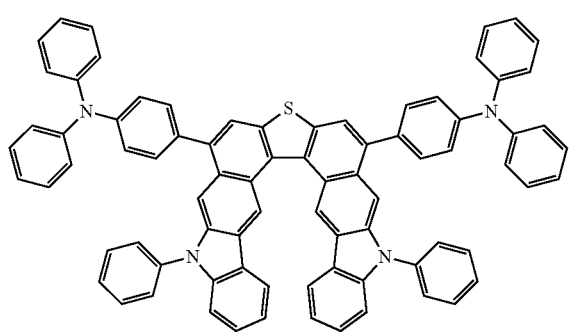

167
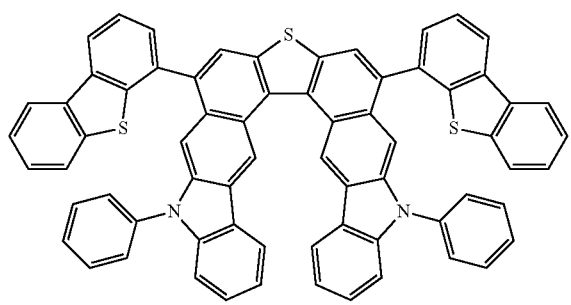

-continued

168
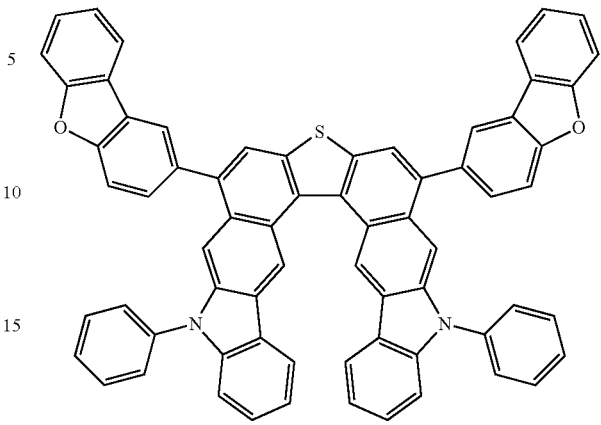

10. An organic light-emitting device comprising a first electrode, a second electrode facing the first electrode, and an organic layer between the first electrode and the second electrode, the organic layer comprising the heterocyclic compound of claim 1.

11. The organic light-emitting device of claim 10, wherein the organic layer comprises at least one of a hole injection layer, a hole transport layer, a functional layer having both hole injection and hole transport capabilities, a buffer layer, an emission layer, a hole blocking layer, an electron transport layer, an electron injection layer, and/or a functional layer having both electron injection and electron transport capabilities.

12. The organic light-emitting device of claim 10, wherein the organic layer comprises at least one of a hole injection layer, a hole transport layer, and/or a functional layer having both hole injection and hole transport capabilities, and at least one of the hole injection layer, the hole transport layer, and/or the functional layer having both hole injection and hole transport capabilities comprises the heterocyclic compound.

13. The organic light-emitting device of claim 12, wherein at least one of the hole injection layer, the hole transport layer, and/or the functional layer having both hole injection and hole transport capabilities further comprises a charge-generating material, and the charge-generating material is at least one of a quinone derivative, a metal oxide, and/or a cyano group-containing compound.

14. The organic light-emitting device of claim 10, wherein the organic layer comprises at least one of an electron injection layer, an electron transport layer, and/or a functional layer having both electron injection and electron transport capabilities, and at least one of the electron injection layer, the electron transport layer, and/or the functional layer having both electron injection and electron transport capabilities comprises the heterocyclic compound.

15. The organic light-emitting device of claim 10, wherein the organic layer comprises an emission layer, and the emission layer comprises the heterocyclic compound.

16. The organic light-emitting device of claim 15, wherein the heterocyclic compound is a fluorescent or phosphorescent host.

17. The organic light-emitting device of claim 15, wherein the heterocyclic compound is a fluorescent dopant.

18. The organic light-emitting device of claim 10, wherein the organic layer comprises at least one of an emission layer, an electron injection layer, an electron transport layer, and/or a functional layer having both electron injection and electron transport capabilities, wherein at least one of the electron injection layer, the electron transport layer, and/or the functional layer having both electron injection and electron transport capabilities comprises the heterocyclic compound; and the emission layer comprises an arylamine compound.

19. An organic light-emitting display apparatus comprising: a transistor comprising a source, a drain, a gate, and an active layer; and the organic light-emitting device according to claim 10, wherein one of the source and the drain of the transistor is electrically connected to the first electrode of the organic light-emitting device.

* * * * *